(12) United States Patent
Greenhouse et al.

(10) Patent No.: US 8,889,906 B2
(45) Date of Patent: *Nov. 18, 2014

(54) TETRALIN AND INDANE DERIVATIVES AND USES THEREOF

(75) Inventors: Robert Greenhouse, Newark, CA (US); Ralph New Harris, III, Redwood City, CA (US); Saul Jaime-Figueroa, Fremont, CA (US); James M. Kress, Sanford, NC (US); David Bruce Repke, Milpitas, CA (US); Russell Stephen Stabler, Boulder Creek, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/314,525

(22) Filed: Dec. 8, 2011

(65) Prior Publication Data

US 2012/0088837 A1    Apr. 12, 2012

Related U.S. Application Data

(63) Continuation of application No. 11/985,459, filed on Nov. 15, 2007, now Pat. No. 8,093,424, which is a continuation of application No. 11/315,706, filed on Dec. 21, 2005, now Pat. No. 7,312,359.

(60) Provisional application No. 60/638,030, filed on Dec. 21, 2004.

(51) Int. Cl.

| | | |
|---|---|---|
| C07C 303/00 | (2006.01) |
| C07C 307/00 | (2006.01) |
| C07C 309/00 | (2006.01) |
| C07C 311/00 | (2006.01) |
| A01N 47/28 | (2006.01) |
| A61K 31/17 | (2006.01) |
| A01N 37/18 | (2006.01) |
| A61K 31/16 | (2006.01) |
| C07D 207/36 | (2006.01) |
| C07D 235/06 | (2006.01) |
| C07D 233/34 | (2006.01) |
| C07D 209/30 | (2006.01) |
| C07D 233/90 | (2006.01) |
| C07D 239/42 | (2006.01) |
| C07C 317/32 | (2006.01) |
| C07C 317/44 | (2006.01) |
| C07D 233/48 | (2006.01) |
| C07D 239/14 | (2006.01) |
| C07D 207/325 | (2006.01) |
| C07D 233/88 | (2006.01) |
| C07D 207/16 | (2006.01) |
| C07D 233/84 | (2006.01) |
| C07D 233/54 | (2006.01) |
| C07D 207/34 | (2006.01) |
| C07D 233/64 | (2006.01) |
| C07D 231/18 | (2006.01) |
| C07D 233/20 | (2006.01) |
| C07D 277/82 | (2006.01) |

(52) U.S. Cl.
CPC ............ C07D 233/34 (2013.01); C07D 207/36 (2013.01); C07C 2102/08 (2013.01); C07D 235/06 (2013.01); C07D 209/30 (2013.01); C07D 233/90 (2013.01); C07D 239/42 (2013.01); C07C 317/32 (2013.01); C07C 317/44 (2013.01); C07D 233/48 (2013.01); C07D 239/14 (2013.01); C07D 207/325 (2013.01); C07D 233/88 (2013.01); C07D 207/16 (2013.01); C07D 233/84 (2013.01); C07D 233/54 (2013.01); C07D 207/34 (2013.01); C07D 233/64 (2013.01); C07D 231/18 (2013.01); C07D 233/20 (2013.01); C07D 277/82 (2013.01); C07C 2102/10 (2013.01)
USPC ................ 564/84; 564/80; 514/588; 514/613

(58) Field of Classification Search
None
See application file for complete search history.

(56) References Cited

U.S. PATENT DOCUMENTS

| | | | | |
|---|---|---|---|---|
| 7,312,359 B2 * | 12/2007 | Greenhouse et al. | ......... | 564/147 |
| 7,981,923 B2 * | 7/2011 | Harris et al. | ................. | 514/424 |
| 8,093,424 B2 * | 1/2012 | Greenhouse et al. | ........... | 564/86 |

OTHER PUBLICATIONS

Preventing Alzheimer's Disease What Do We Know, National Institutes on Aging, 1-28, 2012.*

* cited by examiner

*Primary Examiner* — Clinton Brooks
(74) *Attorney, Agent, or Firm* — Robert C. Hall

(57) ABSTRACT

Compounds of the formula I:

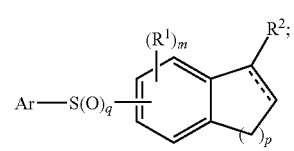

I or pharmaceutically acceptable salts thereof,
wherein m, p, q, Ar, $R^1$ and $R^2$ are as defined herein. Also provided are methods for preparing, compositions comprising, and methods for using compounds of formula I.

6 Claims, No Drawings

TETRALIN AND INDANE DERIVATIVES AND USES THEREOF

CROSS REFERENCE TO RELATED APPLICATIONS

This Application is a Continuation of U.S. application Ser. No. 11/985,459 filed on Nov. 15, 2007, now U.S. Pat. No. 8,093,424, which is a continuation of U.S. patent application Ser. No. 11/315,706 filed on Dec. 21, 2005, now U.S. Pat. No. 7,312,359, which claims the benefit under Title 35 U.S.C. 119(e) of U.S. Provisional Application Nos. 60/638,030 filed Dec. 21, 2004. The disclosures of the aforementioned applications are incorporated herein by reference in their entirety.

FIELD OF THE INVENTION

This invention relates to substituted indane and tetralin compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

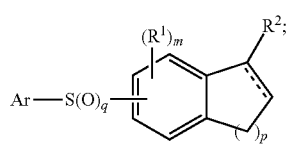

or a pharmaceutically acceptable salt thereof, wherein:
m is from 0 to 3;
p is from 1 to 3;
q is 0, 1 or 2;
Ar is optionally substituted aryl or optionally substituted heteroaryl;
---- is an optional bond;
each $R^1$ is independently halo, alkyl, haloalkyl, alkoxy, hydroxy, heteroalkyl, cyano, —S(O)$_t$—$R^a$, —C(=O)—$NR^bR^c$, —SO$_2$—$NR^bR^c$, —N($R^d$)—C(=O)—$R^e$, or —C(=O)—$R^e$, where t is from 0 to 2, $R^a$, $R^b$, $R^c$, $R^d$ and $R^e$ each independently is hydrogen or alkyl, and $R^f$ is hydrogen, alkyl, alkoxy or hydroxy;
$R^2$ is

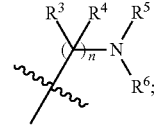

n is from 1 to 3;
$R^3$ and $R^4$ each independently is hydrogen or alkyl, or $R^3$ and $R^4$ together may form =O or =$NR^f$ wherein $R^f$ is hydrogen or alkyl; and
one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxyalkyl; alkylsulfonylalkyl; or optionally substituted heteroaryl; or
$R^5$ and $R^6$ together with the nitrogen to which they are attached may form an amidinyl group, a urea group, a guanidinyl group or a five- or six-membered heteroaryl or heterocyclyl ring that is optionally substituted and which optionally includes an additional heteroatom selected from O, N and S; or
one of $R^5$ and $R^6$ and one of $R^3$ and $R^4$ together with the atoms to which they are attached may form a five- or six-membered ring that optionally includes an additional heteroatom selected from O, N and S.

The invention also provides methods for preparing, methods of using, and pharmaceutical compositions comprising the aforementioned compounds.

DETAILED DESCRIPTION OF THE INVENTION

The invention provides substituted quinolinone compounds, associated compositions, methods for use as therapeutic agents, and methods of preparation thereof. In specific embodiments the invention provides piperazinyl-substituted quinolinone compounds and associated pharmaceutical compositions, and methods for using the same in the treatment of central nervous system (CNS) diseases and gastrointestinal tract disorders.

All publications cited in this disclosure are incorporated herein by reference in their entirety.

Definitions

Unless otherwise stated, the following terms used, in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Antagonist" refers to a compound that diminishes or prevents the action of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$-$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH═CH—), 2,2-dimethylethenylene, propenylene, 2-methylpropenylene, butenylene, pentenylene, and the like.

"Alkylcarbonyl means a group of the formula —C(O)—R wherein R is alkyl as defined herein.

"Alkylcarbonylaminoalkyl" means a group of the formula —R—NR'—R" wherein R is alkylene, R' is hydrogen or alkyl, and R" is alkylcarbonyl as defined herein.

"Alkylsulfonyl" means a group —$SO_2$—R wherein R is alkyl as defined herein.

"Alkylsulfonylalkyl" means a group —R—$SO_2$—R' wherein R' is alkyl and R is alkylene as defined herein.

"Alkylsulfonylalkylaminoalkyl" means a group of the formula —R—NR'—R" wherein R is alkylene, R' is hydrogen or alkyl, and R" is alkylsulfonylalkyl as defined herein.

"Alkylsulfonamidoalkyl means a group of the formula —R—NR'—$SO_2$—R" wherein R is alkylene, R' is hydrogen or alkyl, and R" is alkyl as defined herein.

"Alkoxy" means a group —OR, wherein R is alkyl as defined herein. Examples of alkoxy moieties include, but are not limited to, methoxy, ethoxy, isopropoxy, and the like.

"Alkoxycarbonyl" means a group of the formula —C(O)—R wherein R is alkoxy as defined herein.

"Alkoxycarbonylaminoalkyl" means a group of the formula —R—NR'—R" wherein R is alkylene, R' is hydrogen or alkyl, and R" is alkoxycarbonyl as defined herein.

"Alkoxycarbonylalkyl" means a group of the formula —R—C(O)—R' wherein R' is alkoxy and R is alkylene as defined herein.

"Alkoxycarbonylalkylaminoalkyl" means a group of the formula —R—NR'—R" wherein R is alkylene, R' is hydrogen or alkyl, and R" is alkoxycarbonyl alkyl as defined herein.

"Alkoxyalkyl" is a group of the formula —R—OR' wherein R' is alkyl and R is alkylene as defined herein.

"Alkoxyalkylaminoalkyl" means a group of the formula —R—NR'—R" wherein R is alkylene, R' is hydrogen or alkyl, and R" is al coxyalkyl as defined herein.

"Amino" means a group —NRR' wherein R and R' each independently is hydrogen or alkyl as defined herein. "Amino" thus includes "alkylamino" and "dialkylamino".

"Amidinyl" means a group of the formula:

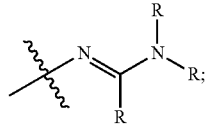

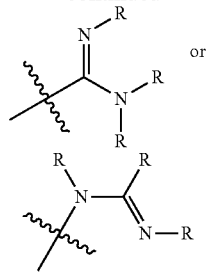

wherein each R independently is hydrogen or alkyl as defined herein. "N-cyanoamidinyl" means a group of the formula

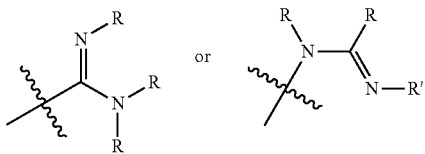

wherein R' is cyano and R is hydrogen or alkyl as defined herein.

"Aminosulfonyl means a group —$SO_2$—R wherein R is —NR'— and R' is hydrogen or alkyl as defined herein.

"Amidinylalkyl" means a group —R—R' wherein R' is amidinyl and R is alkylene as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Alkylaminoalkyl" means a group of the formula —R—NR'—R" wherein R' is hydrogen or alkyl, R" is alkyl, and R is alkylene as defined herein. "Dialkylaminoalkyl" is alkylaminoalkyl wherein R' is alkyl.

"Aminocarbonyl" means a group of the formula —C(O)—R wherein R is amino as defined herein.

"Aminocarbonylalkyl" means a group of the formula —R—C(O)—R' wherein R' is amino and R is alkylene as defined herein.

"Aminocarbonylalkylaminoalkyl means a group of the formula —R—NR'—R" wherein R is alkylene, R' is hydrogen or alkyl, and R" is aminocarbonylalkyl as defined herein.

"Aminoalkylcarbonyl" means a group of the formula —C(O)—R—R' wherein R' is amino and R is alkylene as defined herein.

"Aminoalkylcarbonylaminoalkyl" means a group of the formula —R—NR'—R" wherein R is alkylene, R' is hydrogen or alkyl, and R" is aminocarbonylalkyl as defined herein.

"Aminosulfonamidoalkyl" means a group of the formula —R—NR'—$SO_2$—R" wherein R is alkylene, R' is hydrogen or alkyl, and R" is amino as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —R—R' where R is an alkylene group and R' is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R—R', where R is alkylene and R' is cycloalkyl as defined herein.

"Guanidinyl" means a group of the formula

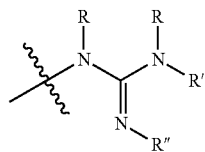

wherein each R independently is hydrogen or alkyl, R' is hydrogen, alkyl, or phenyl, and R" is hydrogen, alkyl or cyano. The phenyl moiety of "guanidinyl" may be optionally substituted as defined herein. "N-cyanoguanidinyl" means R" in the formula for guanidinyl is cyano.

"Guanidinylalkyl" is a group —R—R' wherein R' is guanidinyl and R is alkylene as defined herein. "N-cyanoguanidinylalkyl means R' is N-cyanoguanidinyl as defined herein.

"Guanidinylcarbonylalkyl" means a group of the formula —R—C(O)—R' wherein R' is guanidinyl and R is alkylene as defined herein.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, methoxy, ethoxy, 2-hydroxyethyl, 3-hydroxypropyl, 2-methoxyethyl, 3-methoxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof. The aforementioned heteroaryl moieties may be partially saturated. Thus, "heteroaryl" includes "imidazolinyl", tetrahydropyrimidinyl" and the like.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

"Heteroarylaminoalkyl" means a group of the formula —R—NR'—R" wherein R is alkylene, R' is hydrogen or alkyl, and R" is heteroaryl as defined herein.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Hydroxyalkyl" means an alkyl as defined herein that is substituted one, two or three times with hydroxy.

"Hydroxyalkylcarbonyl" means a group of the formula —C(O)—R—OH wherein R is alkylene as defined herein.

"Hydroxyalkylcarbonylaminoalkyl" means a group of the formula —R—NR'—R" wherein R is alkylene, R' is hydrogen or alkyl, and R" is hydroxyalkylcarbonyl as defined herein.

"Hydroxyalkylaminoalkyl" means a group of the formula —R—NR'—R" wherein R is alkylene, R' is hydrogen or alkyl, and R" is hydroxyalkyl as defined herein.

"Imidazolinyl" means a group of the formula

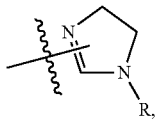

and more preferably a group of the formula

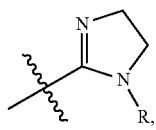

wherein R is hydrogen or alkyl. "Imidazolinyl" may be interchangeably used with "4,5-dihydro-1H-imidazol-2-yl".

"Imidazolonyl" means a group of the formula

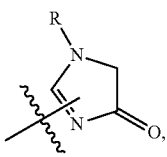

and more preferably a group of the formula

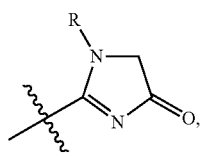

wherein R is hydrogen or alkyl.

"Imidazolonylaminoalkyl means a group of the formula —R—NR'—R" wherein R is alkylene, R' is hydrogen or alkyl, and R" is imidazolonyl as defined herein.

"Imidazolinylalkyl" means a group —R—R' wherein R' is imidazolinyl as defined herein and R is alkylene.

"Imidazolinylaminoalkyl" means a group —R—R'—R" wherein R" is imidazolinyl as defined herein, R' is amino, and R is alkylene. The amino moiety of "imidazolinylaminoalkyl" may be optionally substituted with alkyl.

"Imidazolylcarbonyl" means a group of the formula

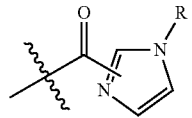

wherein R is hydrogen or alkyl as defined herein.

"Imidazolinylaminoalkyl" means a group of the formula —R—NR'—R" wherein R is alkylene, R' is hydrogen or alkyl, and R" is imidazolinyl as defined herein.

"Imidazolylaminoalkyl" means a group of the formula —R—NR'—R" wherein R is alkylene, R' is hydrogen or alkyl as defined herein, and R" is imidazolyl.

"Imidazolinylalkyl" is a group of the formula —R—R" wherein R is alkylene and R" is imidazolinyl as defined herein "Imidazolinylcarbonylaminoalkyl" means a group of the formula —R—C(O)—NR'—R" wherein R is alkylene, R' is hydrogen or alkyl, and R" is imidazolinyl as defined herein.

"Pyrimidinylaminoalkyl" means a group —R—R'—R" wherein R" is pyrimidinyl (preferably pyrimidin-2-yl), R' is amino, and R is alkylene. The pyrimidinyl moiety of "pyrimidinylaminoalkyl" may be optionally substituted as defined herein, and the amino moiety of "pyrimidinylaminoalkyl" may be optionally substituted with alkyl.

"Pyrrolylcarbonyl" means a group of the formula

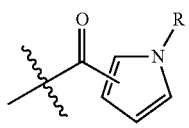

wherein R is hydrogen or alkyl as defined herein.

"Pyrrolylcarbonylaminoalkyl" means a group of the formula —R—NR'—R" wherein R is alkylene, R' is hydrogen or alkyl, and R" is pyrrolylcarbonyl as defined herein.

"Pyrrolidinylcarbonyl" means a group of the formula

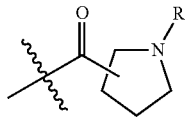

wherein R is hydrogen or alkyl as defined herein.

"Pyrrolidinylcarbonylaminoalkyl" means a group of the formula —R—NR'—R" wherein R is alkylene, R' is hydrogen or alkyl, and R" is pyrrolidinylcarbonyl as defined herein.

"Tetrahydropyrimidinyl" means 1,4,5,6-tetrahydropyrimidinyl, preferably 1,4,5,6-tetrahydropyrimidin-2-yl, and may be optionally substituted as defined herein. "Tetrahydropyrimidinyl" includes 5,5-dimethyl-1,4,5,6-tetrahydropyrimidin-2-yl.

"Tetrahydropyrimidinylaminoalkyl" means a group —R—NR'—R" wherein R" is tetrahydropyrimidinyl, R' is hydrogen or alkyl, and R is alkylene as defined herein.

"Urea" or "ureyl", which may be used interchangeably, means a group of the formula:

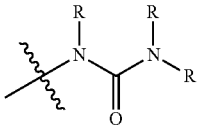

wherein each R is independently is hydrogen or alkyl.

"Urealkyl" means a group R—R' wherein R' is urea and R is alkylene as defined herein.

"Optionally substituted", when used in association with "aryl", phenyl", "heteroaryl", or "heterocyclyl", means an aryl, phenyl, heteroaryl, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined, herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
  acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or
  salts formed when an acidic proton present in the parent compound either is replaced by a metal ion, e.g., an alkali metal ion, an alkaline earth ion, or an aluminum ion; or coordinates with an organic or inorganic base.
    Acceptable organic bases include diethanolamine, ethanolamine, N-methylglucamine, triethanolamine, tromethamine, and the like.
    Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1-92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Those skilled in the art know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

NOMENCLATURE

In general, the nomenclature used in this Application is based on AUTONOM™ v.4.0, a Beilstein Institute computerized system for the generation of IUPAC systematic nomenclature.

Chemical structures shown herein were prepared using ISIS® version 2.2. Any open valency appearing on a carbon, oxygen or nitrogen atom in the structures herein indicates the presence of a hydrogen.

COMPOUNDS OF THE INVENTION

The invention provides compounds of the formula I:

It should be understood that the scope of this invention encompasses not only the various isomers which may exist but also the various mixture of isomers which may be formed. Furthermore, the scope of the present invention also encompasses solvates and salts of compounds of formula I:

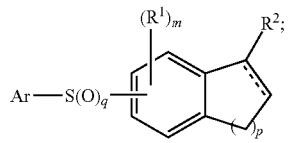

or a pharmaceutically acceptable salt thereof,
wherein:
  m is from 0 to 3;
  p is from 1 to 3;
  q is 0, 1 or 2;
  Ar is optionally substituted aryl or optionally substituted heteroaryl;
  ____ is an optional bond;
  each $R^1$ is independently halo, alkyl, haloalkyl, alkoxy, hydroxy, heteroalkyl, cyano, —S(O)$_t$—R$^a$, —C(=O)—NR$^b$R$^c$, —SO$_2$—NR$^b$R$^c$, —N(R$^d$)—C(=O)—R$^e$, or —C(=O)—R$^e$, where t is from 0 to 2, R$^a$, R$^b$, R$^c$, R$^d$ and R$^e$ each independently is hydrogen or alkyl, and R$^f$ is hydrogen, alkyl, alkoxy or hydroxy;
  $R^2$ is

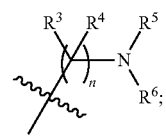

n is from 1 to 3;
  $R^3$ and $R^4$ each independently is hydrogen or alkyl, or $R^3$ and $R^4$ together may form =O or =NR$^f$ wherein R$^f$ is hydrogen or alkyl; and
  one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; alkylsulfonylalkyl; or optionally substituted heteroaryl; or
  $R^5$ and $R^6$ together with the nitrogen to which they are attached may form an amidinyl group, a urea group, a guanidinyl group or a five- or six-membered heteroaryl or heterocyclyl ring that is optionally substituted and which optionally includes an additional heteroatom selected from O, N and S; or
  one of $R^5$ and $R^6$ and one of $R^3$ and $R^4$ together with the atoms to which they are attached may form a five- or six-membered ring that optionally includes an additional heteroatom selected from O, N and S.

In many embodiments of formula I, p is 1 or 2. Preferably p is 2.
  In many embodiments of formula I, q is 2.
  In many embodiments of formula I, m is 0 or 1.
  In certain embodiments of formula I, $R^1$ is halo.
  In certain embodiments of formula I, the group Ar—S(O)$_q$— is located at the 6- or 7-position of the tetralin ring system.
  In certain embodiments of formula I, the group Ar—S(O)$_q$— is located at the 6-position of the tetralin ring system.
  In certain embodiments of formula I, m is 0 or 1 and $R^1$ is located at the 8-position of the tetralin ring system.
  In certain embodiments of formula I, n is 1.
  In certain embodiments of formula I, n is 2.

In certain embodiments of formula I, n is 3.

In certain embodiments of formula I, $R^3$ and $R^4$ are hydrogen.

In certain embodiments of formula I, one of $R^5$ and $R^6$ is hydrogen and the other is alkyl.

In certain embodiments of formula I, $R^5$ and $R^6$ are hydrogen.

In certain embodiments of formula I, one of $R^5$ and $R^6$ is hydrogen or alkyl and the other is: alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; or alkoxalkyl.

In certain embodiments of formula I, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.

In certain embodiments of formula I, one of $R^5$ and $R^6$ is hydrogen and the other is heteroaryl selected from pyrimidinyl, benzothiazol-2-yl, and 5,5-dimethyl-1,4,5,6-tetrahydropyrimidinyl.

In certain embodiments of formula I, $R^5$ and $R^6$ together with the nitrogen to which they are attached form an amidinyl group.

In certain embodiments of formula I, $R^5$ and $R^6$ together with the nitrogen to which they are attached form a guanidinyl group.

In certain embodiments of formula I, $R^5$ and $R^6$ together with the nitrogen to which they are attached form a urea group.

In certain embodiments of formula I, $R^3$ and $R^4$ together with the nitrogen to which they are attached form =$NR^f$ wherein $R^f$ is hydrogen.

In certain embodiments of formula I, $R^3$ and $R^4$ together with the nitrogen to which they are attached form =O.

In certain embodiments of formula I, one of $R^5$ and $R^6$ and one of $R^3$ and $R^4$ together with the atoms to which they are attached form an imidazolinyl ring.

In certain embodiments of formula I, $R^5$ and $R^6$ together with the nitrogen to which they are attached form or a five- or six-membered heteroaryl ring that is optionally substituted and which optionally includes an additional nitrogen heteroatom.

In certain embodiments of formula I, $R^5$ and $R^6$ together with the nitrogen to which they are attached form or a five-, or six-membered heteroaryl ring selected from pyridinyl, pyrimidinyl, pyrrolyl, imidazolyl or pyrazolyl, each optionally substituted.

In certain embodiments of formula I, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of formula I, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of formula I, Ar is optionally substituted phenyl.

In certain embodiments of formula I, Ar is 2-halophenyl or 3-halopheny.

In certain embodiments of formula I, Ar is heteroaryl.

In certain embodiments of formula I, Ar is heteroaryl selected from indolyl, pyrrolyl, imidazolyl, pyrazolyl, benzimidazolyl, thienyl, furanyl, pyridinyl and pyrimidinyl, each optionally substituted.

In certain embodiments of formula I, Ar is heteroaryl selected from indolyl, pyrrolyl, imidazolyl, pyrazolyl, and benzimidazolyl, each optionally substituted.

In certain embodiments of formula I, Ar is heteroaryl selected from indol-3-yl, pyrrol-3-yl, 1-methylimidazol-2-yl, imidazol-2-yl, pyrazol-4-yl, benzimidazol-4-yl, 6-fluoroindol-3-yl, 1-methylpyrrol-3-yl and 6-fluorobenzimidazol-4-yl.

In certain embodiments of formula I, one of $R^5$ and $R^6$ and one of $R^3$ and $R^4$ together with the atoms to which they are attached form an imidazolinyl ring.

In certain embodiments of formula I, p is 2 and q is 2.

In certain embodiments of formula I, p is 2, q is 2 and m is 0 or 1.

In certain embodiments of formula I, p is 2, q is 2, m is 0 or 1, and n is 1.

In certain embodiments of formula I, p is 2, q is 2, m is 0 or 1, n is 1, and $R^3$ and $R^4$ are hydrogen.

In certain embodiments of formula I, p is 2, q is 2, m is 0 or 1, n is 1, $R^3$ and $R^4$ are hydrogen, one of $R^5$ and $R^6$ is hydrogen or alkyl, and the other is: alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, p is 2, q is 2, m is 0 or 1, n is 1, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, p is 2, q is 2, m is 0 or 1, n is 1, $R^3$ and $R^4$ are hydrogen, one of $R^5$ and $R^6$ is hydrogen and the other is alkyl.

In certain embodiments of formula I, p is 2, q is 2, m is 0 or 1, and $R^2$ is: aminoalkyl; alkylaminoalkyl; dialkylaminoalkyl; imidazolinylaminoalkyl; imidazolinylalkyl, guanidinylalkyl; tetrahydropyrimidinylaminoalkyl; amidinylalkyl; urealkyl; amidinyl; heteroarylaminoalkyl; imidazolylaminoalkyl; guanidinylcarbonylalkyl; imidazolonylaminoalkyl; imidazolinylcarbonylaminoalkyl; aminocarbonylalkyl; pyrrolylcarbonylaminoalkyl; aminoalkylcarbonylaminoalkyl; alkoxycarbonylalkylaminoalkyl; N-cyanoguanidinylalkyl; alkylcarbonylaminoalkyl; aminocarbonylalkylaminoalkyl; pyrrolidinylcarbonylaminoalkyl; alkylsulfonamidoalkyl; aminosulfonamidoalkyl; alkoxycarbonylaminoalkyl; hydroxyalkylcarbonylaminoalkyl; hydroxyalkylaminoalkyl; alkoxyalkylaminoalkyl; or alkylsulfonylalkylaminoalkyl.

In certain embodiments of formula I, p is 2, q is 2, m is 0 or 1, and $R^2$ is: aminoalkyl; alkylaminoalkyl; dialkylaminoalkyl; guanidinylalkyl; amidinylalkyl; urealkyl; amidinyl; guanidinylcarbonylalkyl; aminocarbonylalkyl; aminoalkylcarbonylaminoalkyl; alkylcarbonylaminoalkyl; aminocarbonylalkylaminoalkyl; or alkoxycarbonylaminoalkyl.
In certain embodiments of formula I, p is 2, q is 2, m is 0 or 1, and $R^2$ is:
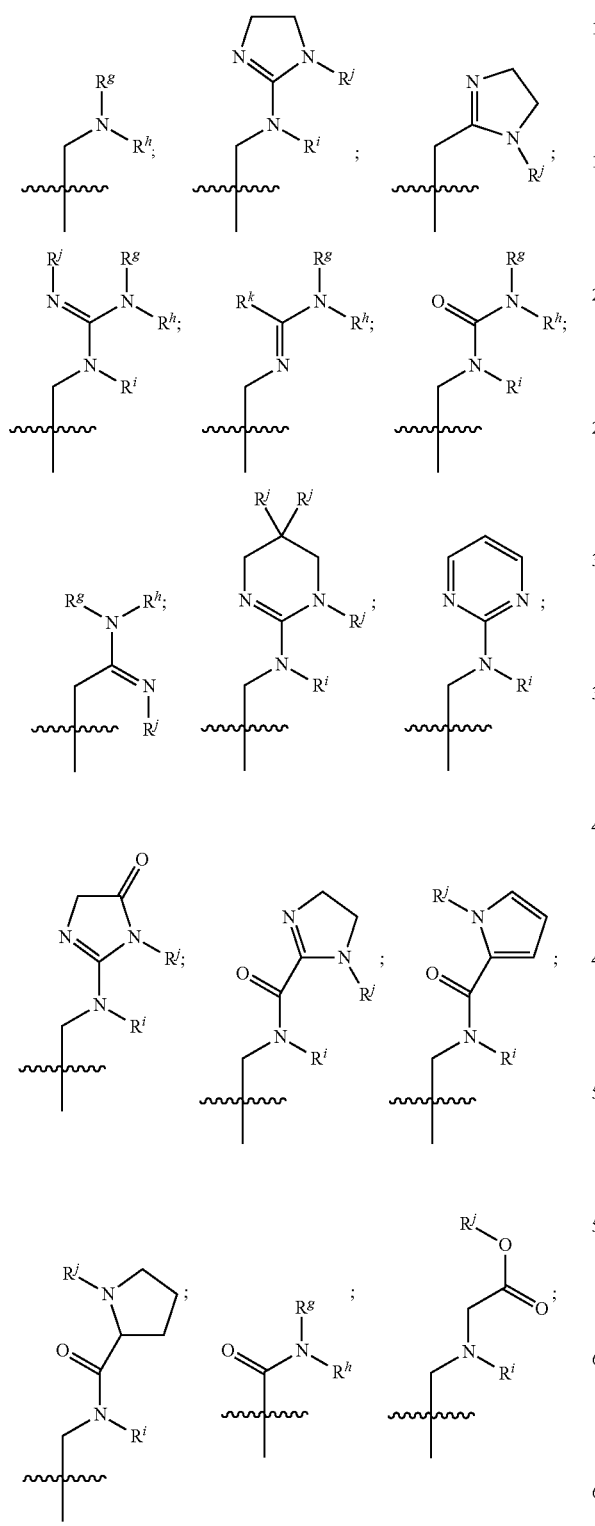
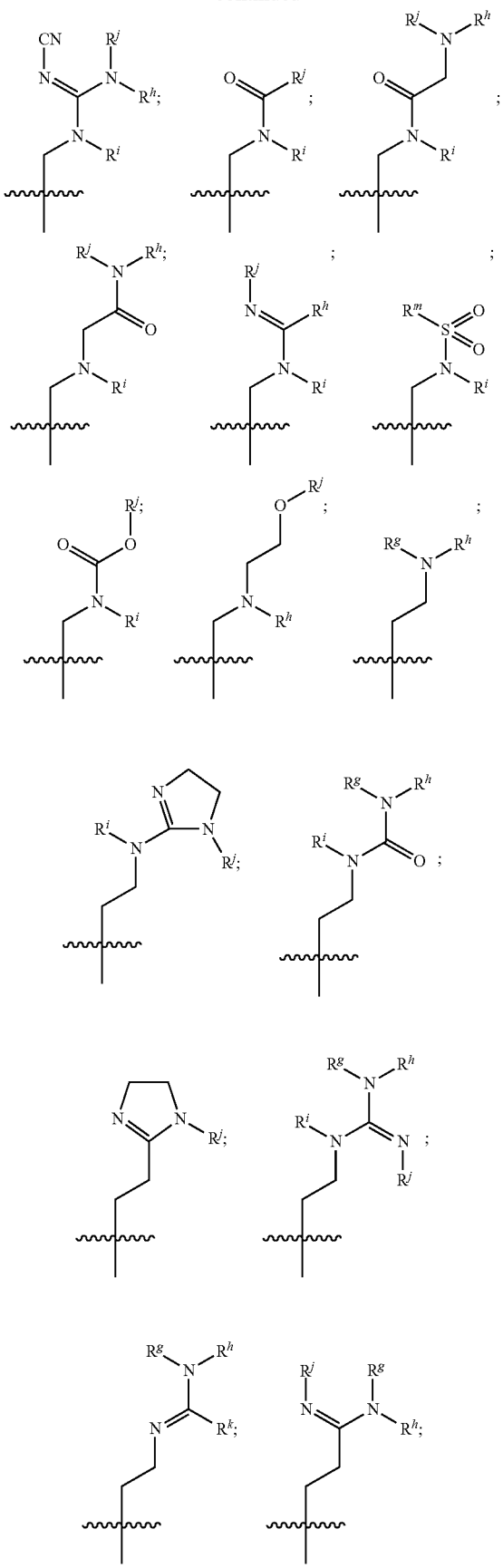

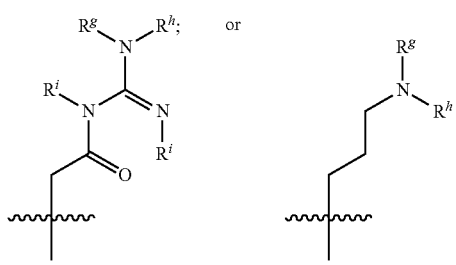

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or $-NR^hR^i$.

In certain embodiments of formula I, p is 2, q is 2, m is 0 or 1, and $R^2$ is:

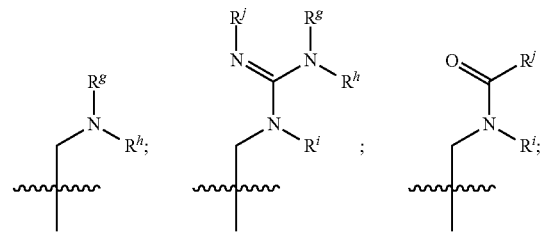

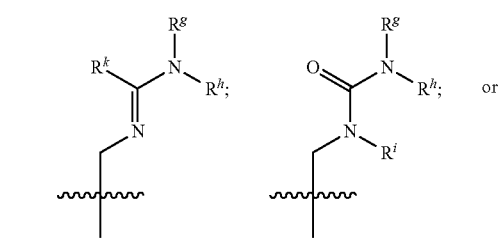

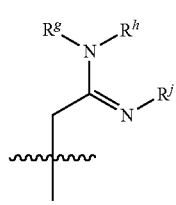

wherein $R^g$, $R^h$, $R^i$ and $R^j$ are hydrogen or alkyl.

In certain embodiments of formula I, p is 2, q is 2, m is 0 or 1, n is 1, $R^3$ and $R^4$ are hydrogen, one of $R^5$ and $R^6$ is hydrogen or alkyl, and the other is:

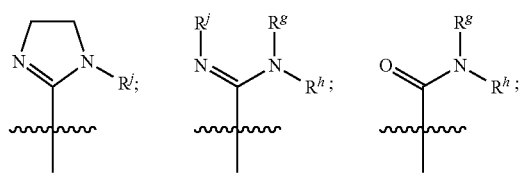

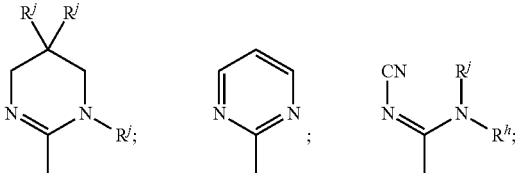

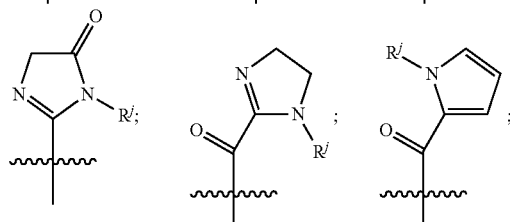

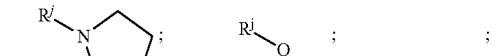
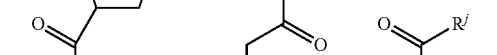
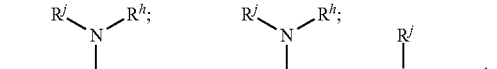
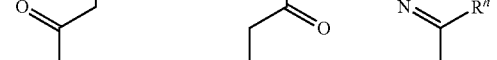
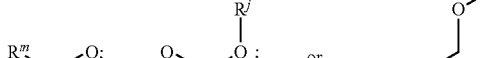

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or $-NR^hR^i$.

In certain embodiments of formula I, p is 2, q is 2, m is 0 or 1, n is 1, $R^3$ and $R^4$ are hydrogen, one of $R^5$ and $R^6$ is hydrogen or alkyl, and the other is:

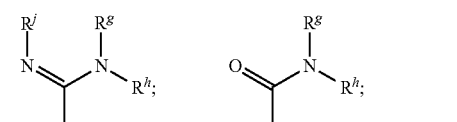

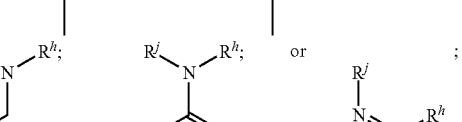

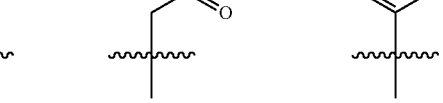

wherein $R^g$, $R^h$, $R^i$ and $R^j$ are hydrogen or alkyl.

In certain embodiments of formula I, p is 2, q is 2, m is 0 or 1, n is 1 or 2, and $R^3$ and $R^4$ together with the nitrogen to which they are attached form $=NR^f$ wherein $R^f$ is hydrogen, and wherein $R^5$ and $R^6$ are hydrogen.

In certain embodiments of formula I, p is 2, q is 2, m is 0 or 1, n is for 2, and $R^3$ and $R^4$ together with the nitrogen to which they are attached form $=O$.

In certain embodiments of formula I, p is 2, q is 2, m is 0 or 1, and n is 2.

In certain embodiments of formula I, p is 2, q is 2, m is 0 or 1, n is 2, and $R^3$ and $R^4$ are hydrogen.

In certain embodiments of formula I, p is 2, q is 2, m is 0 or 1, n is 2, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, p is 2, q is 2, m is 0 or 1, n is 2, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, p is 2, q is 2, m is 0 or 1, n is 2, $R^3$ and $R^4$ are hydrogen, one of $R^5$ and $R^6$ is hydrogen and the other is alkyl.

In certain embodiments of formula I, p is 2, q is 2, m is 0 or 1, n is 2, $R^3$ and $R^4$ are hydrogen, one of $R^5$ and $R^6$ is hydrogen or alkyl, and the other is:

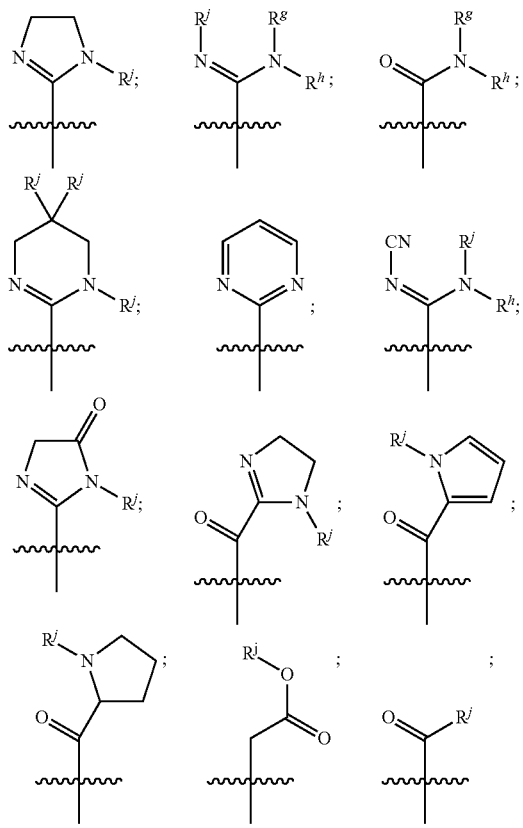

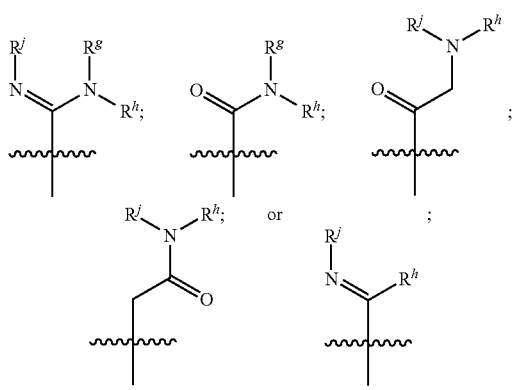

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or $-NR^hR^i$.

In certain embodiments of formula I, p is 2, q is 2, m is 0 or 1, n is 2, $R^3$ and $R^4$ are hydrogen, one of $R^5$ and $R^6$ is hydrogen or alkyl, and the other is:

wherein $R^g$, $R^h$, $R^i$ and $R^j$ are hydrogen or alkyl.

In certain embodiments of formula I, p is 2, q is 2, m is 0 or 1, and n is 3.

In certain embodiments of formula I, p is 2, q is 2, m is 0 or 1, n is 1, and $R^3$ and $R^4$ are hydrogen.

In certain embodiments of formula I, p is 2, q is 2, m is 0 or 1, n is 3, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, p is 2, q is 2, m is 0 or 1, n is 3, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, p is 2, q is 2, m is 0 or 1, n is 3, $R^3$ and $R^4$ are hydrogen, one of $R^5$ and $R^6$ is hydrogen or alkyl, and the other is:

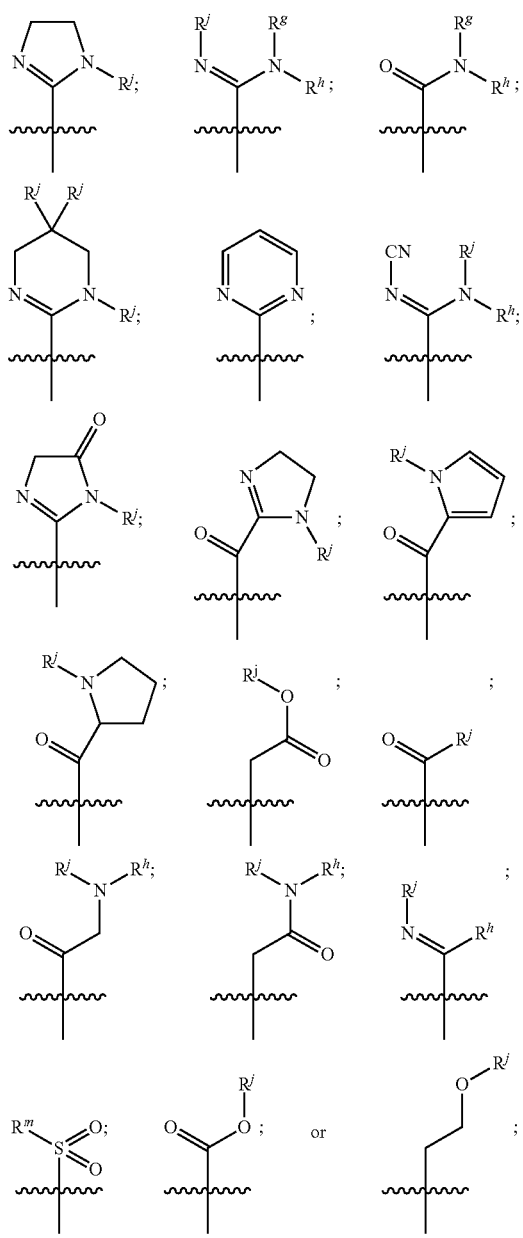

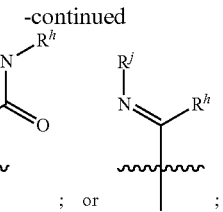

wherein $R^8$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula I, p is 2, q is 2, m is 0 or 1, n is 3, $R^3$ and $R^4$ are hydrogen, one of $R^5$ and $R^6$ is hydrogen or alkyl, and the other is:

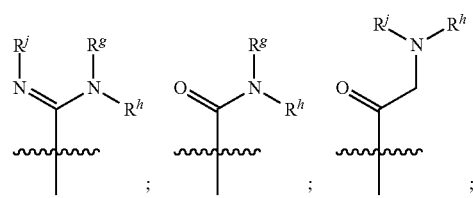

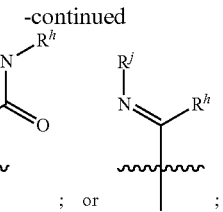

wherein $R^g$, $R^h$, $R^i$ and $R^j$ are hydrogen or alkyl.

In certain embodiments, the compounds of the invention may be of formula II:

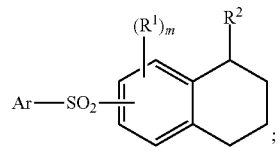

II wherein m, Ar, $R^1$ and $R^2$ are as defined herein.

In certain embodiments, the compounds of the invention may be of formula IIa:

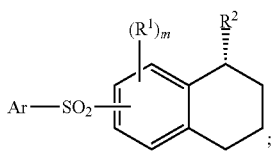

IIa wherein m, Ar, $R^1$ and $R^2$ are as defined herein.

In certain embodiments, the compounds of the invention may be of formula IIb:

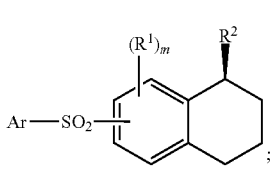

IIb wherein m, Ar, $R^1$ and $R^2$ are as defined herein.

In many embodiments of any of formulas II, IIa or IIb, m is 0 or 1.

In certain embodiments of any of formulas II, IIa or IIb, $R^1$ is halo.

In certain embodiments of any of formulas II, IIa or IIb, the group Ar—$SO_2$— is located at the 6- or 7-position of the tetralin ring system.

In certain embodiments of any of formulas II, IIa or IIb, the group Ar—$SO_2$— is located at the 6-position of the tetralin ring system.

In certain embodiments of any of formulas II, IIa or IIb, m is 0 or 1 and $R^1$ is located at the 8-position of the tetralin ring system.

In certain embodiments of any of formulas II, IIa or IIb, n is 1.

In certain embodiments of any of formulas II, IIa or IIb, n is 2.

In certain embodiments of any of formulas II, IIa or IIb, n is 3.

In certain embodiments of any of formulas II, IIa or IIb, $R^3$ and $R^4$ are hydrogen.

In certain embodiments of any of formulas II, IIa or IIb, one of $R^5$ and $R^6$ is hydrogen and the other is alkyl.

In certain embodiments of any of formulas II, IIa or IIb, $R^5$ and $R^6$ are hydrogen.

In certain embodiments of any of formulas II, IIa or IIb, one of $R^5$ and $R^6$ is hydrogen or alkyl and the other is: alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanooxamidinyl; alkylsulfonyl; hydroxyalkylcarbonyl; aminosulfonyl; hydroxyalkyl; or alkoxalkyl.

In certain embodiments of any of formulas II, IIa or IIb, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of any of formulas II, IIa or IIb, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of any of formulas II, IIa or IIb, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.

In certain embodiments of any of formulas II, IIa or IIb, one of $R^5$ and $R^6$ is hydrogen and the other is heteroaryl selected from pyrimidinyl, benzothiazol-2-yl, and 5,5-dimethyl-1,4,5,6-tetrahydropyrimidinyl.

In certain embodiments of any of formulas II, IIa or IIb, $R^5$ and $R^6$ together with the nitrogen to which they are attached form an amidinyl group.

In certain embodiments of any of formulas II, IIa or IIb, $R^5$ and $R^6$ together with the nitrogen to which they are attached form a guanidinyl group.

In certain embodiments of any of formulas II, IIa or IIb, $R^5$ and $R^6$ together with the nitrogen to which they are attached form a urea group.

In certain embodiments of any of formulas II, IIa or IIb, $R^3$ and $R^4$ together with the nitrogen to which they are attached form $=NR^f$ wherein $R^f$ is hydrogen.

In certain embodiments of any of formulas II, IIa or IIb, $R^3$ and $R^4$ together with the nitrogen to which they are attached form $=O$.

In certain embodiments of any of formulas II, IIa or IIb, one of $R^5$ and $R^6$ and one of $R^3$ and $R^4$ together with the atoms to which they are attached form an imidazolinyl ring.

In certain embodiments of any of formulas II, IIa or IIb, $R^5$ and $R^6$ together with the nitrogen to which they are attached form or a five- or six-membered heteroaryl ring that is optionally substituted and which optionally includes an additional nitrogen heteroatom.

In certain embodiments of any of formulas II, IIa or IIb, $R^5$ and $R^6$ together with the nitrogen to which they are attached form or a five- or six-membered heteroaryl ring selected from pyridinyl, pyrimidinyl, pyrrolyl, imidazolyl or pyrazolyl, each optionally substituted.

In certain embodiments of any of formulas II, IIa or IIb, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of any of formulas II, IIa or IIb, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of any of formulas II, IIa or IIb, Ar is optionally substituted phenyl.

In certain embodiments of any of formulas II, IIa or IIb, Ar is 2-halophenyl or 3-halopheny.

In certain embodiments of any of formulas II, IIa or IIb, Ar is heteroaryl.

In certain embodiments of any of formulas II, IIa or IIb, Ar is heteroaryl selected from indolyl, pyrrolyl, imidazolyl, pyrazolyl, benzimidazolyl, thienyl, furanyl, pyridinyl and pyrimidinyl, each optionally substituted.

In certain embodiments of any of formulas II, IIa or IIb, Ar is heteroaryl selected from indolyl, pyrrolyl, imidazolyl, pyrazolyl, and benzimidazolyl, each optionally substituted.

In certain embodiments of any of formulas II, IIa or IIb, Ar is heteroaryl selected from indol-3-yl, pyrrol-3-yl, 1-methylimidazol-2-yl, imidazol-2-yl, pyrazol-4-yl, benzimidazol-4-yl, 6-fluoroindol-3-yl, 1-methylpyrrol-3-yl and 6-fluorobenzimidazol-4-yl.

In certain embodiments of any of formulas II, IIa or IIb, one of $R^5$ and $R^6$ and one of $R^3$ and $R^4$ together with the atoms to which they are attached form an imidazolinyl ring.

In certain embodiments of any of formulas II, IIa or IIb, m is 0 or 1, and n is 1.

In certain embodiments of any of formulas II, IIa or IIb, m is 0 or 1, n is 1, and $R^3$ and $R^4$ are hydrogen.

In certain embodiments of any of formulas II, IIa or IIb, m is 0 or 1, n is 1, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of any of formulas II, IIa or IIb, m is 0 or 1, n is 1, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of any of formulas II, IIa or IIb, m is 0 or 1, n is 1, $R^3$ and $R^4$ are hydrogen, one of $R^5$ and $R^6$ is hydrogen and the other is alkyl.

In certain embodiments of any of formulas II, IIa or IIb, m is 0 or 1, and $R^2$ is: aminoalkyl; alkylaminoalkyl; dialkylaminoalkyl; imidazolinylaminoalkyl; imidazolinylalkyl, guanidinylalkyl; tetrahydropyrimidinylaminoalkyl; amidinylalkyl; urealkyl; amidinyl; heteroarylaminoalkyl; imidazolylaminoalkyl; guanidinylcarbonylalkyl; imidazolonylaminoalkyl; imidazolinylcarbonylaminoalkyl; aminocarbonylalkyl; pyrrolylcarbonylaminoalkyl; aminoalkylcarbonylaminoalkyl; alkoxycarbonylalkylaminoalkyl; N-cyanoguanidinylalkyl; alkylcarbonylaminoalkyl; aminocarbonylalkylaminoalkyl; pyrrolidinylcarbonylaminoalkyl; alkylsulfonamidoalkyl; aminosulfonamidoalkyl; alkoxycarbonylaminoalkyl; hydroxyalkylcarbonylaminoalkyl; hydroxyalkylaminoalkyl; alkoxyalkylaminoalkyl; or alkylsulfonylalkylaminoalkyl.

In certain embodiments of any of formulas II, IIa or IIb, m is 0 or 1, and $R^2$ is: aminoalkyl; alkylaminoalkyl; dialkylaminoalkyl; guanidinylalkyl; amidinylalkyl; urealkyl; amidinyl; guanidinylcarbonylalkyl; aminocarbonylalkyl; aminoalkylcarbonylaminoalkyl; alkylcarbonylaminoalkyl; aminocarbonylalkylaminoalkyl; or alkoxycarbonylaminoalkyl.

In certain embodiments of any of formulas II, IIa or IIb, m is 0 or 1, and $R^2$ is:

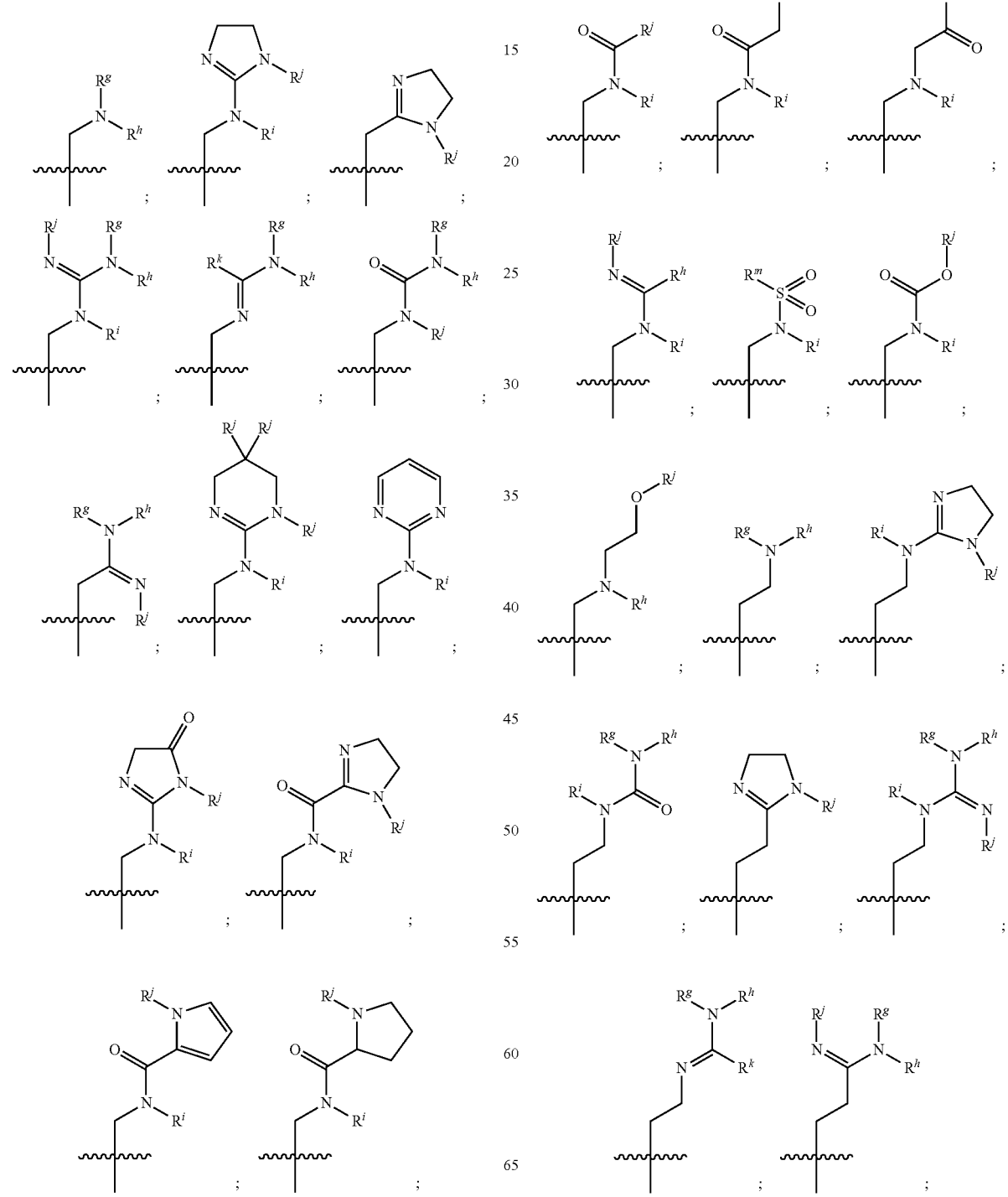

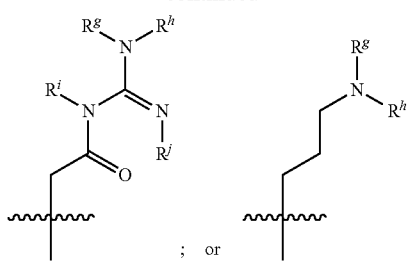

; or wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of any of formulas II, IIa or IIb, m is 0 or 1, and $R^2$ is:

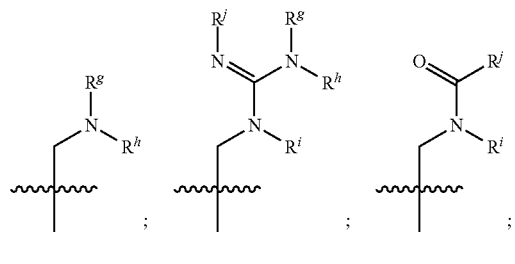

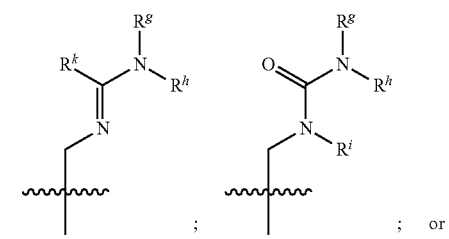

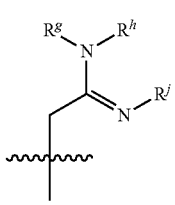

wherein $R^g$, $R^h$, $R^i$ and $R^j$ are hydrogen or alkyl.

In certain embodiments of any of formulas II, IIa or IIb, m is 0 or 1, n is 1, $R^3$ and $R^4$ are hydrogen, one of $R^5$ and $R^6$ is hydrogen or alkyl, and the other is:

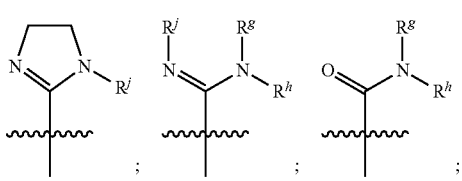

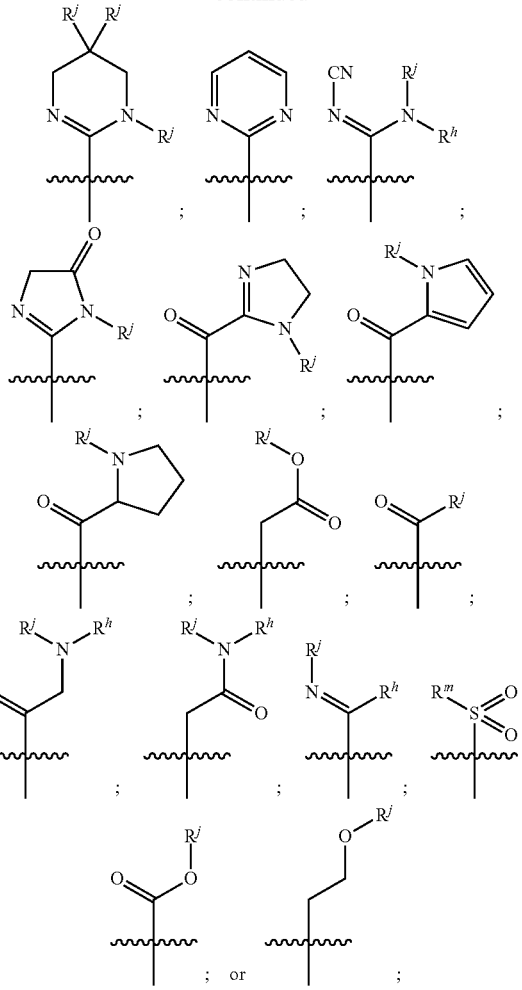

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of any of formulas II, IIa or IIb, m is 0 or 1, n is 1, $R^3$ and $R^4$ are hydrogen, one of $R^5$ and $R^6$ is hydrogen or alkyl, and the other is:

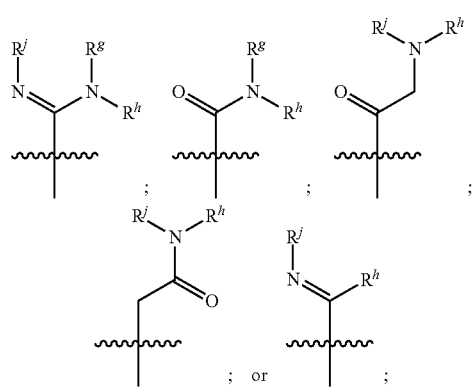

wherein $R^g$, $R^h$, $R^i$ and $R^j$ are hydrogen or alkyl.

In certain embodiments of any of formulas II, IIa or IIb, m is 0 or 1, n is 1 or 2, and $R^3$ and $R^4$ together with the nitrogen to which they are attached form =NR$^f$ wherein R$^f$ is hydrogen, and wherein R$^5$ and R$^6$ are hydrogen.

In certain embodiments of any of formulas II, IIa or IIb, m is 0 or 1, n is 1 or 2, and R$^3$ and R$^4$ together with the nitrogen to which they are attached form =O.

In certain embodiments of any of formulas II, IIa or IIb, m is 0 or 1, and n is 2.

In certain embodiments of any of formulas II, IIa or IIb, m is 0 or 1, n is 2, and R$^3$ and R$^4$ are hydrogen.

In certain embodiments of any of formulas II, IIa or IIb, m is 0 or 1, n is 2, R$^3$ and R$^4$ are hydrogen, one of R$^5$ and R$^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of any of formulas II, IIa or IIb, m is 0 or 1, n is 2, R$^3$ and R$^4$ are hydrogen, one of R$^5$ and R$^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of any of formulas II, IIa or IIb, m is 0 or 1, n is 2, R$^3$ and R$^4$ are hydrogen, one of R$^5$ and R$^6$ is hydrogen and the other is alkyl.

In certain embodiments of any of formulas II, IIa or IIb, m is 0 or 1, n is 2, R$^3$ and R$^4$ are hydrogen, one of R$^5$ and R$^6$ is hydrogen or alkyl, and the other is:

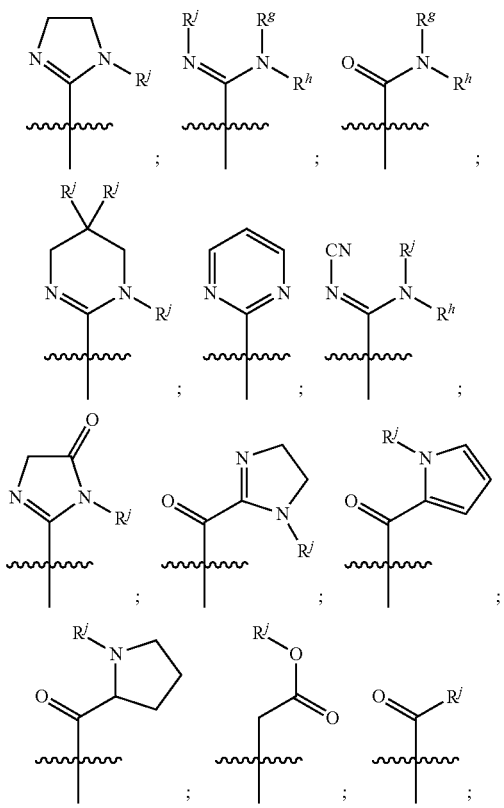

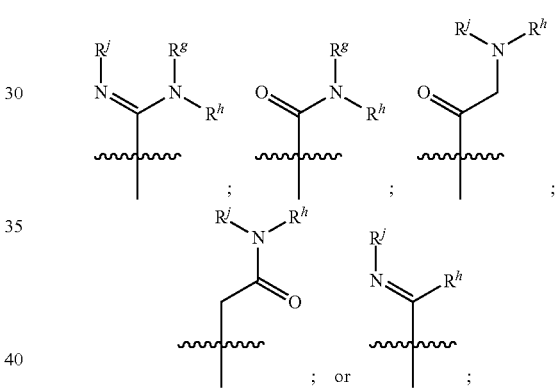

wherein R$^g$ is hydrogen, alkyl, optionally substituted phenyl or optionally substituted pyrimidinyl, R$^h$, R$^i$, R$^j$ and R$^k$ in each independent occurrence is hydrogen or alkyl, and R$^m$ is hydrogen, alkyl or —NR$^h$R$^i$.

In certain embodiments of any of formulas II, IIa or IIb, m is 0 or 1, n is 2, R$^3$ and R$^4$ are hydrogen, one of R$^5$ and R$^6$ is hydrogen or alkyl, and the other is:

wherein R$^g$, R$^h$, R$^i$ and R$^j$ are hydrogen or alkyl.

In certain embodiments of any of formulas II, IIa or IIb, m is 0 or 1, and n is 3.

In certain embodiments of any of formulas II, IIa or IIb, m is 0 or 1, n is 1, and R$^3$ and R$^4$ are hydrogen.

In certain embodiments of any of formulas II, IIa or IIb, p is 2, q is 2, m is 0 or 1, n is 3, R$^3$ and R$^4$ are hydrogen, one of R$^5$ and R$^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of any of formulas II, IIa or IIb, p is 2, q is 2, m is 0 or 1, n is 3, R$^3$ and R$^4$ are hydrogen, one of R$^5$ and R$^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of any of formulas II, IIa or IIb, p is 2, q is 2, m is 0 or 1, n is 3, R$^3$ and R$^4$ are hydrogen, one of R$^5$ and R$^6$ is hydrogen or alkyl, and the other is:

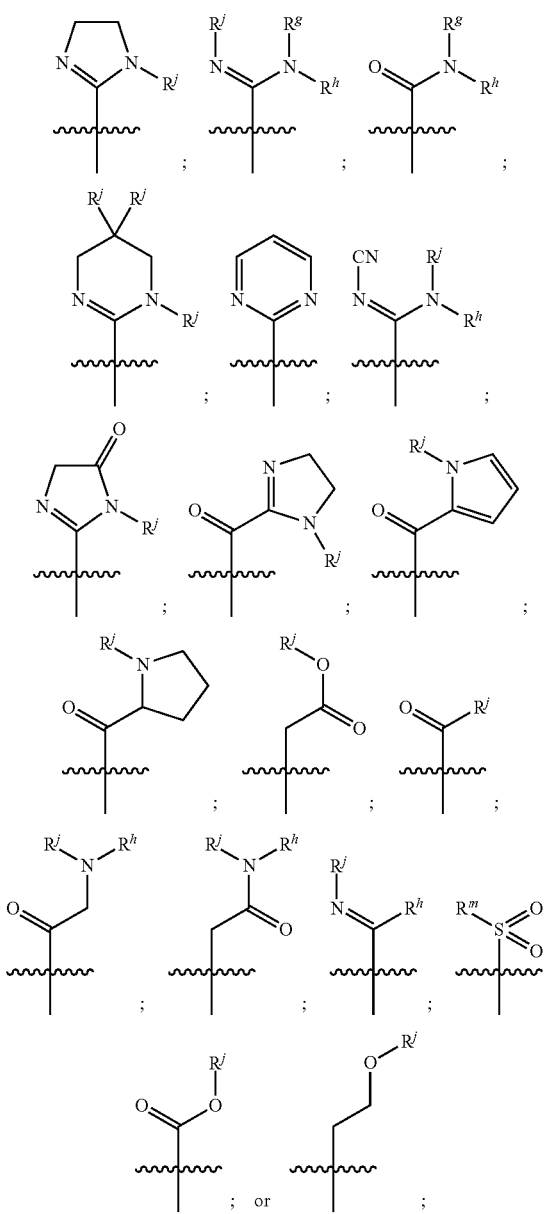

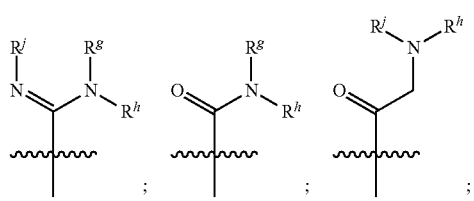

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of any of formulas II, IIa or IIb, p is 2, q is 2, m is 0 or 1, n is 3, $R^3$ and $R^4$ are hydrogen, one of $R^5$ and $R^6$ is hydrogen or alkyl, and the other is:

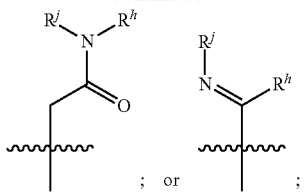

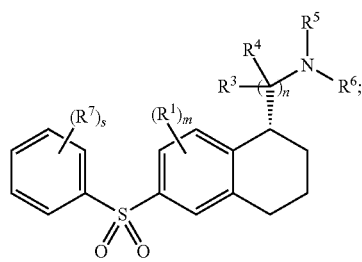

wherein $R^g$, $R^h$, $R^i$ and $R^j$ are hydrogen or alkyl.

In certain embodiments of the invention, the subject compounds may be of the formula IIIa:

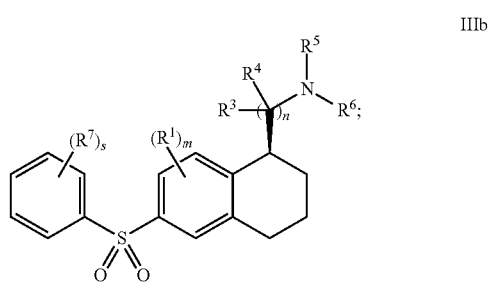

wherein:

s is from 0 to 4;

each $R^7$ is independently halo, alkyl, alkoxy, haloalkyl, heteroalkyl, cyano, —S(O)$_r R^a$, —C(=O)—$NR^bR^c$, —SO$_2$—$NR^bR^c$, —N($R^d$)—C(=O)—$R^e$, or —C(=O)—$R^e$, where r is from 0 to 2, $R^a$, $R^b$, $R^c$ and $R^d$ each independently is hydrogen or alkyl, and $R^e$ is hydrogen, alkyl, alkoxy or hydroxy; and m, n, $R^1$, $R^3$, $R^4$, $R^5$ and $R^6$ are as defined herein.

In certain embodiments of the invention, the subject compounds may be of the formula IIIb:

IIIb wherein:

s is from 0 to 4;

each $R^7$ is independently halo, alkyl, alkoxy, haloalkyl, heteroalkyl, cyano, —S(O)$_r R^a$, —C(=O)—$NR^bR^c$, —SO$_2$—$NR^bR^c$, —N($R^d$)—C(=O)—$R^e$, or —C(=O)—$R^e$, where r is from 0 to 2, $R^a$, $R^b$, $R^c$ and $R^d$ each independently is hydrogen or alkyl, and $R^e$ is hydrogen, alkyl, alkoxy or hydroxy; and m, n, $R^1$, $R^3$, $R^4$, $R^5$ and $R^6$ are as defined herein.

In certain embodiments of the invention, the subject compounds may be of the formula IIIc:

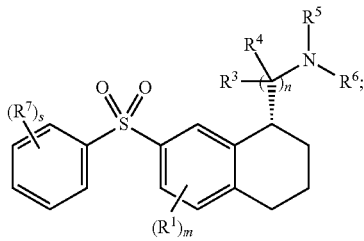

wherein:

s is from 0 to 4;

each $R^7$ is independently halo, alkyl, alkoxy, hydroxy, haloalkyl, heteroalkyl, cyano, —S(O)$_r$R$^a$, —C(=O)—NR$^b$R$^c$, —SO$_2$—NR$^b$R$^c$, —N(R$^d$)—C(=O)—R$^e$, or —C(=O)—R$^e$, where r is from 0 to 2, R$^a$, R$^b$, R$^c$ and R$^d$ each independently is hydrogen or alkyl, and R$^e$ is hydrogen, alkyl, alkoxy or hydroxy; and m, n, $R^1$, $R^3$, $R^4$, $R^5$ and $R^6$ are as defined herein.

In certain embodiments of the invention, the subject compounds may be of the formula IIId:

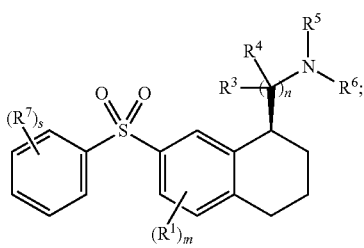

wherein:

s is from 0 to 4;

each $R^7$ is independently halo, alkyl, alkoxy, hydroxy, haloalkyl, heteroalkyl, cyano, —S(O)$_r$R$^a$, —C(=O)—NR$^b$R$^c$, —SO$_2$—NR$^b$R$^c$, —N(R$^d$)—C(=O)—R$^e$, or —C(=O)—R$^e$, where r is from 0 to 2, R$^a$, R$^b$, R$^c$ and R$^d$ each independently is hydrogen or alkyl, and R$^e$ is hydrogen, alkyl, alkoxy or hydroxy; and m, n, $R^1$, $R^3$, $R^4$, $R^5$ and $R^6$ are as defined herein.

In many embodiments of any of formulas IIIa, IIIb, IIIc or IIId, m is 0 or 1.

In certain embodiments of any of formulas IIIa, IIIb, IIIc or IIId, $R^1$ is halo.

In certain embodiments of any of formulas IIIa, IIIb, IIIc or IIId, m is 0 or 1 and $R^1$ is located at the 8-position of the tetralin ring system.

In certain embodiments of any of formulas IIIa, IIIb, IIIc or IIId, n is 1.

In certain embodiments of any of formulas IIIa, IIIb, IIIc or IIId, n is 2.

In certain embodiments of any of formulas IIIa, IIIb, IIIc or IIId, n is 3.

In certain embodiments of any of formulas IIIa, IIIb, IIIc or IIId, $R^3$ and $R^4$ are hydrogen.

In certain embodiments of any of formulas IIIa, IIIb, IIIc or IIId, one of $R^5$ and $R^6$ is hydrogen and the other is alkyl.

In certain embodiments of any of formulas IIIa, IIIb, IIIc or IIId, $R^5$ and $R^6$ are hydrogen.

In certain embodiments of any of formulas IIIa, IIIb, IIIc or IIId, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; or alkoxalkyl.

In certain embodiments of any of formulas IIIa, IIIb, IIIc or IIId, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of any of formulas IIIa, IIIb, IIIc or IIId, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of any of formulas IIIa, IIIb, IIIc or IIId, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.

In certain embodiments of any of formulas IIIa, IIIb, IIIc or IIId, one of $R^5$ and $R^6$ is hydrogen and the other is heteroaryl selected from pyrimidinyl, benzothiazol-2-yl, and 5,5-dimethyl-1,4,5,6-tetrahydropyrimidinyl.

In certain embodiments of any of formulas IIIa, IIIb, IIIc or IIId, $R^5$ and $R^6$ together with the nitrogen to which they are attached form an amidinyl group.

In certain embodiments of any of formulas IIIa, IIIb, IIIc or IIId, $R^5$ and $R^6$ together with the nitrogen to which they are attached form a guanidinyl group.

In certain embodiments of any of formulas IIIa, IIIb, IIIc or IIId, $R^5$ and $R^6$ together with the nitrogen to which they are attached form a urea group.

In certain embodiments of any of formulas IIIa, IIIb, IIIc or IIId, $R^3$ and $R^4$ together with the nitrogen to which they are attached form =NR$^f$ wherein R$^f$ is hydrogen.

In certain embodiments of any of formulas IIIa, IIIb, IIIc or IIId, $R^3$ and $R^4$ together with the nitrogen to which they are attached form =O.

In certain embodiments of any of formulas IIIa, IIIb, IIIc or IIId, one of $R^5$ and $R^6$ and one of $R^3$ and $R^4$ together with the atoms to which they are attached form an imidazolinyl ring.

In certain embodiments of either of formula IIIa or IIIb, $R^5$ and $R^6$ together with the nitrogen to which they are attached form or a five- or six-membered heteroaryl ring that is optionally substituted and which optionally includes an additional nitrogen heteroatom.

In certain embodiments of any of formulas IIIa, IIIb, IIIc or IIId, $R^5$ and $R^6$ together with the nitrogen to which they are attached form or a five- or six-membered heteroaryl ring selected from pyridinyl, pyrimidinyl, pyrrolyl, imidazolyl or pyrazolyl, each optionally substituted.

In certain embodiments of any of formulas IIIa, IIIb, IIIc or IIId, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of any of formulas IIIa, IIIb, IIIc or IIId, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of either of formula IIIa or IIIb, one of $R^5$ and $R^6$ and one of $R^3$ and $R^4$ together with the atoms to which they are attached form an imidazolinyl ring.

In certain embodiments of either of formula IIIa or IIIb, s is from 0 to 2 and $R^7$ is halo, alkyl, alkoxy, haloalkyl, hydroxy, cyano or methanesulfonyl.

In certain embodiments of either of formula IIIa or IIIb, s is 0 or 1 and $R^7$ is halo.

In certain embodiments of any of formulas IIIa, IIIb, IIIc or IIId, m is 0 or 1, and n is 1.

In certain embodiments of any of formulas IIIa, IIIb, IIIc or IIId, m is 0 or 1, n is 1, and $R^3$ and $R^4$ are hydrogen.

In certain embodiments of any of formulas IIIa, IIIb, IIIc or IIId, m is 0 or 1, n is 1, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of any of formulas IIIc, IIIb, IIIc or IIId, m is 0 or 1, n is 1, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of any of formulas IIIa, IIIb, IIIc or IIId, m is 0 or 1, n is 1, $R^3$ and $R^4$ are hydrogen, one of $R^5$ and $R^6$ is hydrogen and the other is alkyl.

In certain embodiments of any of formulas IIIa, IIIb, IIIc or IIId, m is 0 of 1, n is 1, $R^3$ and $R^4$ are hydrogen, one of $R^5$ and $R^6$ is hydrogen or alkyl, and the other is:

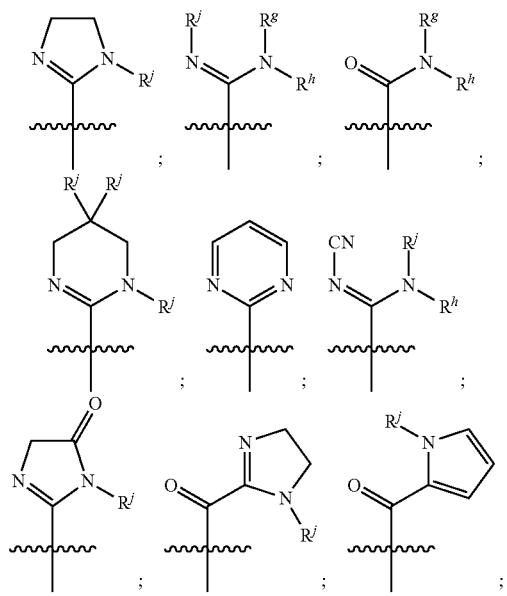

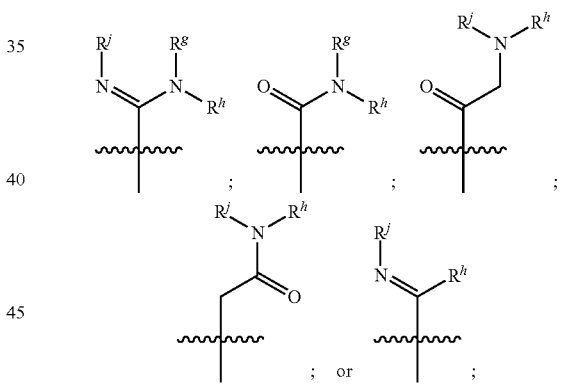

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or $-NR^hR^i$.

In certain embodiments of any of formulas IIIa, IIIb, IIIc or IIId, m is 0 or 1, n is 1, $R^3$ and $R^4$ are hydrogen, one of $R^5$ and $R^6$ is hydrogen or alkyl, and the other is:

wherein $R^g$, $R^h$, $R^i$ and $R^j$ are hydrogen or alkyl.

In certain embodiments of any of formulas IIIa, IIIb, IIIc or IIId, m is 0 or 1, n is 1 or 2, and $R^3$ and $R^4$ together with the nitrogen to which they are attached form $=NR^f$ wherein $R^f$ is hydrogen, and wherein $R^5$ and $R^6$ are hydrogen.

In certain embodiments of any of formulas IIIa, IIIb, IIIc or IIId, m is 0 or 1, n is 1 or 2, and $R^3$ and $R^4$ together with the nitrogen to which they are attached form $=O$.

In certain embodiments of any of formulas IIIa, IIIb, IIIc or IIId, m is 0 or 1, and n is 2.

In certain embodiments of any of formulas IIIa, IIIb, IIIc or IIId, m is 0 or 1, n is 2, and $R^3$ and $R^4$ are hydrogen.

In certain embodiments of either of formula IIIa or IIIb, m is 0 or 1, n is 2, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of any of formulas IIIa, IIIb, IIIc or IIId, m is 0 or 1, n is 2, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of any of formulas IIIa, IIIb, IIIc or IIId, m is 0 or 1, n is 2, $R^3$ and $R^4$ are hydrogen, one of $R^5$ and $R^6$ is hydrogen and the other is alkyl.

In certain embodiments of any of formulas IIIa, IIIb, IIIc or IIId, m is 0 or 1, n is 2, $R^3$ and $R^4$ are hydrogen, one of $R^5$ and $R^6$ is hydrogen or alkyl, and the other is:

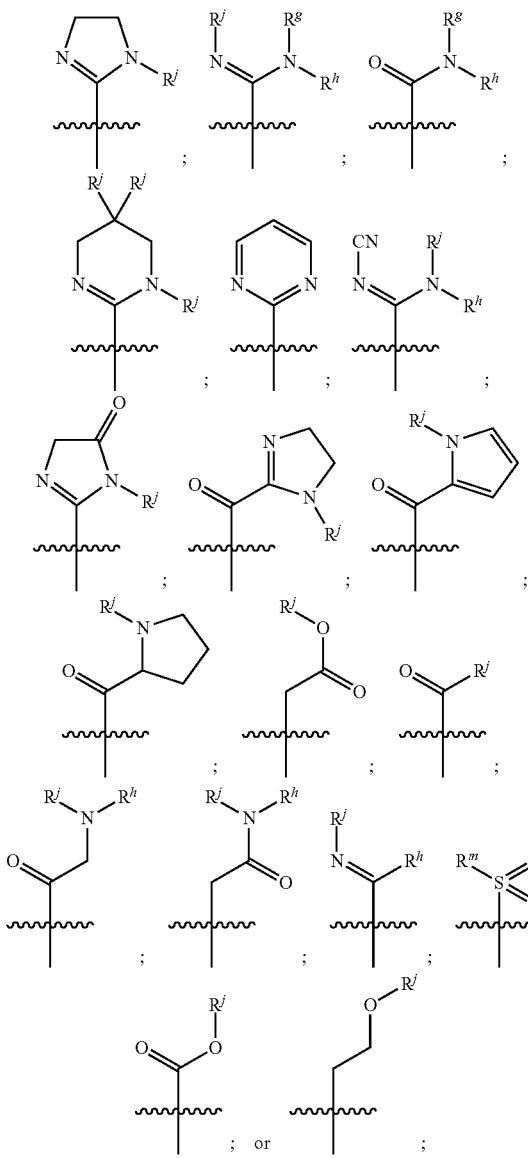

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of any of formulas IIIa, IIIb, IIIc or IIId, m is 0 or 1, n is 2, $R^3$ and $R^4$ are hydrogen, one of $R^5$ and $R^6$ is hydrogen or alkyl, and the other is:

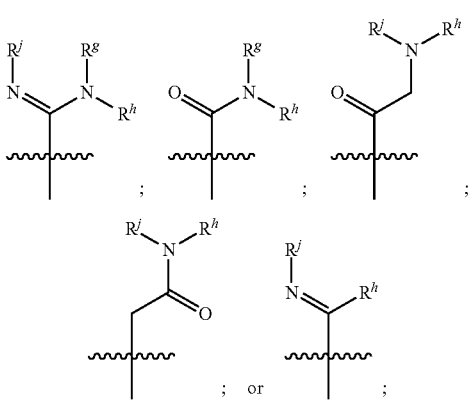

wherein $R^g$, $R^h$, $R^i$ and $R^j$ are hydrogen or alkyl.

In certain embodiments of any of formulas IIIa, IIIb, IIIc or IIId, m is 0 or 1, and n is 3.

In certain embodiments of any of formulas IIIa, IIIb, IIIc or IIId, m is 0 or 1, n is 1, and $R^3$ and $R^4$ are hydrogen.

In certain embodiments of any of formulas IIIa, IIIb, IIIc or IIId, p is 2, q is 2, m is 0 or 1, n is 3, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbdnyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of any of formulas IIIa, IIIb, IIIc or IIId, p is 2, q is 2, m is 0 or 1, n is 3, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of any of formulas IIIa, IIIb, IIIc or IIId, p is 2, q is 2, m is 0 or 1, n is 3, $R^3$ and $R^4$ are hydrogen, one of $R^5$ and $R^6$ is hydrogen or alkyl, and the other is:

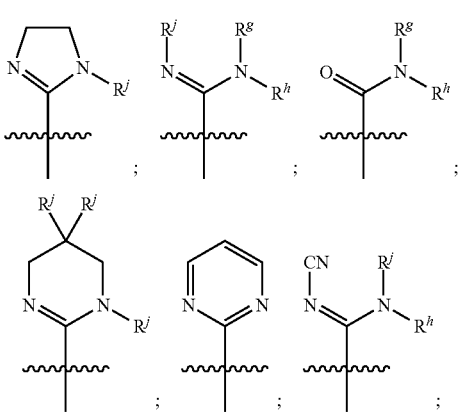

39
-continued

[Chemical structures shown: imidazolone with R^j; dihydroimidazole with R^j; pyrrole with R^j; pyrrolidinyl carbonyl with R^j; ester with R^j; ester with R^j]

[Chemical structures shown: aminomethyl carbonyl with R^j, R^h; aminoethyl carbonyl with R^j, R^h; amidine with R^j, R^h; sulfonyl with R^m]

[Chemical structures shown: carbonate with R^j; ether with R^j]

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^h R^i$.

In certain embodiments of any of formulas IIIa, IIIb, IIIc or IIId, p is 2, q is 2, m is 0 or 1, n is 3, $R^3$ and $R^4$ are hydrogen, one of $R^5$ and $R^6$ is hydrogen or alkyl, and the other is:

[Chemical structures shown: guanidinyl with R^j, R^g, R^h; amide with R^g, R^h; aminomethyl with R^j, R^h; amide with R^j, R^h; amidine with R^j, R^h]

wherein $R^g$, $R^h$, $R^i$ and $R^j$ are hydrogen or alkyl.

40

The subject compounds may, in certain embodiments, be more specifically of formula IVa:

IVa

[Chemical structure of tetralin with sulfonyl-phenyl and aminomethyl substituents, showing $R^5$, $R^6$, $(R^1)_m$, $(R^7)_s$, and n]

wherein m, n, s, $R^1$, $R^5$, $R^6$ and $R^7$ are as defined herein.

The subject compounds may, in certain embodiments, be more specifically of formula IVb:

IVb

[Chemical structure of tetralin with sulfonyl-phenyl and aminomethyl substituents, showing $R^5$, $R^6$, $(R^1)_m$, $(R^7)_s$, and n]

wherein m, n, s, $R^1$, $R^5$, $R^6$ and $R^7$ are as defined herein.

In many embodiments of either of formula IVa or formula IVb, m is 0 or 1.

In certain embodiments of either of formula IVa or formula IVb, $R^1$ is halo.

In certain embodiments of either of formula IVa or formula IVb, m is 0 or 1 and $R^1$ is located at the 8-position of the tetralin ring system.

In certain embodiments of either of formula IVa or formula IVb, n is 1.

In certain embodiments of either of formula IVa or formula IVb, n is 2.

In certain embodiments of either of formula IVa or formula IVb, n is 3.

In certain embodiments of either of formula IVa or formula IVb, one of $R^5$ and $R^6$ is hydrogen and the other is alkyl.

In certain embodiments of either of formula IVa or formula IVb, $R^5$ and $R^6$ are hydrogen.

In certain embodiments of either of formula IVa or formula IVb, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; or alkoxalkyl.

In certain embodiments of either of formula IVa or formula IVb, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of either of formula IVa or formula IVb, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of either of formula IVa or formula IVb, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.

In certain embodiments of either of formula IVa or formula IVb, one of $R^5$ and $R^6$ is hydrogen and the other is heteroaryl selected from pyrimidinyl, benzothiazol-2-yl, and 5,5-dimethyl-1,4,5,6-tetrahydropyrimidinyl.

In certain embodiments of either of formula IVa or formula IVb, $R^5$ and $R^6$ together with the nitrogen to which they are attached form an amidinyl group.

In certain embodiments of either of formula IVa or formula IVb, $R^5$ and $R^6$ together with the nitrogen to which they are attached form a guanidinyl group.

In certain embodiments of either of formula IVa or formula IVb, $R^5$ and $R^6$ together with the nitrogen to which they are attached form a urea group.

In certain embodiments of either of formula IVa or formula IVb, $R^5$ and $R^6$ together with the nitrogen to which they are attached form or a five- or six-membered heteroaryl ring that is optionally substituted and which optionally includes an additional nitrogen heteroatom.

In certain embodiments of either of formula IVa or formula IVb, $R^5$ and $R^6$ together with the nitrogen to which they are attached form or a five- or six-membered heteroaryl ring selected from pyridinyl, pyrimidinyl, pyrrolyl, imidazolyl or pyrazolyl, each optionally substituted.

In certain embodiments of either of formula IVa or formula IVb, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of either of formula IVa or formula IVb, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of either of formula IVa or formula IVb, one of $R^5$ and $R^6$ and one of $R^3$ and $R^4$ together with the atoms to which they are attached form an imidazolinyl ring.

In certain embodiments of either of formula IVa or, formula IVb, s is from 0 to 2 and $R^7$ is halo, alkyl, alkoxy, haloalkyl, hydroxy, cyano or methanesulfonyl.

In certain embodiments of either of formula IVa or formula IVb, s is 0 or 1 and $R^7$ is halo.

In certain embodiments of either of formula IVa or formula IVb, m is 0 or 1, and n is 1.

In certain embodiments of either of formula IVa or formula IVb, m is 0 or 1, n is 1, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of either of formula IVa or formula IVb, m is 0 or 1, n is 1, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of either of formula IVa or formula IVb, m is 0 or 1, n is 1, one of $R^5$ and $R^6$ is hydrogen and the other is alkyl.

In certain embodiments of either of formula IVa or formula IVb, m is 0 or 1, n is 1, one of $R^5$ and $R^6$ is hydrogen or alkyl, and the other is:

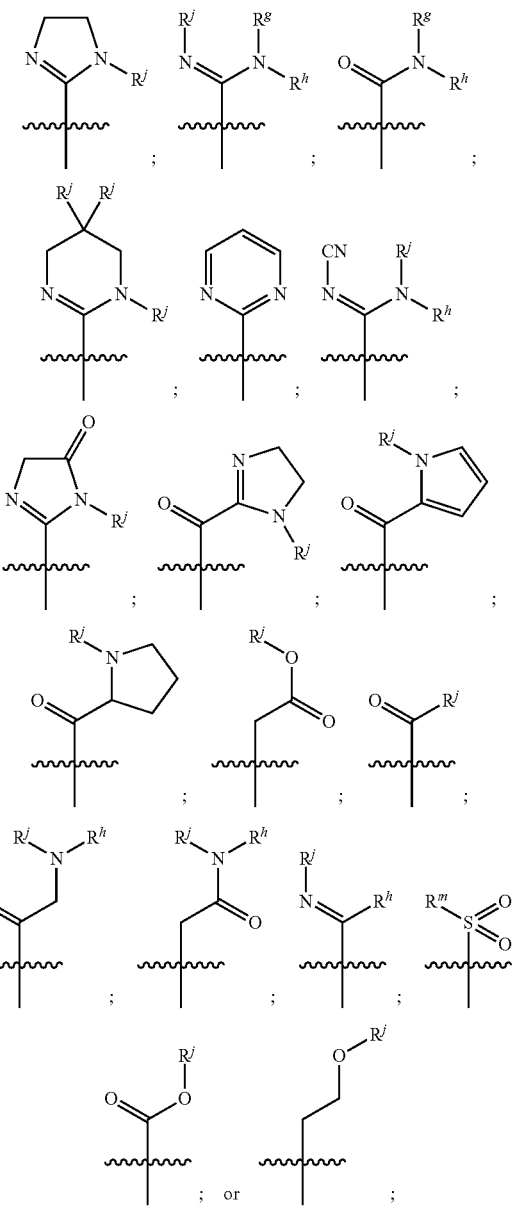

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of either of formula IVa or formula IVb, m is 0 or 1, n is 1, $R^3$ and $R^4$ are hydrogen, one of $R^5$ and $R^6$ is hydrogen or alkyl, and the other is:

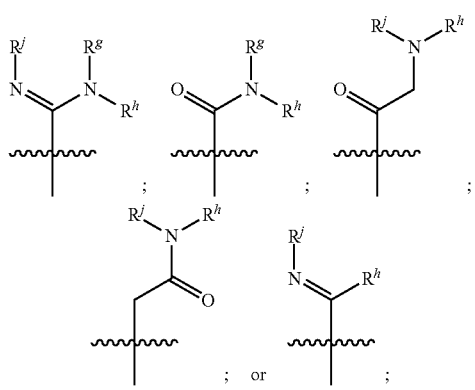

wherein $R^g$, $R^h$, $R^i$ and $R^j$ are hydrogen or alkyl.

In certain embodiments of either of formula IVa or formula IVb, m is 0 or 1, and n is 2.

In certain embodiments of either of formula IIIa or IIIb, m is 0 or 1, n is 2, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of either of formula IVa or formula IVb, m is 0 or 1, n is 2, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of either of formula IVa or formula IVb, m is 0 or 1, n is 2, one of $R^5$ and $R^6$ is hydrogen and the other is alkyl.

In certain embodiments of either of formula IVa or formula IVb, m is 0 or 1, n is 2, one of $R^5$ and $R^6$ is hydrogen or alkyl, and the other is:

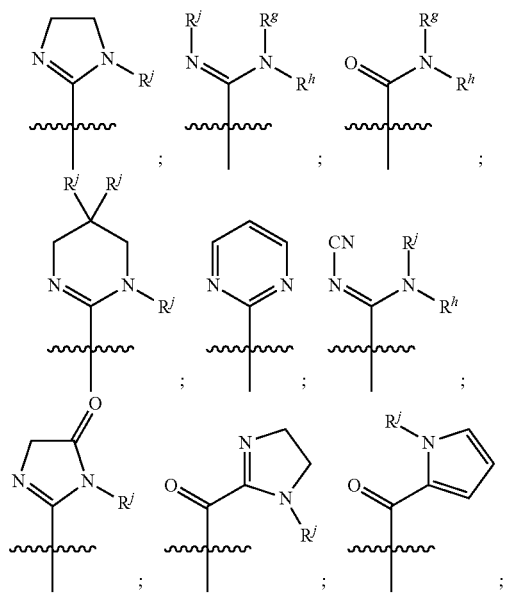

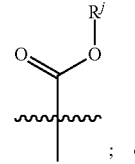

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or $-NR^hR^i$.

In certain embodiments of either of formula IVa or formula IVb, m is 0 or 1, n is 2, one of $R^5$ and $R^6$ is hydrogen or alkyl, and the other is:

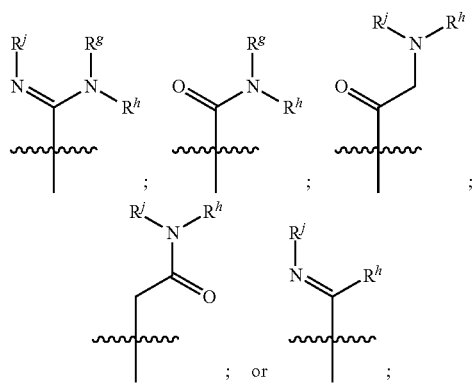

wherein $R^g$, $R^h$, $R^i$ and $R^j$ are hydrogen or alkyl.

In certain embodiments of either of formula IVa or formula IVb, m is 0 or 1, and n is 3.

In certain embodiments of either of formula IVa or formula IVb, p is 2, q is 2, m is 0 or 1, n is 3, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of either of formula IVa or formula IVb, p is 2, q is 2, m is 0 or 1, n is 3, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of either of formula IVa or formula IVb, p is 2, q is 2, m is 0 or 1, n is 3, one of $R^5$ and $R^6$ is hydrogen or alkyl, and the other is:

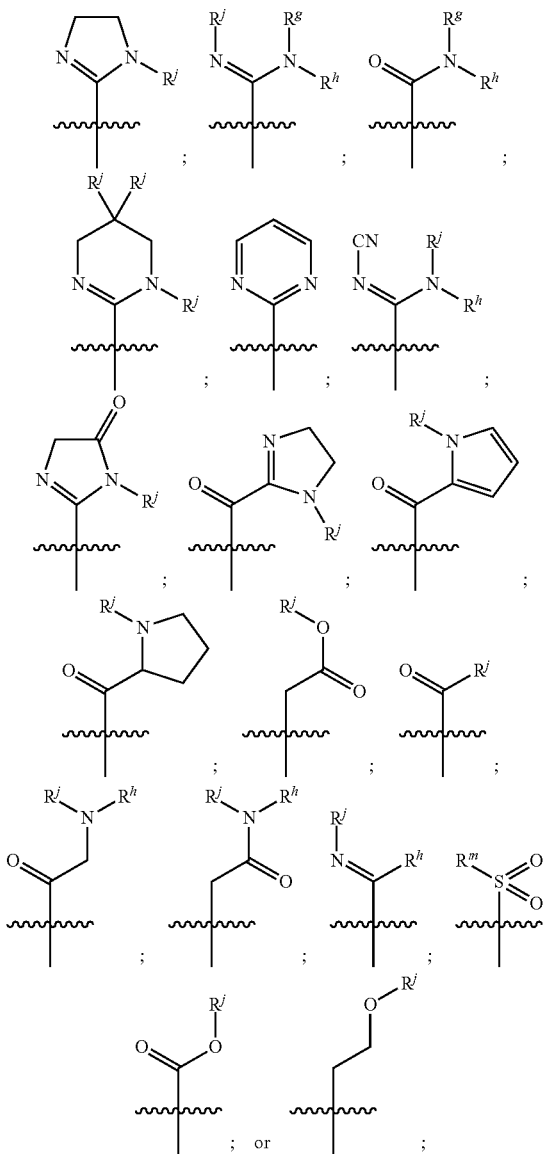

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of either of formula IVa or formula IVb, p is 2, q is 2, m is 0 or 1, n is 3, one of $R^5$ and $R^6$ is hydrogen or alkyl, and the other is:

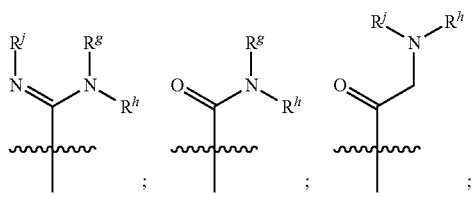

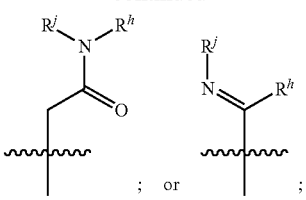

wherein $R^g$, $R^h$, $R^i$ and $R^j$ are hydrogen or alkyl.

In certain embodiments of formula IVa m is 0 or 1, n is 1, s is 0 or 1, and $R^5$ and $R^6$ are hydrogen. In such embodiments $R^1$ and $R^7$ are preferably halo.

In certain embodiments of formula IVa m is 0 or 1, n is 1, s is 0 or 1, one of $R^5$ and $R^6$ is hydrogen, and the other is alkyl, preferably methyl. In such embodiments $R^1$ and $R^7$ are preferably halo.

In certain embodiments of formula IVa m is 0 or 1, n is 1, s is 0 or 1, one of $R^5$ and $R^6$ is hydrogen, and the other is amidinyl. In such embodiments $R^1$ and $R^7$ are preferably halo.

In certain embodiments of formula IVa m is 0 or 1, n is 1, s is 0 or 1, one of $R^5$ and $R^6$ is hydrogen, and the other is aminocarbonyl. In such embodiments $R^1$ and $R^7$ are preferably halo.

In certain embodiments of formula IVa m is 0 or 1, n is 1, s is 0 or 1, one of $R^5$ and $R^6$ is hydrogen, and the other is alkylcarbonyl. In such embodiments $R^1$ and $R^7$ are preferably halo.

Iri certain embodiments of formula IVa m is 0 or 1, n is 1, s is 0 or 1, one of $R^5$ and $R^6$ is hydrogen, and the other is alkoxycarbonyl. In such embodiments $R^1$ and $R^7$ are preferably halo.

In certain embodiments of formula IVa m is 0 or 1, n is 1, s is 0 or 1, one of $R^5$ and $R^6$ is hydrogen, and the other is aminocarbonylalkyl. In such embodiments $R^1$ and $R^7$ are preferably halo.

In certain embodiments of formula IVa m is 0 or 1, n is 1, s is 0 or 1, one of $R^5$ and $R^6$ is hydrogen, and the other is alkoxycarbonylalkyl. In such embodiments $R^1$ and $R^7$ are preferably halo.

In certain embodiments of formula IVa m is 0 or 1, n is 1, s is 0 or 1, one of $R^5$ and $R^6$ is hydrogen, and the other is alkylsulfonyl. In such embodiments $R^1$ and $R^7$ are preferably halo.

In certain embodiments of formula IVa m is 0 or 1, n is 1, s is 0 or 1, one of $R^5$ and $R^6$ is hydrogen, and the other is hydroxyalkylcarbonyl. In such embodiments $R^1$ and $R^7$ are preferably halo.

Where any of $R^1$, $R^2$, $R^3$, $R^4$, $R^5$, $R^6$, $R^7$, $R^a$, $R^b$, $R^c$, $R^d$, $R^e$, $R^f$, $R^g$, $R^h$, $R^i$, $R^j$, $R^k$ and $R^m$ herein are alkyl or contain an alkyl moiety, such alkyl is preferably lower alkyl, i.e. $C_1$-$C_6$alkyl, and more preferably $C_1$-$C_4$alkyl.

Representative compounds in accordance with the invention are shown in Table 1 together with melting point or mass spectrum M+H associated with each compound. Melting points in many instances are shown for corresponding addition salts.

TABLE 1

| # | Structure | Name | Mp or M + H |
|---|-----------|------|-------------|
| 1 | 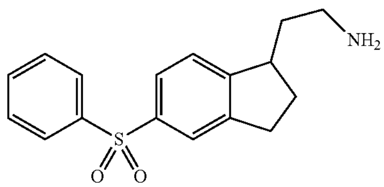 [SMILES: NCCC1CCc2cc(S(=O)(=O)c3ccccc3)ccc21] | 2-(5-Benzenesulfonyl-indan-1-yl)-ethylamine | 302 |
| 2 | 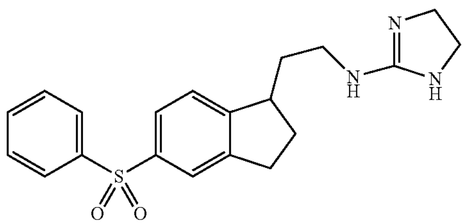 [SMILES: O=S(=O)(c1ccccc1)c1ccc2c(c1)CCC2CCNC1=NCCN1] | [2-(5-Benzenesulfonyl-indan-1-yl)-ethyl]-(4,5-dihydro-1H-imidazol-2-yl)-amine | 370 |
| 3 | 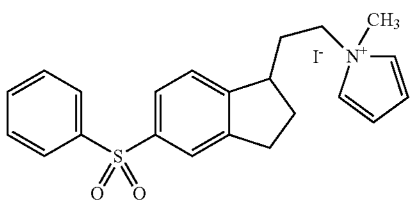 [SMILES: C[N+]1(CCC2CCc3cc(S(=O)(=O)c4ccccc4)ccc32)C=CC=C1 ; [I-]] | 1-[2-(5-Benzenesulfonyl-indan-1-yl)-ethyl]-1-methyl-1H-pyrrolium iodide | 367 |
| 4 | 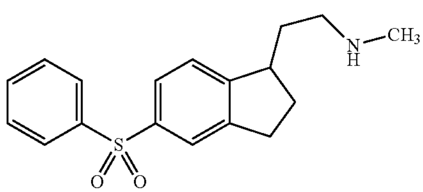 [SMILES: CNCCC1CCc2cc(S(=O)(=O)c3ccccc3)ccc21] | [2-(5-Benzenesulfonyl-indan-1-yl)-ethyl]-methyl-amine | 316 |
| 5 | 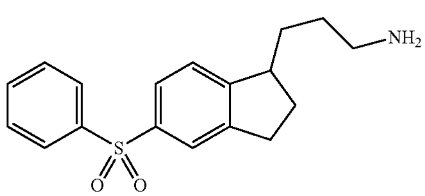 [SMILES: NCCCC1CCc2cc(S(=O)(=O)c3ccccc3)ccc21] | 3-(5-Benzenesulfonyl-indan-1-yl)-propylamine | 316 |
| 6 | 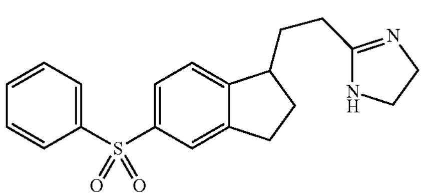 [SMILES: O=S(=O)(c1ccccc1)c1ccc2c(c1)CCC2CCC1=NCCN1] | 2-[2-(5-Benzenesulfonyl-indan-1-yl)-ethyl]-4,5-dihydro-1H-imidazole | 355 |
| 7 | 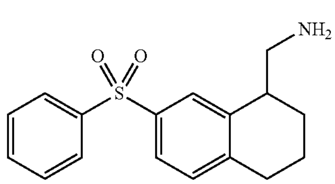 [SMILES: NCC1CCCc2ccc(S(=O)(=O)c3ccccc3)cc21] | C-(7-Benzenesulfonyl-1,2,3,4-tetrahydro-naphthalen-1-yl)-methylamine | 302 |
| 8 | 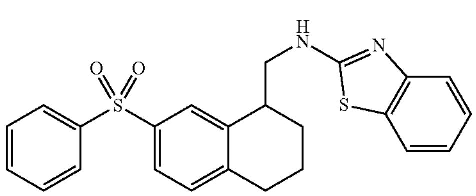 [SMILES: O=S(=O)(c1ccccc1)c1ccc2c(c1)C(CNc1nc3ccccc3s1)CCC2] | (7-Benzenesulfonyl-1,2,3,4-tetrahydro-naphthalen-1-ylmethyl)-benzothiazol-2-yl-amine | 435 |

TABLE 1-continued

| # | Structure | Name | Mp or M + H |
|---|-----------|------|-------------|
| 9 | 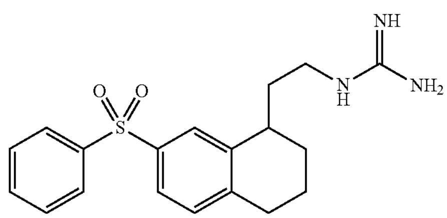 [SMILES: N=C(N)NCCC1CCCc2ccc(S(=O)(=O)c3ccccc3)cc21] | N-[2-(7-Benzenesulfonyl-1,2,3,4-tetrahydro-naphthalen-1-yl)-ethyl]-guanidine | 358 |
| 10 | 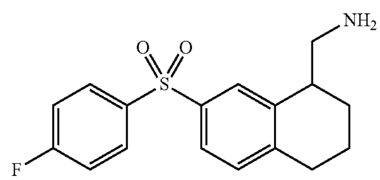 [SMILES: NCC1CCCc2ccc(S(=O)(=O)c3ccc(F)cc3)cc21] | C-[7-(4-Fluoro-benzenesulfonyl)-1,2,3,4-tetrahydro-naphthalen-1-yl]-methylamine | |
| 11 | 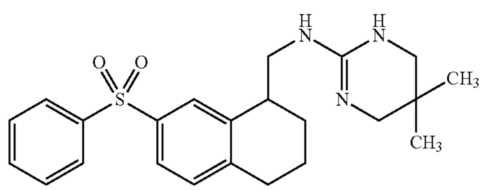 [SMILES: CC1(C)CN=C(NCC2CCCc3ccc(S(=O)(=O)c4ccccc4)cc32)NC1] | (7-Benzenesulfonyl-1,2,3,4-tetrahydro-naphthalen-1-ylmethyl)-(5,5-dimethyl-1,4,5,6-tetrahydro-pyrimidin-2-yl)-amine | 320 |
| 12 | 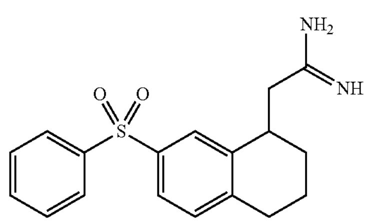 [SMILES: N=C(N)CC1CCCc2ccc(S(=O)(=O)c3ccccc3)cc21] | 2-(7-Benzenesulfonyl-1,2,3,4-tetrahydro-naphthalen-1-yl)-acetamidine | 329 |
| 13 | 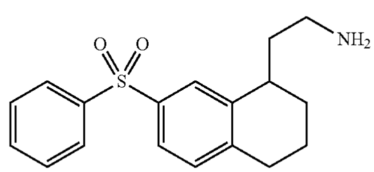 [SMILES: NCCC1CCCc2ccc(S(=O)(=O)c3ccccc3)cc21] | 2-(7-Benzenesulfonyl-1,2,3,4-tetrahydro-naphthalen-1-yl)-ethylamine | 316 |
| 14 | 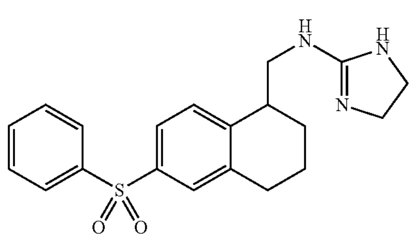 [SMILES: O=S(=O)(c1ccccc1)c1ccc2c(c1)CCCC2CNC1=NCCN1] | (6-Benzenesulfonyl-1,2,3,4-tetrahydro-naphthalen-1-ylmethyl)-(4,5-dihydro-1H-imidazol-2-yl)-amine | 370 |
| 15 | 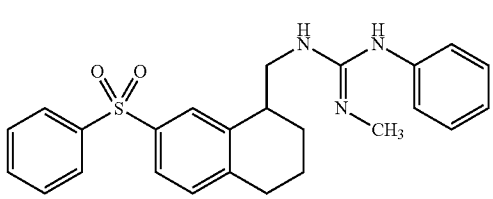 [SMILES: C/N=C(/NCC1CCCc2ccc(S(=O)(=O)c3ccccc3)cc21)Nc1ccccc1] | N-(7-Benzenesulfonyl-1,2,3,4-tetrahydro-naphthalen-1-ylmethyl)-N'-methyl-N''-phenyl-guanidine | 434 |

TABLE 1-continued

| # | Structure | Name | Mp or M + H |
|---|-----------|------|-------------|
| 16 | 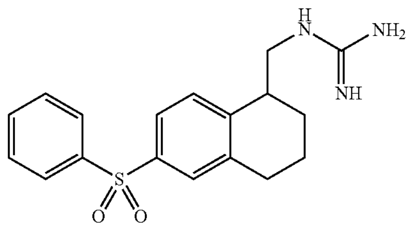 [SMILES: N=C(N)NCC1CCCc2cc(S(=O)(=O)c3ccccc3)ccc21] | N-(6-Benzenesulfonyl-1,2,3,4-tetrahydro-naphthalen-1-ylmethyl)-guanidine | 344 |
| 17 | 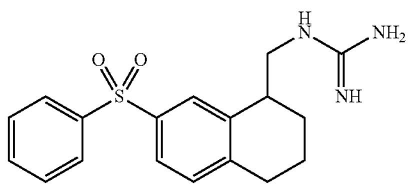 [SMILES: N=C(N)NCC1CCCc2ccc(S(=O)(=O)c3ccccc3)cc21] | N-(7-Benzenesulfonyl-1,2,3,4-tetrahydro-naphthalen-1-ylmethyl)-guanidine | 344 |
| 18 | 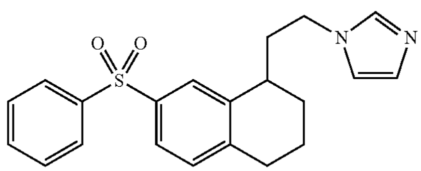 [SMILES: O=S(=O)(c1ccccc1)c1ccc2c(c1)C(CCn1ccnc1)CCC2] | 1-[2-(7-Benzenesulfonyl-1,2,3,4-tetrahydro-naphthalen-1-yl)-ethyl]-1H-imidazole | 367 |
| 19 | 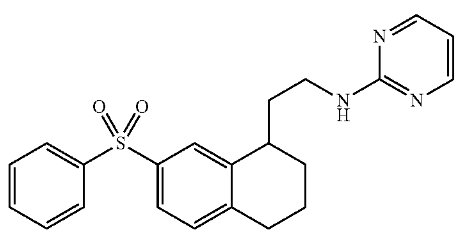 [SMILES: O=S(=O)(c1ccccc1)c1ccc2c(c1)C(CCNc1ncccn1)CCC2] | [2-(7-Benzenesulfonyl-1,2,3,4-tetrahydro-naphthalen-1-yl)-ethyl]-pyrimidin-2-yl-amine | 394 |
| 20 | 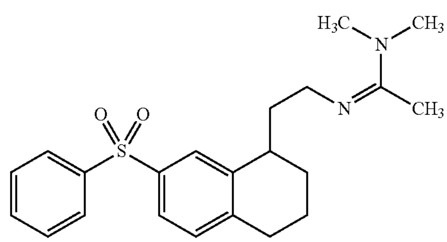 [SMILES: C/C(=N/CCC1CCCc2ccc(S(=O)(=O)c3ccccc3)cc21)N(C)C] | N'-[2-(7-Benzenesulfonyl-1,2,3,4-tetrahydro-naphthalen-1-yl)-ethyl]-N,N-dimethyl-acetamidine | 385 |
| 21 | 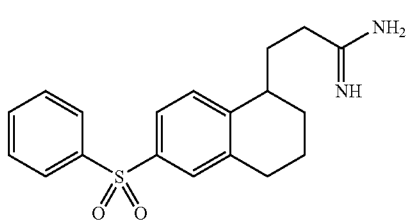 [SMILES: N=C(N)CCC1CCCc2cc(S(=O)(=O)c3ccccc3)ccc21] | 3-(6-Benzenesulfonyl-1,2,3,4-tetrahydro-naphthalen-1-yl)-propionamidine | 343 |
| 22 | 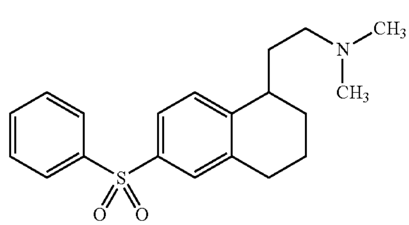 [SMILES: CN(C)CCC1CCCc2cc(S(=O)(=O)c3ccccc3)ccc21] | [2-(6-Benzenesulfonyl-1,2,3,4-tetrahydro-naphthalen-1-yl)-ethyl]-dimethyl-amine | 344 |

TABLE 1-continued

| # | Structure | Name | Mp or M + H |
|---|---|---|---|
| 23 | 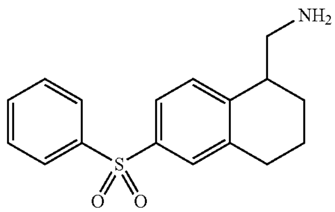 [SMILES: NCC1CCCc2cc(S(=O)(=O)c3ccccc3)ccc21] | C-(6-Benzenesulfonyl-1,2,3,4-tetrahydro-naphthalen-1-yl)-methylamine | 302 |
| 24 | 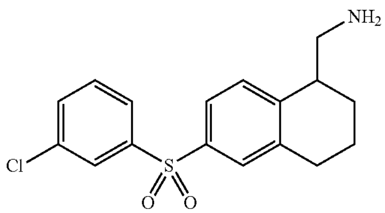 [SMILES: NCC1CCCc2cc(S(=O)(=O)c3cccc(Cl)c3)ccc21] | C-[6-(3-Chloro-benzenesulfonyl)-1,2,3,4-tetrahydro-naphthalen-1-yl]-methylamine | 336 |
| 25 | 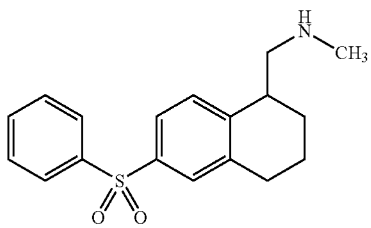 [SMILES: CNCC1CCCc2cc(S(=O)(=O)c3ccccc3)ccc21] | (6-Benzenesulfonyl-1,2,3,4-tetrahydro-naphthalen-1-ylmethyl)-methyl-amine | 316 |
| 26 | 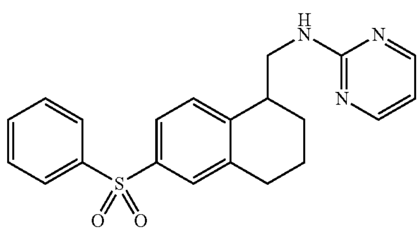 [SMILES: O=S(=O)(c1ccccc1)c1ccc2c(c1)CCCC2CNc1ncccn1] | (6-Benzenesulfonyl-1,2,3,4-tetrahydro-naphthalen-1-ylmethyl)-pyrimidin-2-yl-amine | 380 |
| 27 | 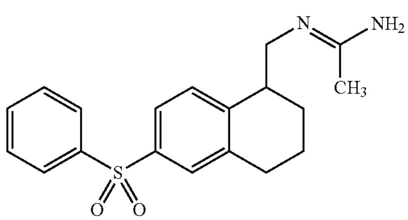 [SMILES: C/C(N)=N\CC1CCCc2cc(S(=O)(=O)c3ccccc3)ccc21] | N-(6-Benzenesulfonyl-1,2,3,4-tetrahydro-naphthalen-1-ylmethyl)-acetamidine | 343 |
| 28 | 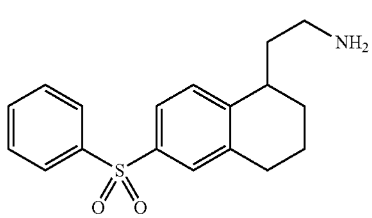 [SMILES: NCCC1CCCc2cc(S(=O)(=O)c3ccccc3)ccc21] | 2-(6-Benzenesulfonyl-1,2,3,4-tetrahydro-naphthalen-1-yl)-ethylamine | 316 |
| 29 | 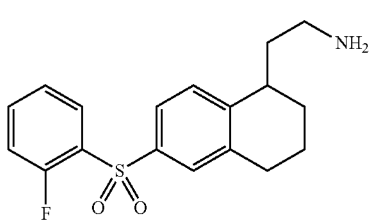 [SMILES: NCCC1CCCc2cc(S(=O)(=O)c3ccccc3F)ccc21] | 2-[6-(2-Fluoro-benzenesulfonyl)-1,2,3,4-tetrahydro-naphthalen-1-yl]-ethylamine | 334 |

TABLE 1-continued

| # | Structure | Name | Mp or M + H |
|---|---|---|---|
| 30 | 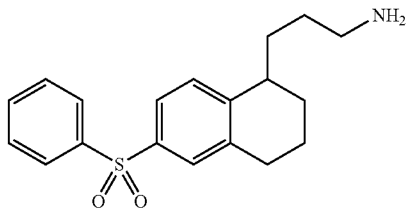 [SMILES: NCCCC1CCCc2cc(S(=O)(=O)c3ccccc3)ccc21] | 3-(6-Benzenesulfonyl-1,2,3,4-tetrahydro-naphthalen-1-yl)-propylamine | 330 |
| 31 | 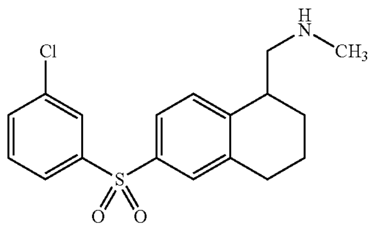 [SMILES: CNCC1CCCc2cc(S(=O)(=O)c3cccc(Cl)c3)ccc21] | [6-(3-Chloro-benzenesulfonyl)-1,2,3,4-tetrahydro-naphthalen-1-ylmethyl]-methyl-amine | 350 |
| 32 | 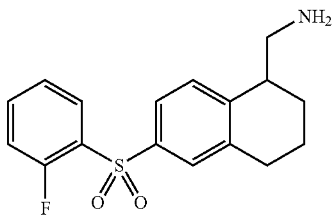 [SMILES: NCC1CCCc2cc(S(=O)(=O)c3ccccc3F)ccc21] | C-[6-(2-Fluoro-benzenesulfonyl)-1,2,3,4-tetrahydro-naphthalen-1-yl]-methylamine | 320 |
| 33 | 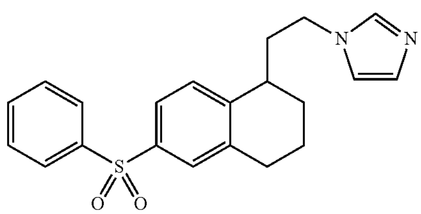 [SMILES: O=S(=O)(c1ccccc1)c1ccc2c(c1)CCCC2CCn1ccnc1] | 1-[2-(6-Benzenesulfonyl-1,2,3,4-tetrahydro-naphthalen-1-yl)-ethyl]-1H-imidazole | 367 |
| 34 | 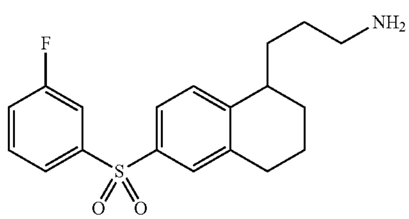 [SMILES: NCCCC1CCCc2cc(S(=O)(=O)c3cccc(F)c3)ccc21] | 3-[6-(3-Fluoro-benzenesulfonyl)-1,2,3,4-tetrahydro-naphthalen-1-yl]-propylamine | 348 |
| 35 | 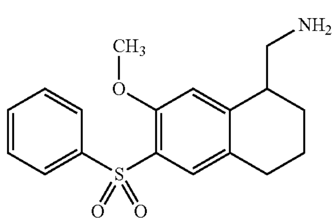 [SMILES: COc1cc2c(cc1S(=O)(=O)c1ccccc1)CCCC2CN] | C-(6-Benzenesulfonyl-7-methoxy-1,2,3,4-tetrahydro-naphthalen-1-yl)-methylamine | 332 |
| 36 | 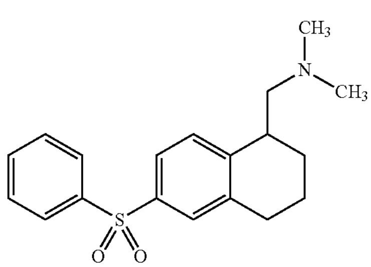 [SMILES: CN(C)CC1CCCc2cc(S(=O)(=O)c3ccccc3)ccc21] | (6-Benzenesulfonyl-1,2,3,4-tetrahydro-naphthalen-1-ylmethyl)-dimethyl-amine | 330 |

TABLE 1-continued

| # | Structure | Name | Mp or M + H |
|---|---|---|---|
| 37 | 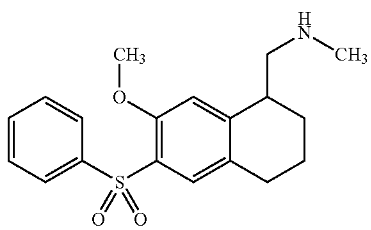 [SMILES: CNCC1CCCc2cc(S(=O)(=O)c3ccccc3)c(OC)cc21] | (6-Benzenesulfonyl-7-methoxy-1,2,3,4-tetrahydro-naphthalen-1-ylmethyl)-methyl-amine | 346 |
| 38 | 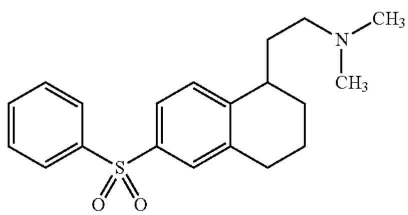 [SMILES: CN(C)CCC1CCCc2cc(S(=O)(=O)c3ccccc3)ccc21] | [2-(6-Benzenesulfonyl-1,2,3,4-tetrahydro-naphthalen-1-yl)-ethyl]-dimethyl-amine | 344 |
| 39 | 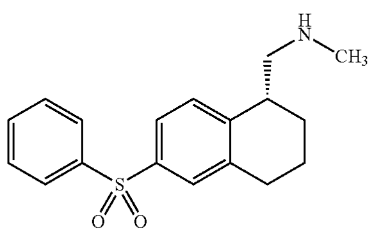 [SMILES: CNC[C@@H]1CCCc2cc(S(=O)(=O)c3ccccc3)ccc21] | (R)-(6-Benzenesulfonyl-1,2,3,4-tetrahydro-naphthalen-1-ylmethyl)-methyl-amine | 316 |
| 40 | 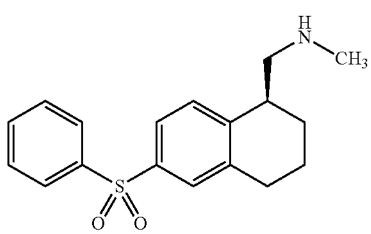 [SMILES: CNC[C@H]1CCCc2cc(S(=O)(=O)c3ccccc3)ccc21] | (S)-(6-Benzenesulfonyl-1,2,3,4-tetrahydro-naphthalen-1-ylmethyl)-methyl-amine | 146-147° C. (TFA Salt) |
| 41 | 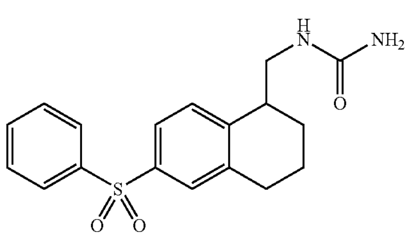 [SMILES: NC(=O)NCC1CCCc2cc(S(=O)(=O)c3ccccc3)ccc21] | (6-Benzenesulfonyl-1,2,3,4-tetrahydro-naphthalen-1-ylmethyl)-urea | 345 |
| 42 | 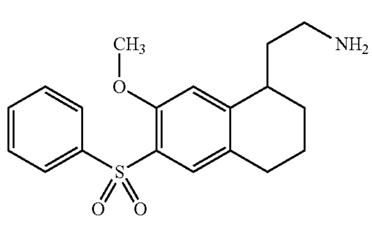 [SMILES: COc1cc2c(cc1S(=O)(=O)c1ccccc1)CCCC2CCN] | 2-(6-Benzenesulfonyl-7-methoxy-1,2,3,4-tetrahydro-naphthalen-1-yl)-ethylamine | 346 |

TABLE 1-continued

| # | Name | Mp or M + H |
|---|------|-------------|
| 43 | C-[6-(3-Fluoro-benzenesulfonyl)-1,2,3,4-tetrahydro-naphthalen-1-yl]-methylamine | 320 |
| 44 | [2-(6-Benzenesulfonyl-7-methoxy-1,2,3,4-tetrahydro-naphthalen-1-yl)-ethyl]-methyl-amine | 360 |
| 45 | N-[2-(6-Benzenesulfonyl-1,2,3,4-tetrahydro-naphthalen-1-yl)-acetyl]-guanidine | 372 |
| 46 | [6-(3-Fluoro-benzenesulfonyl)-1,2,3,4-tetrahydro-naphthalen-1-ylmethyl]-methyl-amine | 334 |
| 47 | Ethyl-[6-(3-fluoro-benzenesulfonyl)-1,2,3,4-tetrahydro-naphthalen-1-ylmethyl]-amine | 348 |
| 48 | (R)-C-(6-Benzenesulfonyl-1,2,3,4-tetrahydro-naphthalen-1-yl)-methylamine | 302 |
| 49 | (R)-C-[6-(3-Methoxy-benzenesulfonyl)-1,2,3,4-tetrahydro-naphthalen-1-yl]-methylamine | 188-189° C. (HCl Salt) |

TABLE 1-continued

| # | Structure | Name | Mp or M + H |
|---|---|---|---|
| 50 | 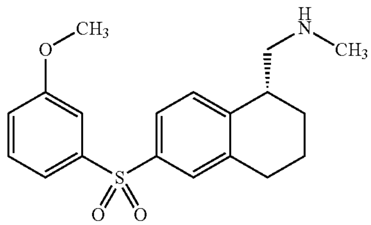 [SMILES: CNC[C@@H]1CCCc2cc(S(=O)(=O)c3cccc(OC)c3)ccc21] | (R)-[6-(3-Methoxy-benzenesulfonyl)-1,2,3,4-tetrahydro-naphthalen-1-ylmethyl]-methyl-amine | 194-195° C. (HCl Salt) |
| 51 | 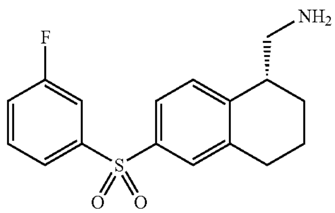 | (R)-C-[6-(3-Fluoro-benzenesulfonyl)-1,2,3,4-tetrahydro-naphthalen-1-yl]-methylamine | 320 |
| 52 | 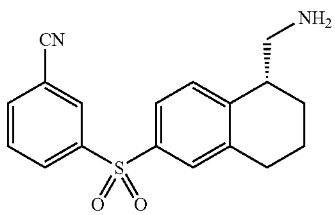 [SMILES: N#Cc1cccc(S(=O)(=O)c2ccc3c(c2)CCC[C@H]3CN)c1] | (R)-3-(5-Aminomethyl-5,6,7,8-tetrahydro-naphthalene-2-sulfonyl)-benzonitrile | 212-213° C. (Oxalate Salt) |
| 53 | 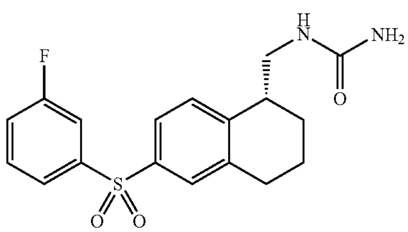 [SMILES: NC(=O)NC[C@@H]1CCCc2cc(S(=O)(=O)c3cccc(F)c3)ccc21] | (R)-[6-(3-Fluoro-benzenesulfonyl)-1,2,3,4-tetrahydro-naphthalen-1-ylmethyl]-urea | 363 |
| 54 | 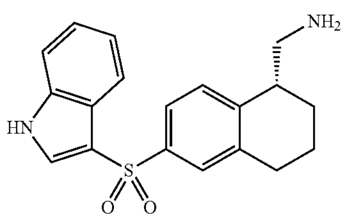 [SMILES: NC[C@@H]1CCCc2cc(S(=O)(=O)c3c[nH]c4ccccc34)ccc21] | (R)-C-[6-(1H-Indole-3-sulfonyl)-1,2,3,4-tetrahydro-naphthalen-1-yl]-methylamine | 341 |
| 55 | 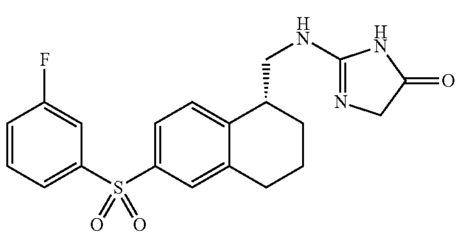 [SMILES: O=C1CN=C(NC[C@@H]2CCCc3cc(S(=O)(=O)c4cccc(F)c4)ccc32)N1] | (R)-2-{[6-(3-Fluoro-benzenesulfonyl)-1,2,3,4-tetrahydro-naphthalen-1-ylmethyl]-amino}-3,5-dihydro-imidazol-4-one | 402 |
| 56 | 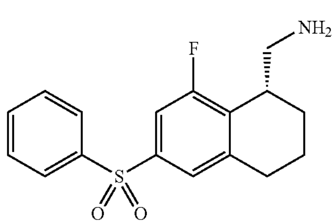 [SMILES: NC[C@@H]1CCCc2cc(S(=O)(=O)c3ccccc3)cc(F)c21] | (R)-C-(6-Benzenesulfonyl-8-fluoro-1,2,3,4-tetrahydro-naphthalen-1-yl)-methylamine | 248-249° C (HCl Salt) |

TABLE 1-continued

| # | Structure | Name | Mp or M + H |
|---|---|---|---|
| 57 | 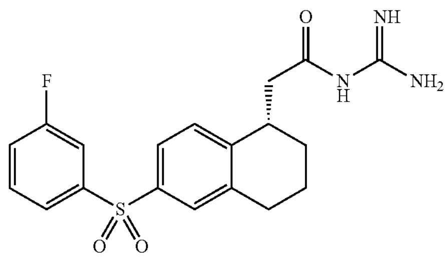 [SMILES: N=C(N)NC(=O)C[C@@H]1CCCc2cc(S(=O)(=O)c3cccc(F)c3)ccc21] | (R)-N-{2-[6-(3-Fluoro-benzenesulfonyl)-1,2,3,4-tetrahydro-naphthalen-1-yl]-acetyl}-guanidine | 390 |
| 58 | 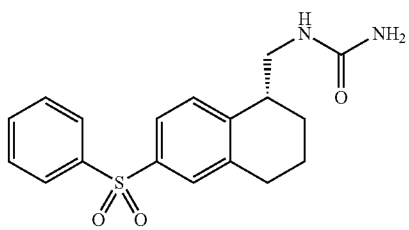 | (R)-(6-Benzenesulfonyl-1,2,3,4-tetrahydro-naphthalen-1-ylmethyl)-urea | 345 |
| 59 | 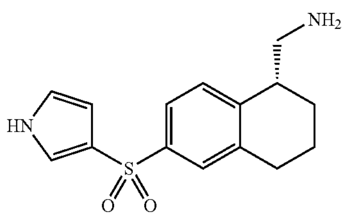 [SMILES: NC[C@@H]1CCCc2cc(S(=O)(=O)c3cc[nH]c3)ccc21] | (R)-C-[6-(1H-Pyrrole-3-sulfonyl)-1,2,3,4-tetrahydro-naphthalen-1-yl]-methylamine | 291 |
| 60 | 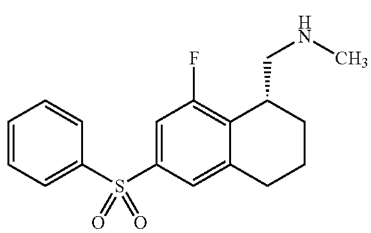 [SMILES: CNC[C@@H]1CCCc2cc(S(=O)(=O)c3ccccc3)cc(F)c21] | (R)-(6-Benzenesulfonyl-8-fluoro-1,2,3,4-tetrahydro-naphthalen-1-ylmethyl)-methyl-amine | 334 |
| 61 | 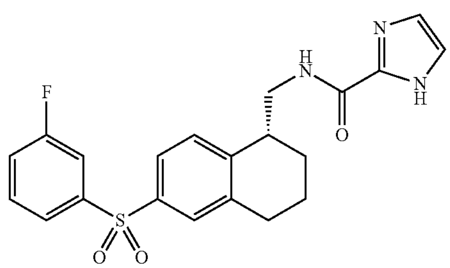 [SMILES: O=C(NC[C@@H]1CCCc2cc(S(=O)(=O)c3cccc(F)c3)ccc21)c1ncc[nH]1] | (R)-1H-Imidazole-2-carboxylic acid [6-(3-fluoro-benzenesulfonyl)-1,2,3,4-tetrahydro-naphthalen-1-ylmethyl]-amide | 414 |
| 62 | 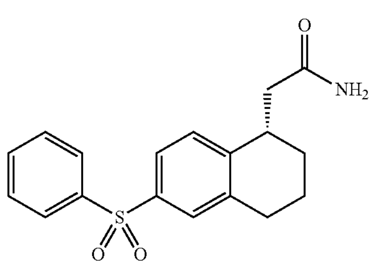 [SMILES: NC(=O)C[C@@H]1CCCc2cc(S(=O)(=O)c3ccccc3)ccc21] | (R)-2-(6-Benzenesulfonyl-1,2,3,4-tetrahydro-naphthalen-1-yl)-acetamide | 330 |

TABLE 1-continued

| # | Structure | Name | Mp or M + H |
|---|---|---|---|
| 63 | 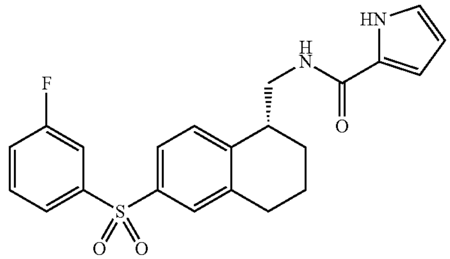 [SMILES: O=C(NC[C@@H]1CCCc2cc(S(=O)(=O)c3cccc(F)c3)ccc21)c1ccc[nH]1] | (R)-1H-Pyrrole-2-carboxylic acid [6-(3-fluoro-benzenesulfonyl)-1,2,3,4-tetrahydro-naphthalen-1-ylmethyl]-amide | 413 |
| 64 | 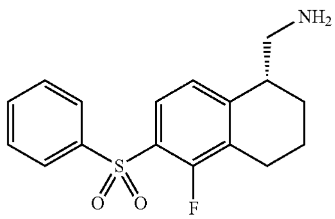 [SMILES: NC[C@@H]1CCCc2c1ccc(S(=O)(=O)c1ccccc1)c2F] | (R)-C-(6-Benzenesulfonyl-5-fluoro-1,2,3,4-tetrahydro-naphthalen-1-yl)-methylamine | 320 |
| 65 | 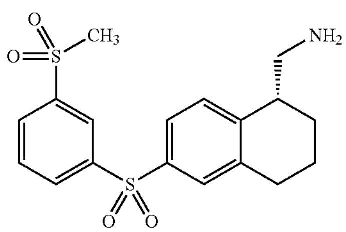 [SMILES: CS(=O)(=O)c1cccc(S(=O)(=O)c2ccc3c(c2)CCC[C@H]3CN)c1] | (R)-C-[6-(3-Methanesulfonyl-benzenesulfonyl)-1,2,3,4-tetrahydro-naphthalen-1-yl]-methylamine | 265-266° C. (HCl Salt) |
| 66 | 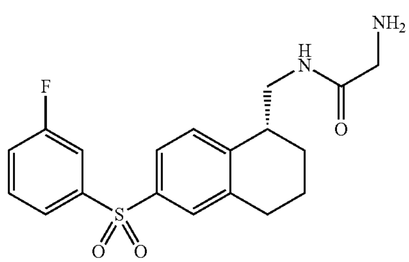 [SMILES: NCC(=O)NC[C@@H]1CCCc2cc(S(=O)(=O)c3cccc(F)c3)ccc21] | (R)-2-Amino-N-[6-(3-fluoro-benzenesulfonyl)-1,2,3,4-tetrahydro-naphthalen-1-ylmethyl]-acetamide | 377 |
| 67 | 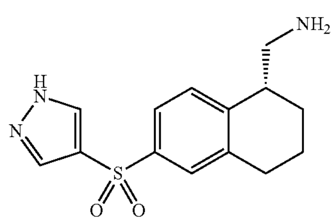 [SMILES: NC[C@@H]1CCCc2cc(S(=O)(=O)c3cn[nH]c3)ccc21] | (R)-C-[6-(1H-Pyrazole-4-sulfonyl)-1,2,3,4-tetrahydro-naphthalen-1-yl]-methylamine | 181-182° C. (HCl Salt) |
| 68 | 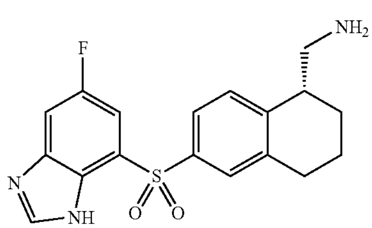 [SMILES: NC[C@@H]1CCCc2cc(S(=O)(=O)c3cc(F)cc4nc[nH]c34)ccc21] | (R)-C-[6-(6-Fluoro-3H-benzoimidazole-4-sulfonyl)-1,2,3,4-tetrahydro-naphthalen-1-yl]-methylamine | 360 |

TABLE 1-continued

| # | Structure | Name | Mp or M + H |
|---|---|---|---|
| 69 | 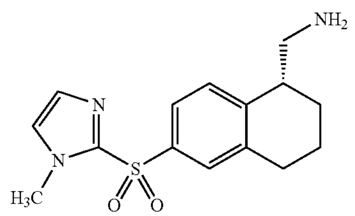 [SMILES: Cn1ccnc1S(=O)(=O)c1ccc2c(c1)CCC[C@H]2CN] | (R)-C-[6-(1-Methyl-1H-imidazole-2-sulfonyl)-1,2,3,4-tetrahydro-naphthalen-1-yl]-methylamine | 196-197° C. (Oxalate Salt) |
| 70 | 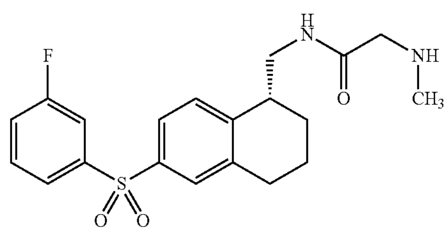 [SMILES: CNCC(=O)NC[C@@H]1CCCc2cc(S(=O)(=O)c3cccc(F)c3)ccc21] | (R)-N-[6-(3-Fluoro-benzenesulfonyl)-1,2,3,4-tetrahydro-naphthalen-1-ylmethyl]-2-methylamino-acetamide | 391 |
| 71 | 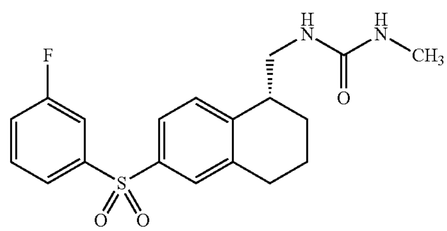 [SMILES: CNC(=O)NC[C@@H]1CCCc2cc(S(=O)(=O)c3cccc(F)c3)ccc21] | (R)-1-[6-(3-Fluoro-benzenesulfonyl)-1,2,3,4-tetrahydro-naphthalen-1-ylmethyl]-3-methyl-urea | 377 |
| 72 | 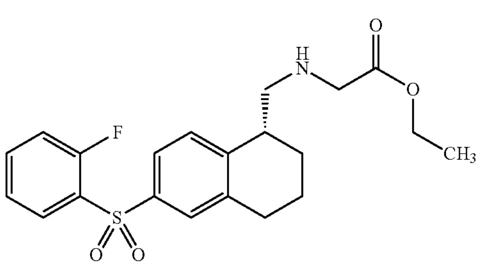 [SMILES: CCOC(=O)CNC[C@@H]1CCCc2cc(S(=O)(=O)c3ccccc3F)ccc21] | (R)-{[6-(2-Fluoro-benzenesulfonyl)-1,2,3,4-tetrahydro-naphthalen-1-ylmethyl]-amino}-acetic acid ethyl ester | 406 |
| 73 | 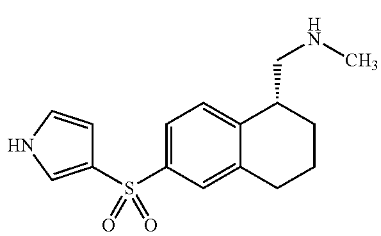 [SMILES: CNC[C@@H]1CCCc2cc(S(=O)(=O)c3cc[nH]c3)ccc21] | (R)-Methyl-[6-(1H-pyrrole-3-sulfonyl)-1,2,3,4-tetrahydro-naphthalen-1-ylmethyl]-amine | 305 |
| 74 | 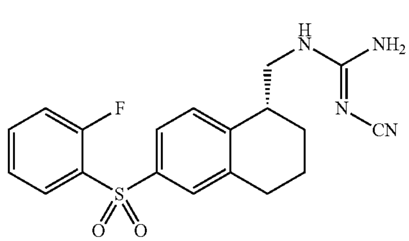 [SMILES: N#C/N=C(\N)NC[C@@H]1CCCc2cc(S(=O)(=O)c3ccccc3F)ccc21] | (R)-N-[6-(2-Fluoro-benzenesulfonyl)-1,2,3,4-tetrahydro-naphthalen-1-ylmethyl]-N'-cyano-guanidine | 387 |

TABLE 1-continued

| # | Structure | Name | Mp or M + H |
|---|-----------|------|-------------|
| 75 | 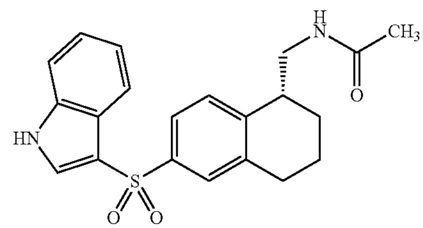 [SMILES: CC(=O)NC[C@@H]1CCCc2cc(S(=O)(=O)c3c[nH]c4ccccc34)ccc21] | (R)-N-[6-(1H-Indole-3-sulfonyl)-1,2,3,4-tetrahydro-naphthalen-1-ylmethyl]-acetamide | 383 |
| 76 | 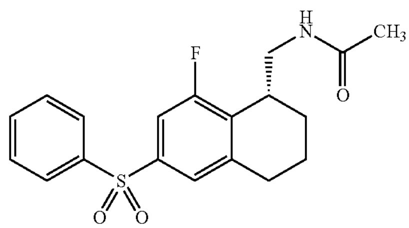 [SMILES: CC(=O)NC[C@@H]1CCCc2cc(S(=O)(=O)c3ccccc3)cc(F)c21] | (R)-N-(6-Benzenesulfonyl-8-fluoro-1,2,3,4-tetrahydro-naphthalen-1-ylmethyl)-acetamide | 362 |
| 77 | 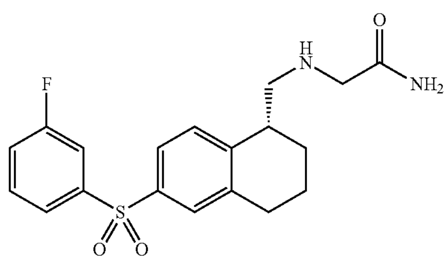 [SMILES: NC(=O)CNC[C@@H]1CCCc2cc(S(=O)(=O)c3cccc(F)c3)ccc21] | (R)-2-{[6-(3-Fluoro-benzenesulfonyl)-1,2,3,4-tetrahydro-naphthalen-1-ylmethyl]-amino}-acetamide | 377 |
| 78 | 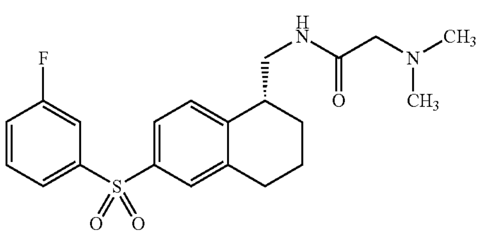 [SMILES: CN(C)CC(=O)NC[C@@H]1CCCc2cc(S(=O)(=O)c3cccc(F)c3)ccc21] | (R)-2-Dimethylamino-N-[6-(3-fluoro-benzenesulfonyl)-1,2,3,4-tetrahydro-naphthalen-1-ylmethyl]-acetamide | 405 |
| 79 | 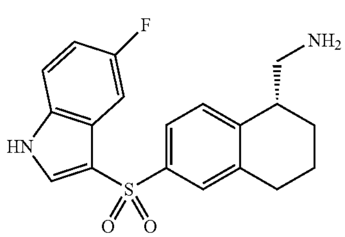 [SMILES: NC[C@@H]1CCCc2cc(S(=O)(=O)c3c[nH]c4ccc(F)cc34)ccc21] | (R)-C-[6-(5-Fluoro-1H-indole-3-sulfonyl)-1,2,3,4-tetrahydro-naphthalen-1-yl]-methylamine | 359 |
| 80 | 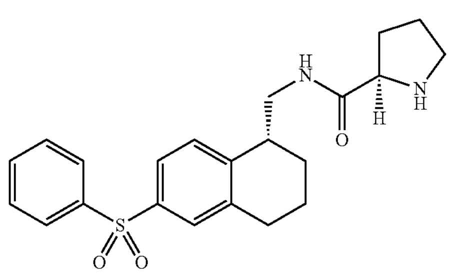 [SMILES: O=C(NC[C@@H]1CCCc2cc(S(=O)(=O)c3ccccc3)ccc21)[C@H]1CCCN1] | (R)-Pyrrolidine-2-carboxylic acid (6-benzenesulfonyl-1,2,3,4-tetrahydro-naphthalen-1-ylmethyl)-amide | 399 |

TABLE 1-continued

| # | Structure | Name | Mp or M + H |
|---|---|---|---|
| 81 | 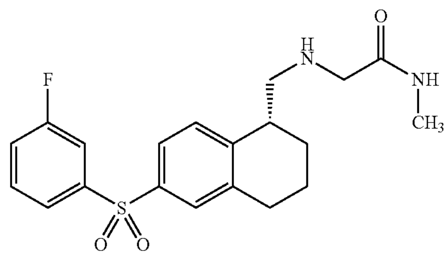 [SMILES: CNC(=O)CNC[C@@H]1CCCc2cc(S(=O)(=O)c3cccc(F)c3)ccc21] | (R)-2-{[6-(3-Fluoro-benzenesulfonyl)-1,2,3,4-tetrahydro-naphthalen-1-ylmethyl]-amino}-N-methyl-acetamide | 391 |
| 82 | 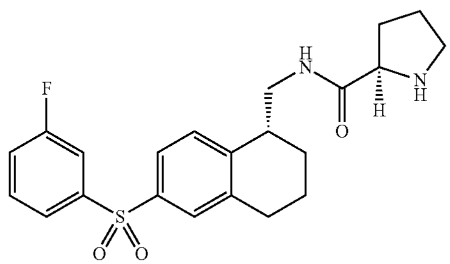 | (R)-Pyrrolidine-2-carboxylic acid [6-(3-fluoro-benzenesulfonyl)-1,2,3,4-tetrahydro-naphthalen-1-ylmethyl]-amide | 417 |
| 83 | 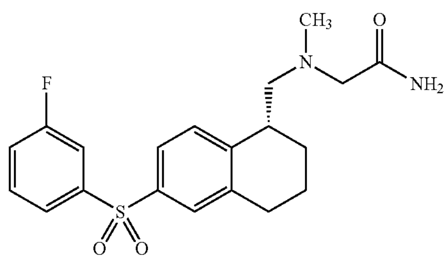 [SMILES: CN(CC(N)=O)C[C@@H]1CCCc2cc(S(=O)(=O)c3cccc(F)c3)ccc21] | (R)-2-{[6-(3-Fluoro-benzenesulfonyl)-1,2,3,4-tetrahydro-naphthalen-1-ylmethyl]-methyl-amino}-acetamide | 391 |
| 84 | 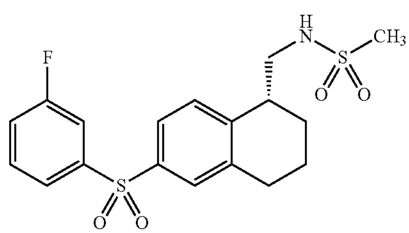 [SMILES: CS(=O)(=O)NC[C@@H]1CCCc2cc(S(=O)(=O)c3cccc(F)c3)ccc21] | (R)-N-[6-(3-Fluoro-benzenesulfonyl)-1,2,3,4-tetrahydro-naphthalen-1-ylmethyl]-methanesulfonamide | 398 |
| 85 | 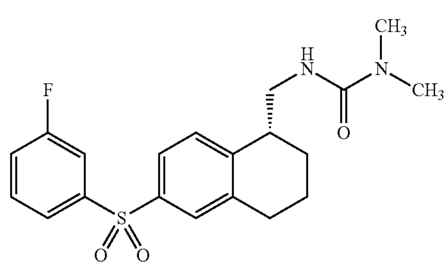 [SMILES: CN(C)C(=O)NC[C@@H]1CCCc2cc(S(=O)(=O)c3cccc(F)c3)ccc21] | (R)-3-[6-(3-Fluoro-benzenesulfonyl)-1,2,3,4-tetrahydro-naphthalen-1-ylmethyl]-1,1-dimethyl-urea | 391 |
| 86 | 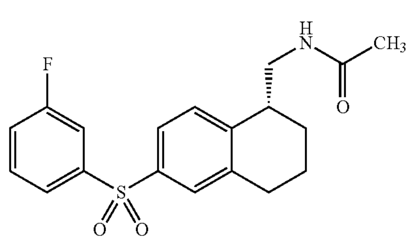 [SMILES: CC(=O)NC[C@@H]1CCCc2cc(S(=O)(=O)c3cccc(F)c3)ccc21] | (R)-N-[6-(3-Fluoro-benzenesulfonyl)-1,2,3,4-tetrahydro-naphthalen-1-ylmethyl]-acetamide | 362 |

TABLE 1-continued

| # | Structure | Name | Mp or M + H |
|---|---|---|---|
| 87 | 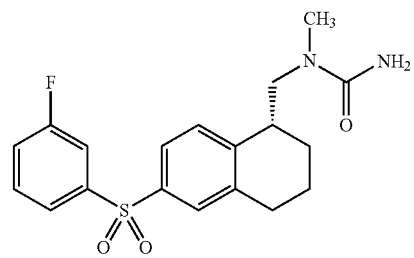 [SMILES: CN(C[C@@H]1CCCc2cc(S(=O)(=O)c3cccc(F)c3)ccc21)C(N)=O] | (R)-1-[6-(3-Fluoro-benzenesulfonyl)-1,2,3,4-tetrahydro-naphthalen-1-ylmethyl]-1-methyl-urea | 377 |
| 88 | 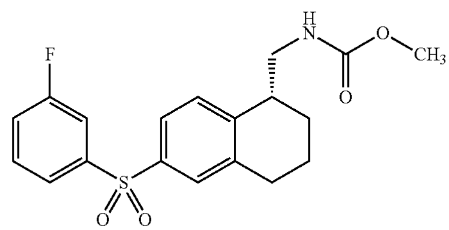 [SMILES: COC(=O)NC[C@@H]1CCCc2cc(S(=O)(=O)c3cccc(F)c3)ccc21] | (R)-[6-(3-Fluoro-benzenesulfonyl)-1,2,3,4-tetrahydro-naphthalen-1-ylmethyl]-carbamic acid methyl ester | 378 |
| 89 | 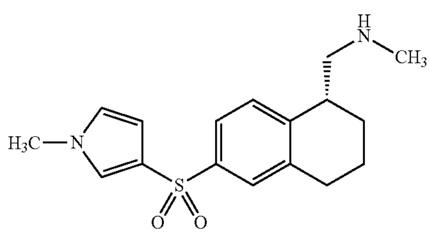 | (R)-Methyl-[6-(1-methyl-1H-pyrrole-3-sulfonyl)-1,2,3,4-tetrahydro-naphthalen-1-ylmethyl]-amine | 319 |
| 90 | 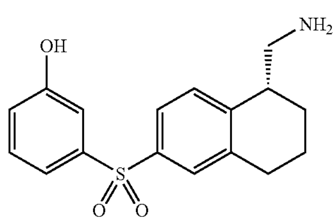 | (R)-3-(5-Aminomethyl-5,6,7,8-tetrahydro-naphthalene-2-sulfonyl)-phenol | 318 |
| 91 | 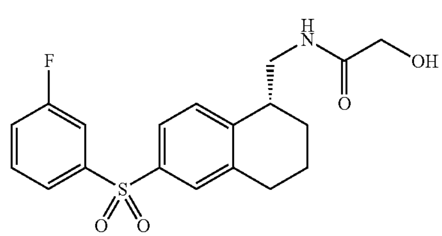 [SMILES: O=C(CO)NC[C@@H]1CCCc2cc(S(=O)(=O)c3cccc(F)c3)ccc21] | (R)-N-[6-(3-Fluoro-benzenesulfonyl)-1,2,3,4-tetrahydro-naphthalen-1-ylmethyl]-2-hydroxy-acetamide | 378 |
| 92 | 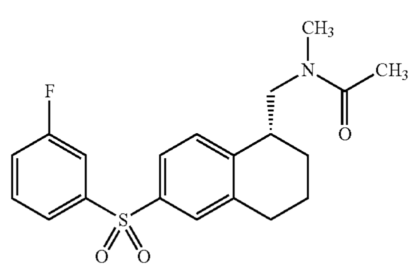 [SMILES: CC(=O)N(C)C[C@@H]1CCCc2cc(S(=O)(=O)c3cccc(F)c3)ccc21] | (R)-N-[6-(3-Fluoro-benzenesulfonyl)-1,2,3,4-tetrahydro-naphthalen-1-ylmethyl]-N-methyl-acetamide | 376 |

TABLE 1-continued

| # | Structure | Name | Mp or M + H |
|---|---|---|---|
| 93 | 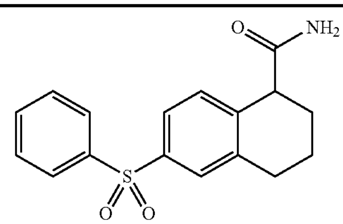 | 6-Benzenesulfonyl-1,2,3,4-tetrahydro-naphthalene-1-carboxylic acid amide | 316 |
| 94 | 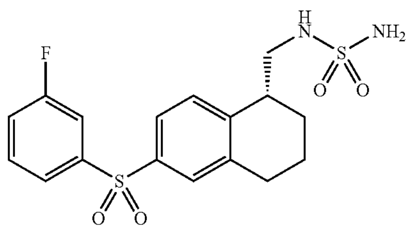 [SMILES: NS(=O)(=O)NC[C@@H]1CCCc2cc(S(=O)(=O)c3cccc(F)c3)ccc21] | (R)-6-Benzenesulfonyl-1,2,3,4-tetrahydro-naphthalene-1-carboxylic acid amide | 399 |
| 95 | 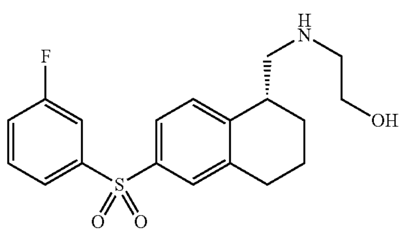 [SMILES: O=S(=O)(c1cccc(F)c1)c1ccc2c(c1)CCC[C@H]2CNCCO] | (R)-2-{[6-(3-Fluoro-benzenesulfonyl)-1,2,3,4-tetrahydro-naphthalen-1-ylmethyl]-amino}-ethano] | 364 |

Another aspect of the invention provides a composition comprising a therapeutically effective amount of at least one compound of formula (I) and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 2004, Volumes 1-56. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein Ar, m, p, q and $R^1$ are as defined herein. Numerous synthetic routes to indane and tetralin compounds are known and may be used in preparation of the subject compounds, and the procedure of Scheme A is only exemplary. Specific examples of the procedure of Scheme A are provided in the following Experimental section.

SCHEME A

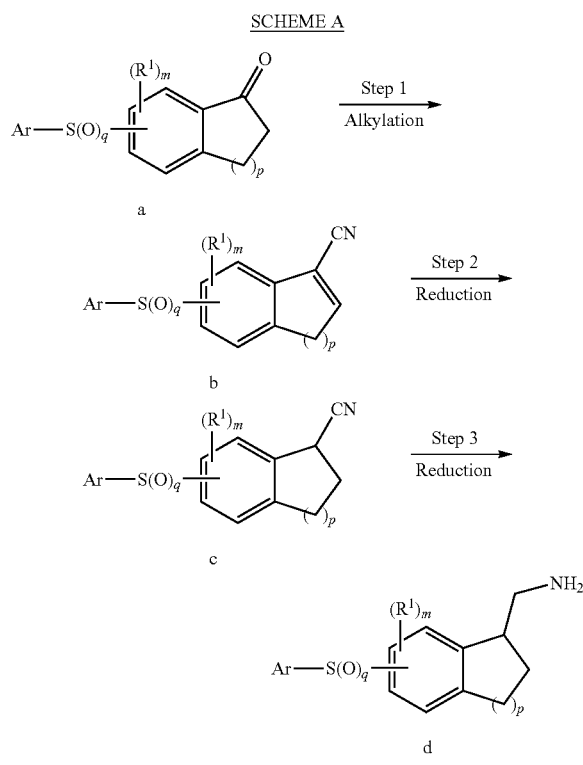

In step 1 of Scheme A, ketone compound a undergoes an alkylation/cyanylation reaction to give an arylsulfonyl nitrile compound b. Ketone compound may comprise, for example, an arylsulfonyl indanone where q is 2 and p 1, an arylsulfonyl tetralinone where q is 2 and p is 2, an arylsulfonyl benzoazepinone where q is 2 and p is 3, or like ketone in accordance with the invention. Corresponding, arylsulfanyl (q=0) and arylsulfinyl (q=1) ketone compounds may be used in this step. Ketone compounds a may be prepared by a variety of techniques known in the art, and specific examples of preparing such compounds are provided below in the Experimental section of this disclosure. The alkylation reaction of step 1 may be achieved by treatment of ketone compound a with trimethylsilyl cyanide in the presence of zinc iodide under polar aprotic solvent conditions, followed by treatment with p-toluene sulfonic acid or like acid.

In step 2, arylsulfonyl nitrile compound is subject to reduction to provide nitrile compound c. This reduction removes a residual unsaturation resulting from step 1, and may be carried out using hydrogen gas with a platinum or palladium catalyst.

A second reduction reaction is carried out in step 3 to reduce the nitrile group of compound c and afford an arylsulfonyl aminomethyl compound d. Compound d is a compound of formula I in accordance with the invention.

Many variations on the procedure of Scheme A are possible and will be readily apparent to those skilled in the art. In certain embodiments the reduction reactions of step 2 and step 3 may be performed in a single step. In other embodiments, the reduction of step 2 may be omitted to provide an additional unsaturation. The amine compound d may be subject to additional alkylation reaction, using suitable protection/deprotection to afford monoalkylamino or dialkylamino compounds. Amine compound d may also undergo subsequent reaction to form amidinyl, guanidinyl, imidazolinyl, imidazolinylamino, and other functionalities. Specific examples of such additional reactions are provided in the Examples below.

Referring to Scheme B, another synthetic route for the subject compounds is shown, wherein X is a leaving group and may be the same or different in each occurrence, R is lower alkyl and may be the same or different in each occurrence, and Ar, m, n, p, q, $R^1$, $R^3$ and $R^4$ are as defined herein.

SCHEME B

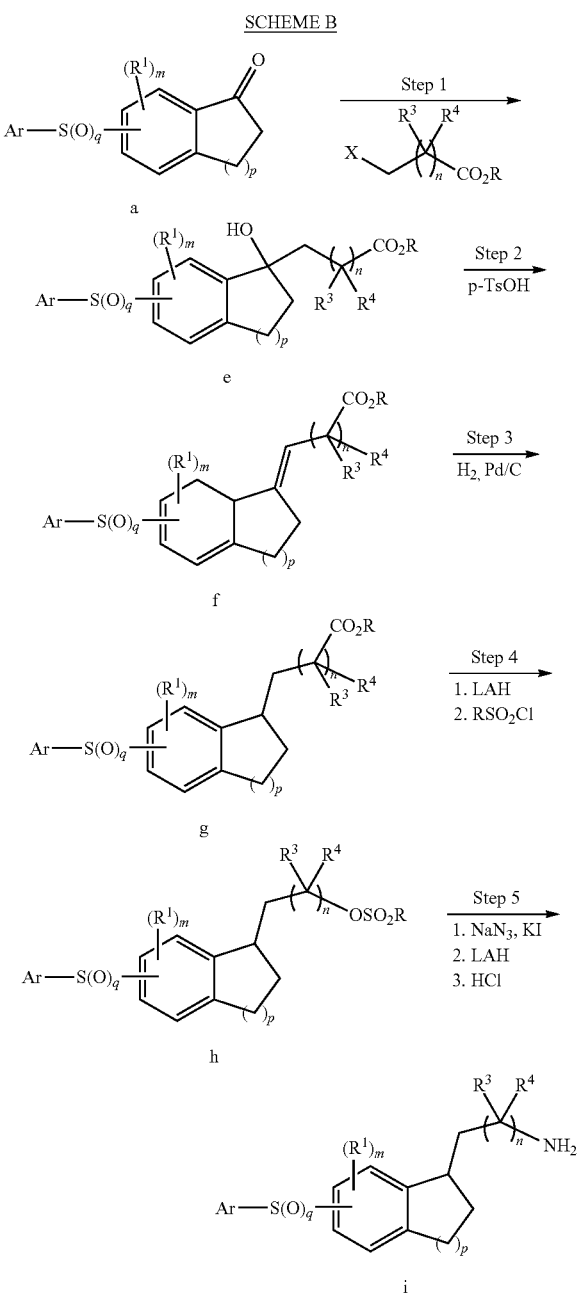

In step 1 of Scheme B, ketone compound a is subject to an alkylation reaction to afford a hydroxy ester compound e. Ketone compound a may be any one of a variety of arylsulfonyl, arylsulfanyl or arylsulfinyl indanone and tetralinone compounds as noted above. Alkylation in step 1 may be effected by treatment of ketone compound a with zinc and iodine, followed by a haloalkyl ester compound such as ethyl bromopropionate (where X is bromo, n is 1, $R^3$ and $R^4$ are hydrogen, and R is ethyl).

In step 2, hydroxy ester compound e is dehydrated by treatment with acid such as para-toluenesulfonic acid, to yield an unsaturated ester compound f. In certain embodiments the dehydration of step 2 may occur spontaneously during step 1, and thus step 2 may be omitted.

A reduction reaction takes place in step 3 in which the residual unsaturation in compound f is hydrogenated by treatment with hydrogen in the presence of a suitable platinum or palladium catalyst, to provide ester compound g.

In step 4, the compound g is subject to reduction, followed by alkylsulfonylation, to afford sulfonate compound h. This step may be carried out by treatment of compound g with reducing agent such as lithium aluminum hydride to form an alcohol (not shown), which is then treated with alkylsulfonyl halide such as methanesulfonyl chloride.

Amination of arylsulfonate compound h in step 5 provides amine compound i. This amination in many embodiments may comprise treatment of sulfonate compound h with sodium azide to form an azido compound (not shown), which is then reduced, using lithium aluminum hydride or like reducing agent, followed by acid workup to yield amine i.

As in the case of Scheme A, many variations on the procedure of Scheme B are possible and will suggest themselves to those skilled in the art. In on such variation, sulfonate compound h may be treated with cyanide to form a nitrile compound, which in turn is reduced to provide an amine. Amino compound i may be subject to further reaction to afford monoalkylamino, dialkylamino, amidinyl, guanidinyl, imidazolinyl, imidazolinylamino, and other functionalities as related above. Specific details for producing compounds of formula I are described in the Examples section below.

Utility

The compounds of the invention have selective affinity for 5-HT receptors, including the $5-HT_6$ the $5-HT_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding and functional assays are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about, seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

Abbreviations

DCM dichloromethane/methylene chloride
DMF N,N-dimethylformamide
DMAP 4-dimethylaminopyridine
EtOAc ethyl acetate
EtOH ethanol
tBuOH tert-butanol
gc gas chromatography
HMPA hexamethylphosphoramide
hplc high performance liquid chromatography
mCPBA m-chloroperbenzoic acid
MeCN acetonitrile
NMP N-methyl pyrrolidinone
TEA triethylamine
TFA trifluoroacetic acid
THF tetrahydrofuran
LDA lithium diisopropylamine
TLC thin layer chromatography

Preparation 1

6-Benzenesulfonyl-3,4-dihydro-2H-naphthalen-1-one

The synthetic procedure described in this Preparation was carried out according to the process shown in Scheme C.

SCHEME C

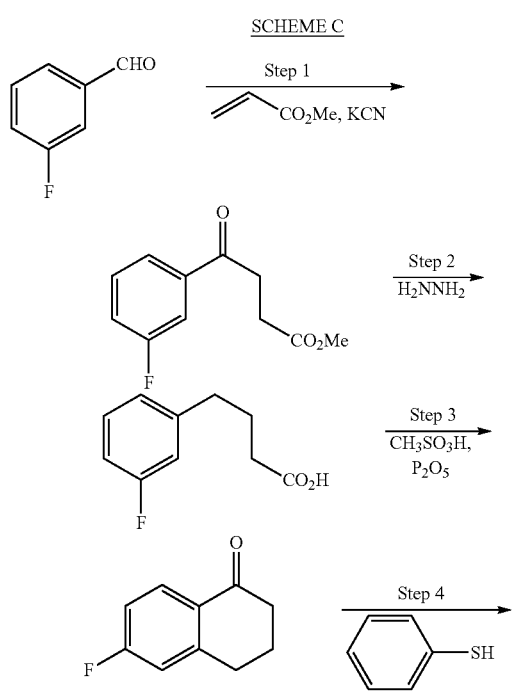

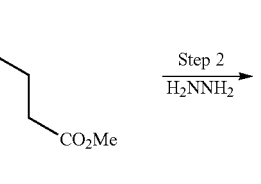

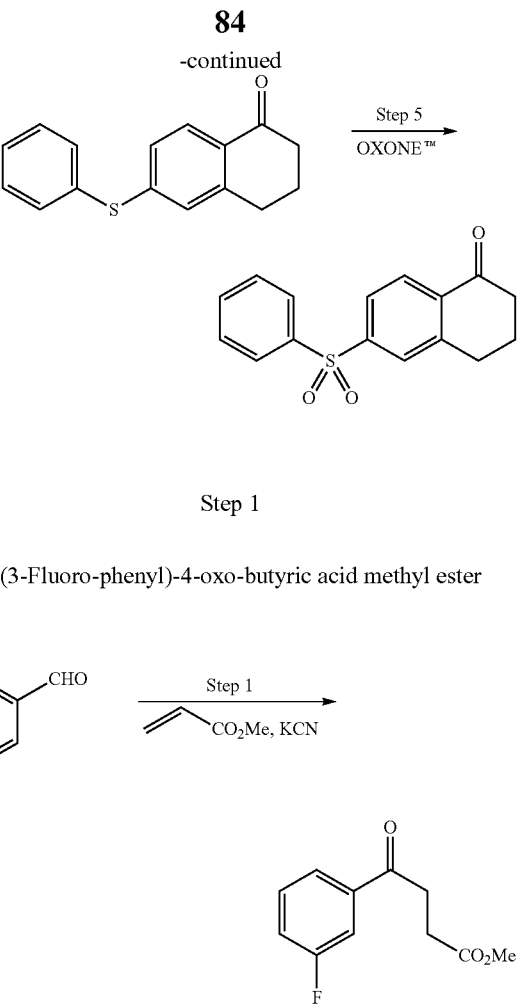

Step 1

4-(3-Fluoro-phenyl)-4-oxo-butyric acid methyl ester

A solution of 3-fluorobenzaldehyde (35.38 g, 285.07 mmol) in 35 mL dimethylformamide (DMF) was added to a heated (48° C.) solution of methyl acrylate (26.28 mL, 25.03 g, 290.7 mmol) and powdered KCN under Argon. The reaction mixture was stirred at 40° C. for 2 hours and then poured into 500 mL of water. This aqueous phase was extracted twice with 500 mL of Et$_2$O and once with 250 mL of EtOAc. The combined organic layers were washed with water and saturated brine, and then dried over MgSO$_4$. The solvent was evaporated under reduced pressure to give 50.89 g (242.2 mmol, 84.93%) of 4-(3-fluoro-phenyl)-4-oxo-butyric acid methyl ester as an oil. MS: 211 (M+H)$^+$.

Step 2

4-(3-Fluoro-phenyl)-butyric acid

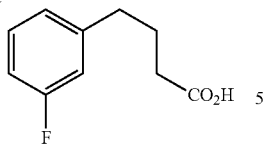

A solution of 4-(3-fluoro-phenyl)-4-oxo-butyric acid methyl ester (28.27 g, 134.49 mmol), hydrazine monohydrate (26.1 mL, 26.93 g, 537.96 mmol) and KOH (22.64 g, 403.47 mmol) in ethylene glycol (150 mL) was heated to reflux under argon and refluxed for 2 hours. The reaction mixture was cooled and diluted with 1.5 liters of water, 500 mL of Et$_2$O was added, and the mixtures was acidified by addition of 6 M HCl with stirring, after which an additional 500 mL of Et$_2$O was added. The organic layer was removed and the aqueous layer was extracted twice with 250 mL of 500 mL of Et$_2$O/EtOAc (3:1). The combined organic layers were washed with water, saturated brine, and then dried over MgSO$_4$. The solvent was evaporated under reduced pressure to yield a brownish oil, which was eluted through silica gel using hexanes/EtOAc (9:1). Removal of solvent under reduced pressure yielded 18.44 g (101.21 mmol, 75.26%) of 4-(3-fluoro-phenyl)-butyric acid as an oil. MS: 183 (M+H)$^+$.

Step 3

6-Fluoro-3,4-dihydro-2H-naphthalen-1-one

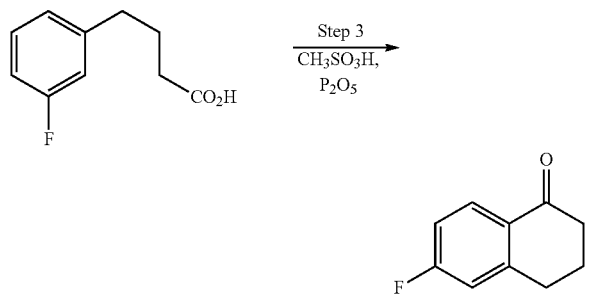

A solution of methanesulfonic acid (75 mL) and P$_2$O$_5$ was stirred at 85° C. for 15 minutes, at which point most of the P$_2$O$_5$ had dissolved. An additional 15 mL of methanesulfonic acid was added dropwise, and the mixture was stirred at 85° C. for 2 hours. The reaction mixture was poured into 500 mL of water and extracted twice with 400 mL of EtOAc. The combined organic layers were washed with saturated NaHCO$_3$, water, and saturated brine, and then dried over MgSO$_4$. The solvent was removed under reduced pressure to give an oil that was eluted through silica gel using hexanes/EtOAc (9:1). Removal of solvent under reduced pressure yielded 6.06 g, 36.91 mmol, 53.97%) of 6-fluoro-3,4-dihydro-2H-naphthalen-1-one as a yellow oil. MS: 165 (M+H)$^+$.

Step 4

6-Phenylsulfanyl-3,4-dihydro-2H-naphthalen-1-one

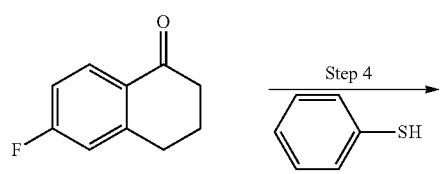

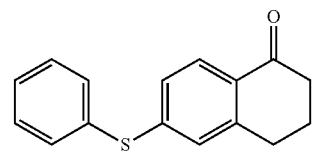

A solution of 6-fluoro-3,4-dihydro-2H-naphthalen-1-one (5.51 g, 33.56 mmol), benzenethiol (4.07 g, 3.79 mL, 36.92 mmol) and K$_2$CO$_3$ (9.28 g, 67.12 mmol) in 50 mL of N-methyl pyrrolidinone (NMP) was heated to 80° C. under argon and stirred at 80° C. for 2 hours. The reaction mixture was poured into 500 mL of water and diluted with 300 mL of EtOAc. The layers were separated and the aqueous layer was extracted twice with 250 mL of EtOAc. The combined organic layers were washed with water, saturated brine, and then dried over MgSO$_4$. The solvent was removed under reduced pressure to yield an oil which was eluted through silica gel using hexanes/EtOAc (9:1). Removal of solvent under reduced pressure provided 8.05 g (31.65 mmol, 94.31%) of 6-phenylsulfanyl-3,4-dihydro-2H-naphthalen-1-one as a pale yellow oil. MS: 255 (M+H)$^+$.

Step 5

6-Benzenesulfonyl-3,4-dihydro-2H-naphthalen-1-one

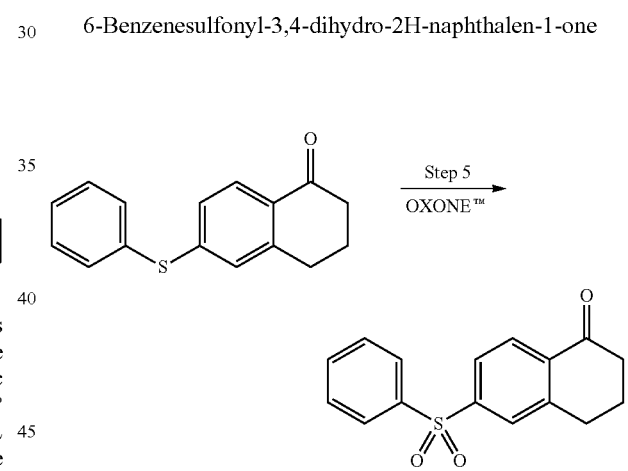

A solution of 6-phenylsulfanyl-3,4-dihydro-2H-naphthalen-1-one (8.05 g, 31.65 mmol) in MeOH/MeCN (50 mL of each) was stirred at room temperature. OXONE™ (potassium peroxymonosulfate, 77.83 g, 126.60 mmol) was dissolved in 50 mL of water and was added to the stirring reaction. The reaction mixture was stirred for 15 hours, and then evaporated under reduced pressure. The resulting aqueous residue was diluted with 500 mL of water and extracted three times with 300 mL of EtOAc. The combined extracts were washed with water, saturated brine, and dried over MgSO$_4$. The solvent was removed under reduced pressure to yield an oil which was eluted through silica gel with hexane followed by chloroform. Removal of solvent under reduced pressure afforded 6.55 g (22.87 mmol, 72.27%) of a white solid, which was recrystallized from EtO$_2$/hexanes. MS: 287 (M+H)$^+$.

Similarly prepared using the above procedure with 3-chlorobenzenethiol in step 4, was 6-(3-chloro-benzenesulfonyl)-3,4-dihydro-2H-naphthalen-1-one. MS: 287 (M+H)$^+$.

Preparation 2

7-Benzenesulfonyl-3,4-dihydro-2H-naphthalen-1-one

The synthetic procedure described in this Preparation was carried out according to the process shown in Scheme D.

SCHEME D

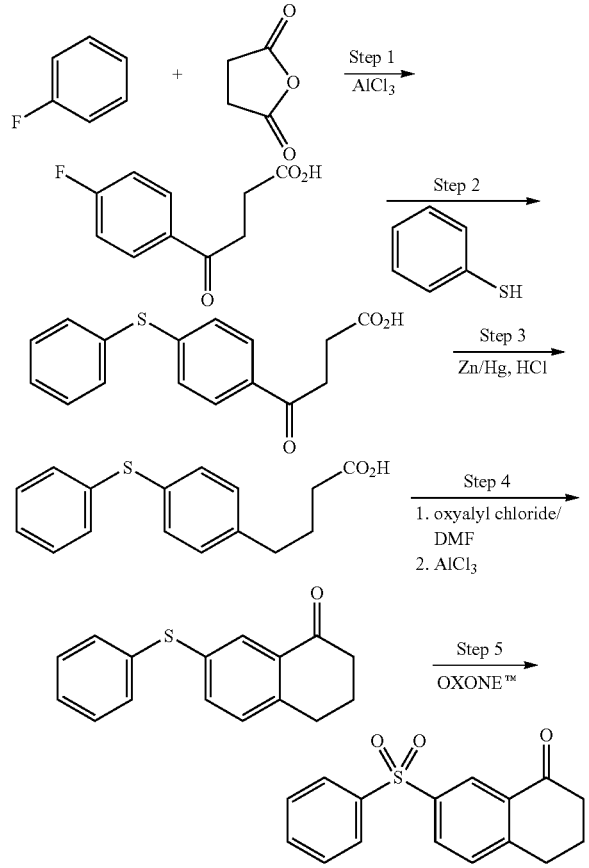

Step 1

4-(4-Fluoro-phenyl)-4-oxo-butyric acid

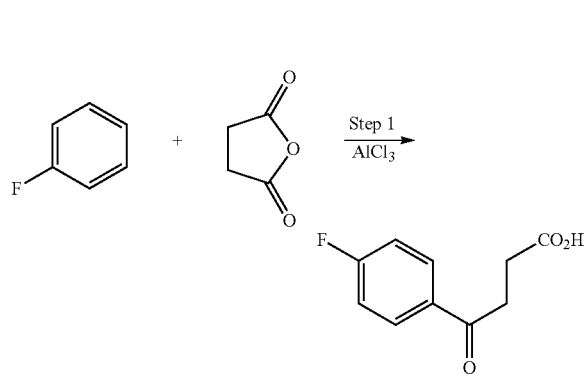

Fluorobenzene (50 mL, 530 mmol) and aluminum trichloride (156 g, 1.17 mol) were added to 500 mL of methylene chloride, and the reaction mixture was stirred. Succinic anhydride (50 g, 500 mmol) was added to the stirring reaction mixture all at once, and the reaction mixture was stirred at room temperature for 2 hours. The reaction was quenched by cautious addition of 10% HCl, and the reaction mixture was added to 500 mL of water. The aqueous mixture was extracted twice with 250 mL of methylene chloride, and the combined organic layers were dried (MgSO$_4$), and evaporated under reduced pressure to give 62 g (316 mmol, 59.6%) of 4-(4-fluoro-phenyl)-4-oxo-butyric acid as a crude solid. MS: 197 (M+H)$^+$.

Step 2

4-Oxo-4-(4-phenylsulfanyl-phenyl)-butyric acid

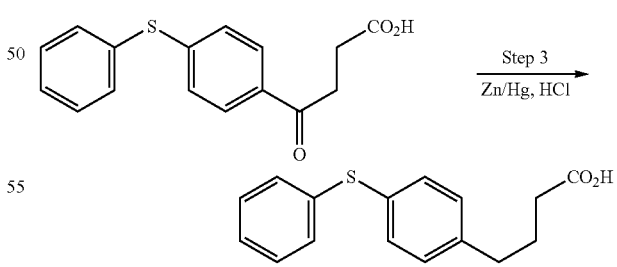

4-(4-Fluoro-phenyl)-4-oxo-butyric acid (10.0 g, 51 mmol), thiophenol (5.2 g, 51 mmol), thiophenol (5.2 g, 51 mmol) and powdered potassium carbonate (13.8 g, 100 mmol) were added to 25 mL of dimethyl sulfoxide (DMSO). The reaction mixture was heated to 110° C. for 2 hours, then cooled and diluted by addition of 250 mL water. The aqueous mixture was extracted three times with 100 mL of EtOAc, and the combined organic layers were dried (MgSO$_4$), and evaporated under reduced pressure to yield 11 g (38.5 mmol, 75.5%) of 4-oxo-4-(4-phenylsulfanyl-phenyl)-butyric acid as a crude solid. MS: 287 (M+H)$^+$.

Step 3

4-(4-Phenylsulfanyl-phenyl)-butyric acid

Powdered Zinc (66 g) was washed with 2% HCl, added to a solution of HgCl$_2$ (6 g) in 50 mL of 6M HCl. This mixture was shaken vigorously for 5 minutes, and excess liquid was decanted. The mixture was then added to a mechanically stirred suspension of 4-oxo-4-(4-phenylsulfanyl-phenyl)-butyric acid (6.5 g, 22.7 mmol) in 450 mL of 6M HCl, and the reaction mixture was stirred at room temperature for 5 days. The mixture was then decanted to remove excess HCl, and quenched by addition of 250 mL water. The aqueous mixture was extracted three times with 100 mL of EtOAc, and the combined organic layers were dried under reduced pressure to yield 5.0 g (18.4 mmol, 81%) of 4-(4-phenylsulfanyl-phenyl)-butyric acid as a crude solid. MS: 273 (M+H)$^+$.

Step 4

7-Phenylsulfanyl-3,4-dihydro-2H-naphthalen-1-one

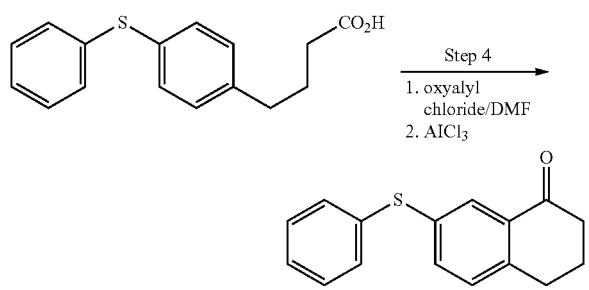

4-(4-Phenylsulfanyl-phenyl)-butyric acid (5.0 g, 18.4 mmol) was dissolved in 50 mL tetrahydrofuran (THF). Oxalyl chloride (1.8 mL, 20 mmol) and one drop of DMF were added, and the reaction mixture was stirred for 1 hour, and then evaporated to dryness under reduced pressure. The resulting residue was dissolved in 40 mL of 1,2-dichloroethane, and aluminum trichloride (0.85 g, 25 mmol) was added all at once. The reaction mixture was stirred for 1 hour, and quenched by addition of 2% HCl. This aqueous mixture was extracted twice with 100 mL of EtOAc, and the combined organic layers were dried (MgSO$_4$) and evaporated to yield 2.54 g (10 mmol, 55.5%) of 7-phenylsulfanyl-3,4-dihydro-2H-naphthalen-1-one as a gummy residue. MS: 255 (M+H)$^+$.

Step 5

7-Benzenesulfonyl-3,4-dihydro-2H-naphthalen-1-one

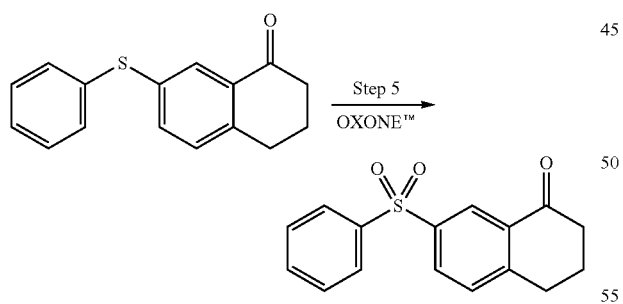

7-Phenylsulfanyl-3,4-dihydro-2H-naphthalen-1-one ( ) was dissolved in 50 mL of MeOH and stirred at room temperature. OXONE™ (13.5 g, 22 mmol) was dissolved in 10 mL of water and added to the stirring reaction. The reaction mixture was stirred for 8 hours, and then evaporated under reduced pressure. The resulting aqueous residue was diluted with 200 mL of water and extracted three times with 100 mL of EtOAc. The combined extracts were dried over MgSO$_4$, and the solvent was removed under reduced pressure to yield an oil which was eluted through silica gel with 1:1 EtOAc/hexanes. Removal of solvent under reduced pressure afforded 1.7 g (5.9 mmol, 59%) of 7-benzenesulfonyl-3,4-dihydro-2H-naphthalen-1-one as an oil. MS: 287 (M+H)$^+$.

Similarly prepared using the above procedure with 4-fluorobenzenethiol in step 2, was 7-(4-fluoro-benzenesulfonyl)-3,4-dihydro-2H-naphthalen-1-one. MS: 287 (M+H)$^+$.

Preparation 3

5-Phenylsulfonyl-indan-1-one

The synthetic procedure described in this Preparation was carried out according to the process shown in Scheme E.

SCHEME E

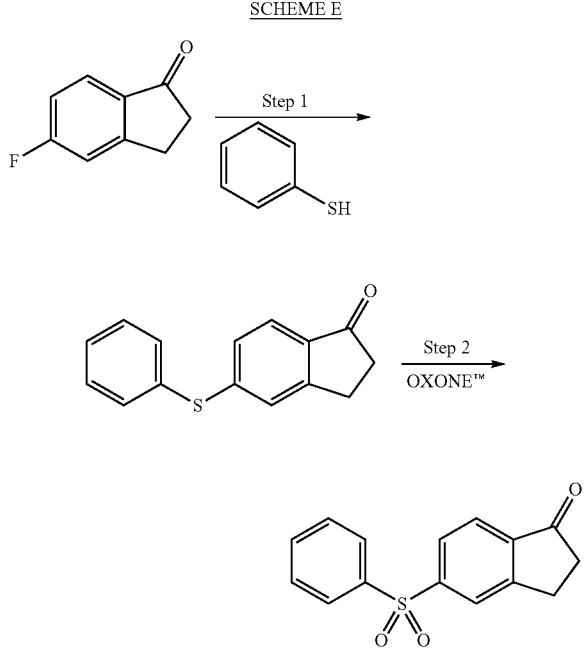

Step 1

5-Phenylsulfanyl-indan-1-one

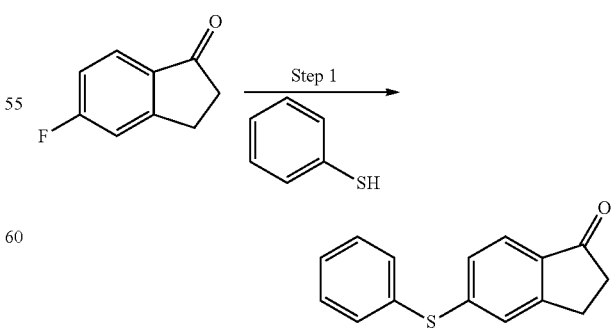

5-Fluoro-1-indanone from Aldrich Sigma Chemical Co. (Cat No. 18,566-3) was treated with benzenethiol in the presence of potassium carbonate using the procedure of step 4 of Example 1 to afford 5-phenylsulfanyl-indan-1-one. MS: 241 (M+H)⁺.

Step 2

5-Phenylsulfonyl-indan-1-one

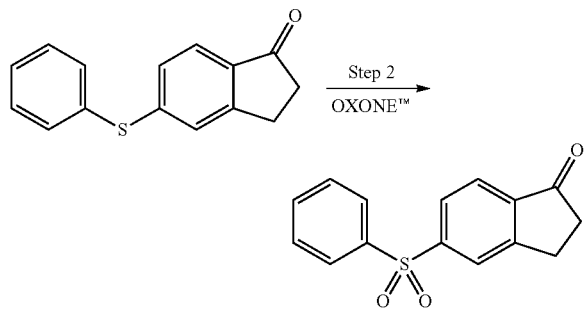

5-Phenylsulfanyl-indan-1-one was treated with OXONE™ using the procedure of step 5 of Preparation 1 to afford 5-phenylsulfonyl-indan-1-one. MS: 273 (M+H)⁺.

Example 1

C-(6-Benzenesulfonyl-1,2,3,4-tetrahydro-naphthalen-1-yl)-methylamine

The synthetic procedure described in this Example was carried out according to the process shown in Scheme F.

SCHEME F

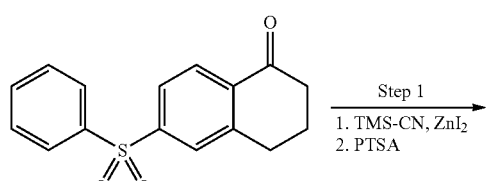

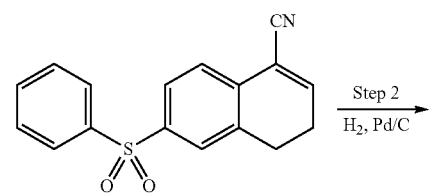

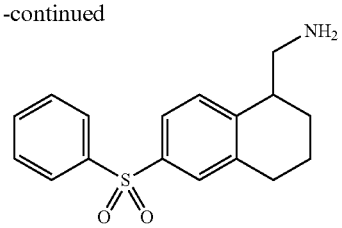

Step 1

6-Benzenesulfonyl-3,4-dihydro-naphthalene-1-carbontrile

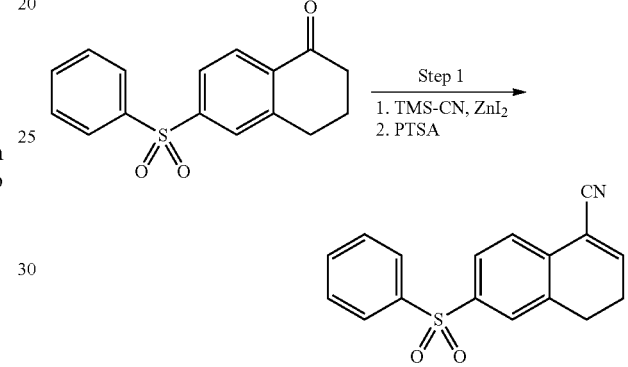

6-Benzenesulfonyl-3,4-dihydro-2H-naphthalen-1-one from Preparation 1 above (4.0 g, 14 mmol), trimethylsilyl cyanide (10.0 g, 100 mmol) and Zinc Iodide (0.25 g) were combined and stirred under nitrogen for 15 hours. The reaction mixture was then diluted by addition of 200 mL of Et₂O, washed with cold water, and the organic layer was dried (MgSO₄) and evaporated under reduced pressure to an oil. The oil was dissolved in 250 mL of toluene, and 0.5 g of paratoluene sulfonic acid was added. The reaction mixture was refluxed for three hours, cooled, and the the solvent was removed under reduced pressure. The crude product was eluted through silica under medium pressure with 5% EtOAc in hexanes to yield 1.8 g (6.1 mmol, 44%) of (racemic) 6-benzenesulfonyl-3,4-dihydro-naphthalene-1-carbonitrile as an oil. MS: 296 (M+H)⁺.

Step 2

6-Benzenesulfonyl-1,2,3,4-tetrahydro-naphthalene-1-carbonitrile

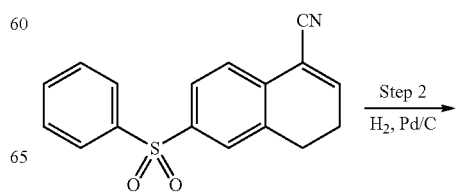

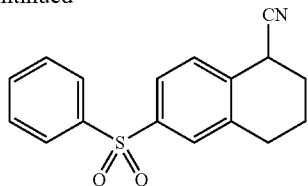

6-Benzenesulfonyl-3,4-dihydro-naphthalene-1-carbonitrile (5.1 g, 17.2 mmol), 70 mL EtOH, and 50 mL acetic acid were placed in a Parr vessel, and 1.0 g of 10% Palladium on carbon (Fluka Chemica Co.) was added. The reaction mixture was shaken for 15 hours under 55 psi hydrogen. The Parr vessel was purged with nitrogen and the reaction mixture was filtered. The filtrate was added to 500 mL water, and the aqueous mixture was extracted twice with 200 mL of EtOAc. The combined organic layers were dried (MgSO$_4$) and evaporated to yield 4.6 g (15.5 mmol, 90%) of 6-benzenesulfonyl-1,2,3,4-tetrahydro-naphthalene-1-carbonitrile as an oil. MS: 298 (M+H)$^+$.

Step 3

C-(6-Benzenesulfonyl-1,2,3,4-tetrahydro-naphthalen-1-yl)-methylamine

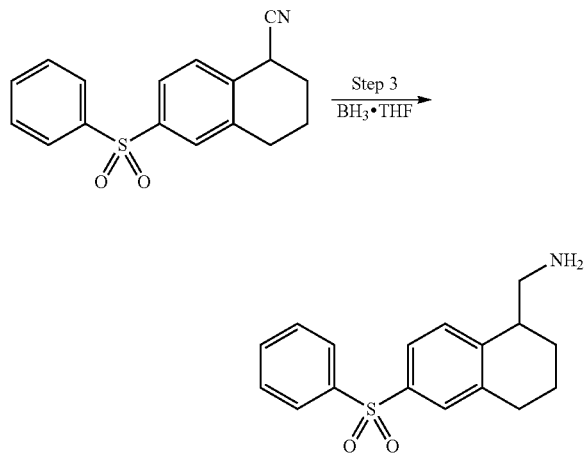

6-Benzenesulfonyl-1,2,3,4-tetrahydro-naphthalene-1-carbonitrile was dissolved in 100 mL of dry tetrahydrofuran (THF), and the mixture was stirred while cooling in an ice bath. Borane-THF complex (40 mL) was added to the cold, stirring solution, and the reaction mixture was stirred under nitrogen for 15 hours at room temperature. The reaction mixture was carefully quenched by addition of 20 mL of 20% HCl and 60 mL of methanol. The solvents were removed under reduced pressure, and the aqueous residue was treated dropwise with 1M NaOH until basic. The residue was extracted twice with 100 mL of EtOAc and the organic layers were dried (MgSO$_4$) and evaporated. The crude product was acidified with dilute HCl in EtOH and recrystallized from EtOAc to yield 3.1 g of C-(6-benzenesulfonyl-1,2,3,4-tetrahydro-naphthalen-1-yl)-methylamine as a hydrochloride salt. MS: 302 (M+H)$^+$.

Similarly prepared, using the appropriate naphthalenone compound in step 1, were:

2-(7-Benzenesulfonyl-1,2,3,4-tetrahydro-naphthalen-1-yl)-ethylamine, MS: 302 (M+H)$^+$;

C-[6-(3-Chloro-benzenesulfonyl)-1,2,3,4-tetrahydro-naphthalen-1-yl]-methylamine, MS: 337 (M+H)$^+$; and C-[7-(4-Fluoro-benzenesulfonyl)-1,2,3,4-tetrahydro-naphthalen-1-yl]-methylamine, MS: 320 (M+H)$^+$.

Example 2

[6-(3-Chloro-benzenesulfonyl)-1,2,3,4-tetrahydro-naphthalen-1-ylmethyl]-methyl-amine The synthetic procedure described in this Example was carried out according to the process shown in Scheme G.

SCHEME G

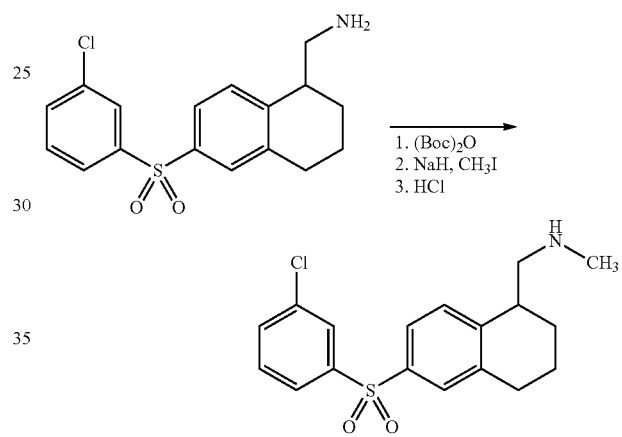

C-[6-(3-Chloro-benzenesulfonyl)-1,2,3,4-tetrahydro-naphthalen-1-yl]-methylamine (1.1 g, 3.2 mmol) and di-tert-butyl dicarbonate (DiBOC, 0.8 g, 3.7 mmol) were dissolved in 50 mL of dry THF, and this reaction mixture was stirred for 3 hours at room temperature (25° C.) under nitrogen. The solvent was evaporated under reduced pressure and the residue was dissolved in 50 mL of Et$_2$O and filtered. The filtrate was evaporated under reduced pressure to yield the BOC-protected C-[6-(3-chloro-benzenesulfonyl)-1,2,3,4-tetrahydro-naphthalen-1-yl]-methylamine, which was directly dissolved in dry dimethyl formamide (20 mL) and cooled in an ice bath. Sodium hydride (0.17 g, 60% weight in oil, approx. 4.3 mmol) was washed with hexanes, and the washed solid was added to the reaction mixture. The reaction mixture was stirred for three hours at ice bath temperature, after which 0.25 mL (4.0 mmol) of iodomethane was added. Stirring was continued for another three hours, and the reaction mixture was by addition of 250 mL of cold 0.5% aqueous HCl. The aqueous mixture was extracted twice with 100 mL of Et$_2$O, and the combined organic layers were dried (MgSO$_4$) and evaporated under reduced pressure to yield an oil. This oil was dissolved in 20 mL of THF and 20 mL of HCl in Et$_2$O was added. The solvents were evaporated, and the resulting solid was reqcyrstallized from EtOH-Et$_2$O to yield 0.3 g of [6-(3-chloro-benzenesulfonyl)-1,2,3,4-tetrahydro-naphthalen-1-ylmethyl]-methyl-amine as a hydrochloride salt. MS: 351 (M+H)$^+$.

Example 3

N-(6-Benzenesulfonyl-1,2,3,4-tetrahydro-naphthalen-1-ylmethyl)-acetamidine

The synthetic procedure described in this Example was carried out according to the process shown in Scheme H.

SCHEME H

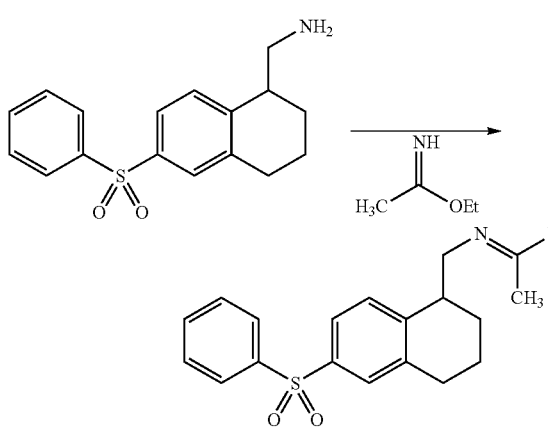

C-(6-benzenesulfonyl-1,2,3,4-tetrahydro-naphthalen-1-yl)-methylamine (0.4 g, 1.32 mmol) and ethyl imidate (acetimidic acid ethyl ester, 0.17 g, 1.32 mmol) were dissolved in 10 mL of absolute ethanol, and the reaction mixture was stirred for 8 hours under argon at room temperature. The solvent was removed under reduced pressure to yield a crude oil, which was recrystallized from Et$_2$O/EtOH as an oxalate salt. MS: 343 (M+H)$^+$.

Example 4

N-(6-Benzenesulfonyl-1,2,3,4-tetrahydro-naphthalen-1-ylmethyl)-guanidine

The synthetic procedure described in this Example was carried out according to the process shown in Scheme I.

SCHEME I

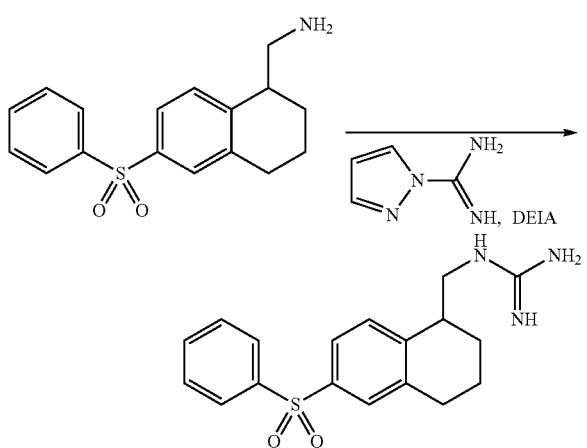

C-(6-Benzenesulfonyl-1,2,3,4-tetrahydro-naphthalen-1-yl)-methylamine (1.0 g, 3.5 mmol), 1H-pyrazol-1-carboxamidine hydrochloride (0.5 g, 3.5 mmol) and 1.2 mL of diethyl isopropylamine (7.0 nnol) were dissolved in 10 mL of DMF. The reaction mixture was heated to 100° C. for three hours and then cooled and diluted by addition of 75 mL of water. The aqueous mixture was extracted twice with 100 mL of EtOAc, and the combined organic layers were dried over MgSO$_4$. The solvent was removed under reduced pressure, and the resulting oil was purified by medium pressure chromatography (silica gel, MeOH/CHCl$_3$/NH$_4$OH 10:89:1) to yield 0.4 g (1.16 mmol, 33%) of N-(6-benzenesulfonyl-1,2,3,4-tetrahydro-naphthalen-1-ylmethyl)-guanidine, MS: 344 (M+H)$^+$.

Example 5

(6-Benzenesulfonyl-1,2,3,4-tetrahydro-naphthalen-1-ylmethyl)-(4,5-dihydro-1H-imidazol-2-yl)-amine The synthetic procedure described in this Example was carried out according to the process shown in Scheme J.

SCHEME J

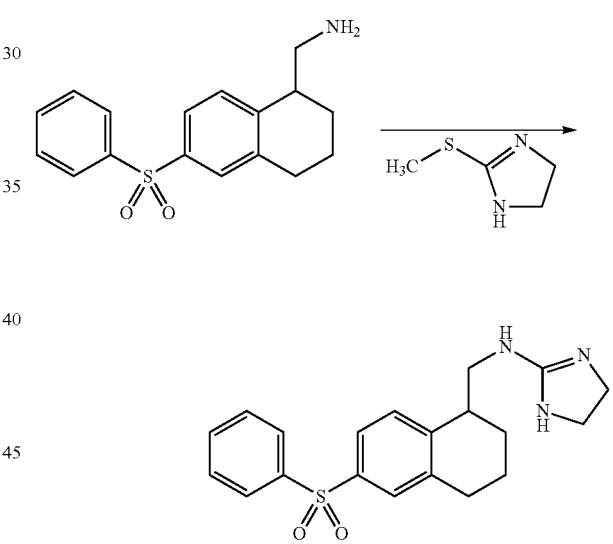

C-(6-Benzenesulfonyl-1,2,3,4-tetrahydro-naphthalen-1-yl)-methylamine (100 mg, 0.31 mmol) and 2-methylsulfanyl-4,5-dihydro-1H-imidazole hydroiodide (76 mg, 0.31 mmol) were added to 2 mL CH$_2$Cl$_2$, and the reaction mixture was heated to gentle reflux until all of the solvent was evaporated. The reaction mixture was heated to 150° C. for 30 minutes and then cooled. The crude mixture was basified by dropwise addition of aqueous NaOH solution, and then purified by preparative liquid chromatography (CH$_2$Cl$_2$/MeOH 90:10) on a short silica gel column. Removal of the solvent afforded 57 mg (47%) of (6-Benzenesulfonyl-1,2,3,4-tetrahydro-naphthalen-1-ylmethyl)-(4,5-dihydro-1H-imidazol-2-yl)-amine. MS: 370 (M+H)$^+$.

Example 6

(7-Benzenesulfonyl-1,2,3,4-tetrahydro-naphthalen-1-ylmethyl)-(5,5-dimethyl-1,4,5,6-tetrahydro-pyrimidin-2-yl)-amine The synthetic procedure described in this Example was carried out according to the process shown in Scheme K.

SCHEME K

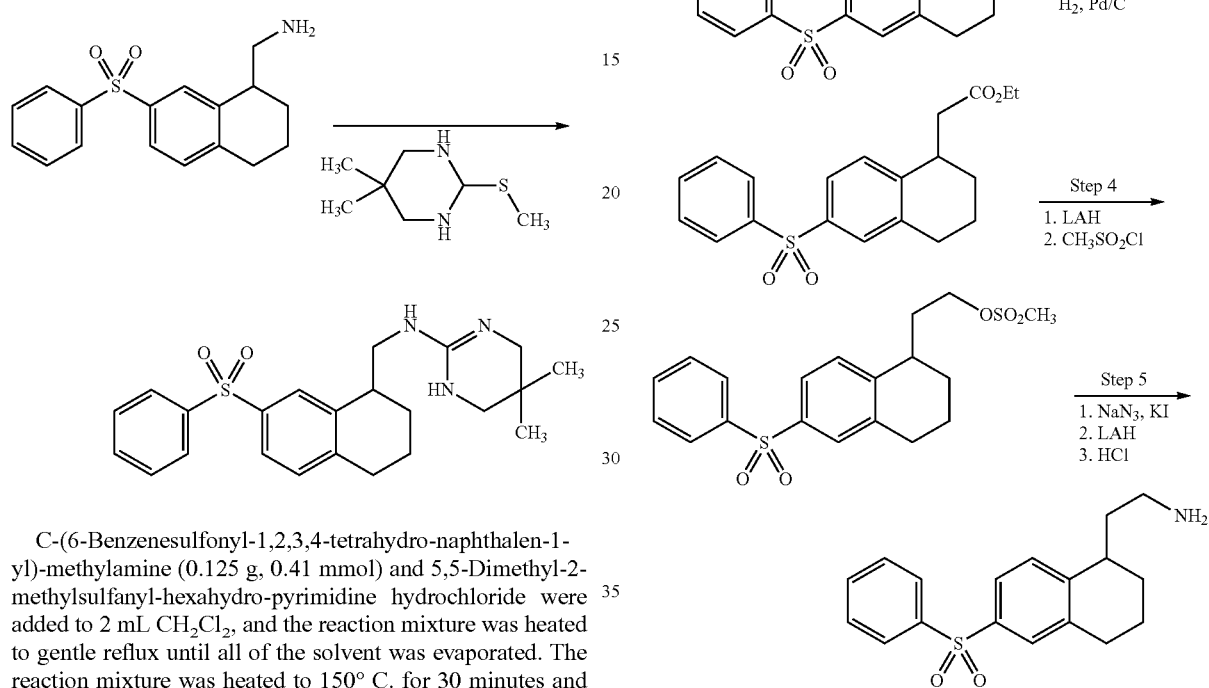

C-(6-Benzenesulfonyl-1,2,3,4-tetrahydro-naphthalen-1-yl)-methylamine (0.125 g, 0.41 mmol) and 5,5-Dimethyl-2-methylsulfanyl-hexahydro-pyrimidine hydrochloride were added to 2 mL CH$_2$Cl$_2$, and the reaction mixture was heated to gentle reflux until all of the solvent was evaporated. The reaction mixture was heated to 150° C. for 30 minutes and then cooled. The crude mixture was basified by dropwise addition of aqueous NaOH solution, and then purified by preparative liquid chromatography (CH$_2$Cl$_2$/MeOH 90:10) and recrystallized from CH$_2$Cl$_2$/ether to afford 58 mg (31%) of (7-Benzenesulfonyl-1,2,3,4-tetrahydro-naphthalen-1-ylmethyl)-(5,5-dimethyl-1,4,5,6-tetrahydro-pyrimidin-2-yl)-amine. MP: 140-145° C. MS: 413 (M+H)$^+$.

Example 7

2-(6-Benzenesulfonyl-1,2,3,4-tetrahydro-naphthalen-1-yl)-ethylamine

The synthetic procedure described in this Example was carried out according to the process shown in Scheme L.

SCHEME L

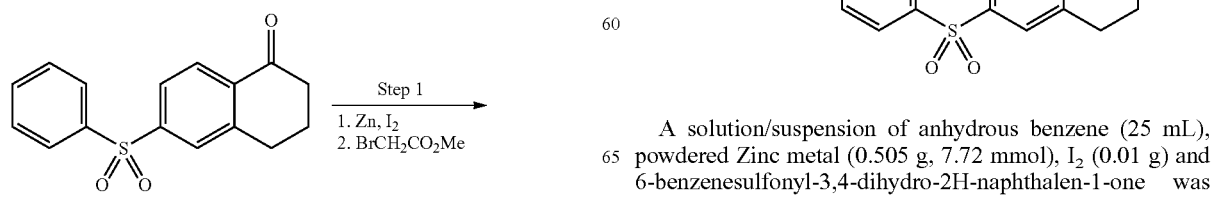

Step 1

(6-Benzenesulfonyl-1-hydroxy-1,2,3,4-tetrahydro-naphthalen-1-yl)-acetic acid methyl ester A solution/suspension of anhydrous benzene (25 mL), powdered Zinc metal (0.505 g, 7.72 mmol), I$_2$ (0.01 g) and 6-benzenesulfonyl-3,4-dihydro-2H-naphthalen-1-one was stirred for 10 minutes at room temperature. Ethyl bromopropionate (0.784 mL, 1.18 g, 7.07 mmol) was added and the reaction mixture was heated to reflux for 2.5 hours. The reaction mixture was allowed to cool, diluted with 300 mL of water and extracted twice with 250 mL of EtOAc. The combined organic layers were washed with water and saturated brine, dried (MgSO$_4$) and evaporated under reduced pressure to yield (6-benzenesulfonyl-1-hydroxy-1,2,3,4-tetrahydronaphthalen-1-yl)-acetic acid methyl ester. MS: 375 (M+H)$^+$.

Step 2

(6-Benzenesulfonyl-3,4-dihydro-2H-naphthalen-1-ylidene)-acetic acid methyl ester

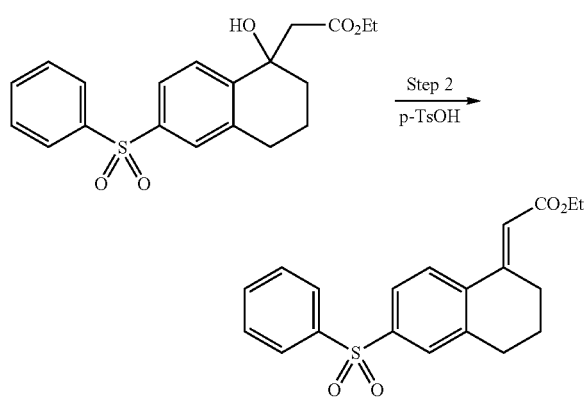

A solution of (6-benzenesulfonyl-1-hydroxy-1,2,3,4-tetrahydro-naphthalen-1-yl)-acetic acid methyl ester (1.28 g, 3.42 mmol) and para-toluenesulfonic acid (0.50 g) in 250 mL of benzene was refluxed for 2 hours using a Dean-Stark trap. The reaction mixture was cooled and poured into 500 mL of EtOAc, and this organic phase was washed with water, saturated NaHCO$_3$, and dried (MgSO$_4$). Evaporation under reduced pressure gave a dark oil that was purified by elution on silica gel (hexanes:EtOAc 7:3) to yield 0.991 g (2.78 mmol, 81.2% of a white crystalline solid. MS: 357 (M+H)$^+$.

Step 3

(6-Benzenesulfonyl-1,2,3,4-tetrahydro-naphthalen-1-yl)-acetic acid methyl ester

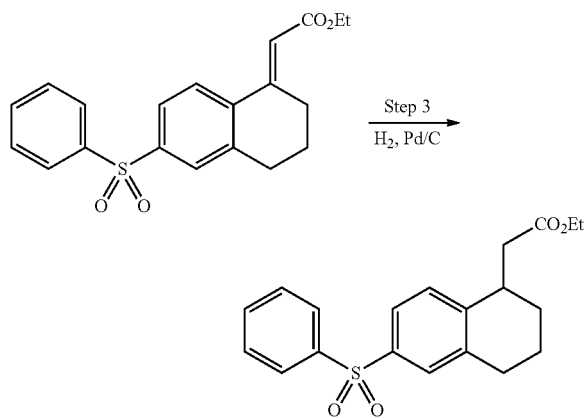

(6-Benzenesulfonyl-3,4-dihydro-2H-naphthalen-1-ylidene)-acetic acid methyl ester (5.63 g, 15.8 mmol) was dissolved in 300 mL EtOAc in a 1 L Parr vessel, and 1.0 g of palladium/activated carbon was added. The reaction mixture was shaken for 8 hours under 50 psi of hydrogen, after which the mixture was filtered through a CELITE™ plug. The filtrate was evaporated under reduced pressure to give an oil, which was dissolved in hexanes:EtOAc (3:2) and eluted through silica gel to afford 5.22 g (14.56 mmol, 92.2%) of (6-benzenesulfonyl-1,2,3,4-tetrahydro-naphthalen-1-yl)-acetic acid methyl ester. MS: 359 (M+H)$^+$.

Step 4

Methanesulfonic acid 2-(6-benzenesulfonyl-1,2,3,4-tetrahydro-naphthalen-1-yl)-ethyl ester

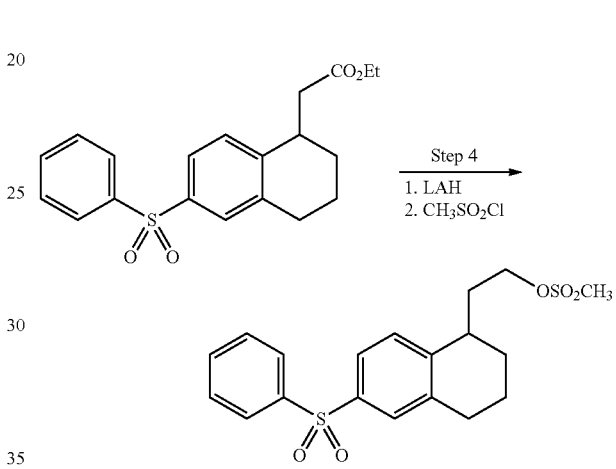

A solution of (6-benzenesulfonyl-1,2,3,4-tetrahydro-naphthalen-1-yl)-acetic acid methyl ester (5.22 g, 14.56 mmol) in anhydrous Et$_2$O (50 mL) was cooled to 0° C. under argon, and 21.84 mL of lithium aluminum hydride (21.84 mmol) in THF was added dropwise via syringe. An additional 50 mL of dry THF was added, and the reaction mixture was stirred for 1 hour. The reaction mixture was carefully quenched by addition of 500 mL water, and the resulting aqueous mixture was extracted twice with 250 mL of EtOAc. Evaporation of the organic layer yielded a crude oil which was purified by elution through silica gel with 1:1 hexanes: EtOAc. The solvent was evaporated to give a solid that was dissolved in 50 mL dry methylene chloride. The solution was cooled to 0° C., and pyridine (4.0 mL, 49.5 mmol) and methanesulfonyl chloride (1.69 mL, 21.84 mmol) were added. The reaction mixture was stirred for 3 hours, during which time the reaction mixture was allowed to warm to room temperature. The reaction mixture was poured into 500 mL of saturated aqueous NaHCO$_3$, and the mixture was extracted three times with 250 mL of EtOAc. The combined organic layers were washed with water, brine, and dried on MgSO$_4$. The solvent was removed under reduced pressure to give an oil that was dissolved in benzene and azeotroped to remove residual pyridine. Solvent was removed, and the resulting oil was dissolved in methylene chloride and eluted through silica gel with 1:1 hexanes:EtOAc. Solvent was again removed, to afford methanesulfonic acid 2-(6-benzenesulfonyl-1,2,3,4- tetrahydro-naphthalen-1-yl)-ethyl ester as a white solid (4.44 g, 11.25 mmol, 77.3%) MS: 396 (M+H)+.

Step 5

2-(6-Benzenesulfonyl-1,2,3,4-tetrahydro-naphthalen-1-yl)-ethylamine

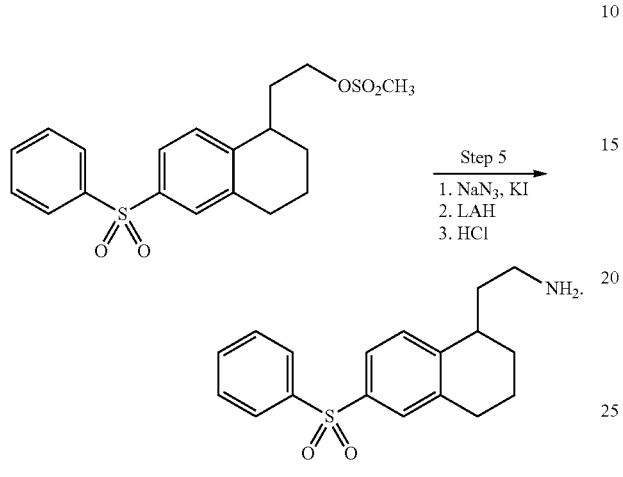

A solution of methanesulfonic acid 2-(6-benzenesulfonyl-1,2,3,4-tetrahydro-naphthalen-1-yl)-ethyl ester (1.12 g, 2.84 mmol) in thy DMF (25 mL) was stirred under argon at room temperature. Solid potassium iodide (0.25 g) and sodium azide (0.185 g, 2.84 mmol) were added, and the reaction mixture was allowed to stir for 48 hours. The reaction mixture was poured into 500 mL of water, and the aqueous mixture was extracted four times with 150 mL of EtOAc. The combined organic layers were washed with water, brine, dried (MgSO4), and evaporated under reduced pressure to give an oil that was purified by eluting through silica gel with hexanes:EtOAc (3:2). After solvent removal, the resulting oil was dissolved in dry THF, cooled to 0° C., and 5.68 mL of lithium aluminum hydride in THF (5.68 mmol) was added dropwise via syringe to the stirring reaction mixture. The reaction mixture was allowed to warm to room temperature (about 30 minutes) and was quenched by addition to 250 mL of water. The aqueous solution was extracted twice with 250 mL of EtOAc, and the combined organic layers were washed with water, brine, dried (MgSO4), and evaporated under reduced pressure to give an oil. The oil was dissolved in MeOH, 2 mL of 2M HCl in Et2O was added, and the solution was gently warmed, then cooled. The resulting residue was recrystallized from MeOH/Et2O to afford 0.17 g (0.483 mmol, 17%) of 2-(6-benzenesulfonyl-1,2,3,4-tetrahydro-naphthalen-1-yl)-ethylamine hydrochloride salt. MS: 316 (M+H)+.

Similarly prepared, using 7-benzenesulfonyl-3,4-dihydro-2H-naphthalen-1-one, 5-phenylsulfonyl-indan-1-one and 6-(2-Fluoro-benzenesulfonyl)-3,4-dihydro-2H-naphthalen-1-one respectively in step 1, were:

2-(7-Benzenesulfonyl-1,2,3,4-tetrahydro-naphthalen-1-yl)-ethylamine, MS: 316 (M+H)+.

2-(5-Benzenesulfonyl-indan-1-yl)-ethylamine, MS: 302 (M+H)+; and

2-[6-(2-Fluoro-benzenesulfonyl)-1,2,3,4-tetrahydro-naphthalen-1-yl]-ethylamine, MS: 334 (M+H)+.

Example 8

N'-[2-(7-Benzenesulfonyl-1,2,3,4-tetrahydro-naphthalen-1-yl)-ethyl]-N,N-dimethyl-acetamidine The synthetic procedure described in this Example was carried out according to the process shown in Scheme M.

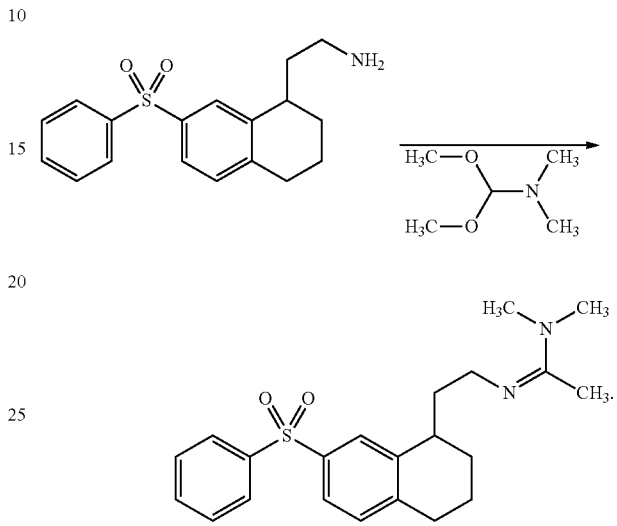

2-(6-Benzenesulfonyl-1,2,3,4-tetrahydro-naphthalen-1-yl)-ethylamine (0.1 g, 0.32 mmol) was added to 5 mL of dimethylformamide dimethyl acetal, and the reaction mixture was heated to 95° C. for two hours. The reaction mixture was cooled and quenched by addition of 100 mL of water. The aqueous mixture was extracted twice with 150 mL of EtOAc, and the combined organic layers were washed with water, brine, dried (MgSO4), and evaporated under reduced pressure to give an oil. The crude oil was dissolved in methylene chloride and eluted through silica gel with 1:1 hexanes:EtOAc, after which solvent was removed under reduced pressure to yield 0.1 g (0.26 mmol, 81%) of N'-[2-(7-Benzenesulfonyl-1,2,3,4-tetrahydro-naphthalen-1-yl)-ethyl]-N,N-dimethyl-acetamidine. MS: 386 (M+H)+.

Example 9

2-(6-Benzenesulfonyl-1,2,3,4-tetrahydro-naphthalen-1-yl)-ethyl]-dimethyl-amine

The synthetic procedure described in this Example was carried out according to the process shown in Scheme N.

SCHEME N

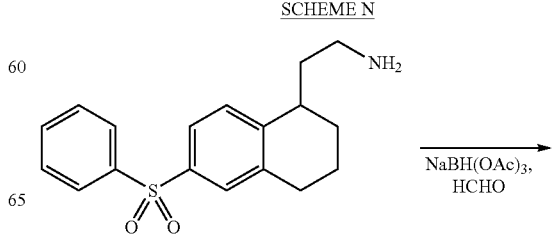

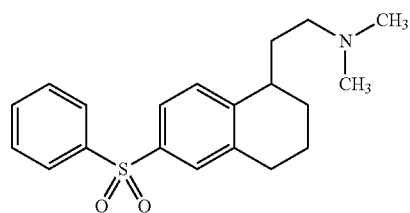

Using the procedure described *Journal of Organic Chemistry*, 61(11), 3849-3862 (1996), a solution of 0.680 g (2.16 mmol) of 2-(6-benzenesulfonyl-1,2,3,4-tetrahydro-naphthalen-1-yl)-ethylamine and aqueous formaldehyde (0:439 mL of 37% solution, 5.40 mmol) in 35 mL of 1,2-dichloroethane was stirred at room temperature for 10 minutes. NaBH(OAc)3 (2.75 g, 12.96 mmol) was added, and the reaction mixture was stirred for 2 hours at room temperature. Saturated aqueous NaHCO$_3$ was slowly added to quench the reaction, and the aqueous mixture was extracted twice with 250 mL of EtOAc. The combined organic layers were washed with water, brine, and dried (MgSO$_4$). Evaporation of the solvent under reduced pressured gave an oil that was eluted through a silica gel column with hexanes/EtOAc (6:4:) to afford 2-(6-benzenesulfonyl-1,2,3,4-tetrahydro-naphthalen-1-yl)-ethyl]-dimethyl-amine, which was recrystallized as an oxalate salt, 0.340 g (0.90 mmol, 41.6%). MS: 344 (M+H)$^+$.

Example 10

3-(6-Benzenesulfonyl-1,2,3,4-tetrahydro-naphthalen-1-yl)-propylamine

The synthetic procedure described in this Example was carried out according to the process shown in Scheme O.

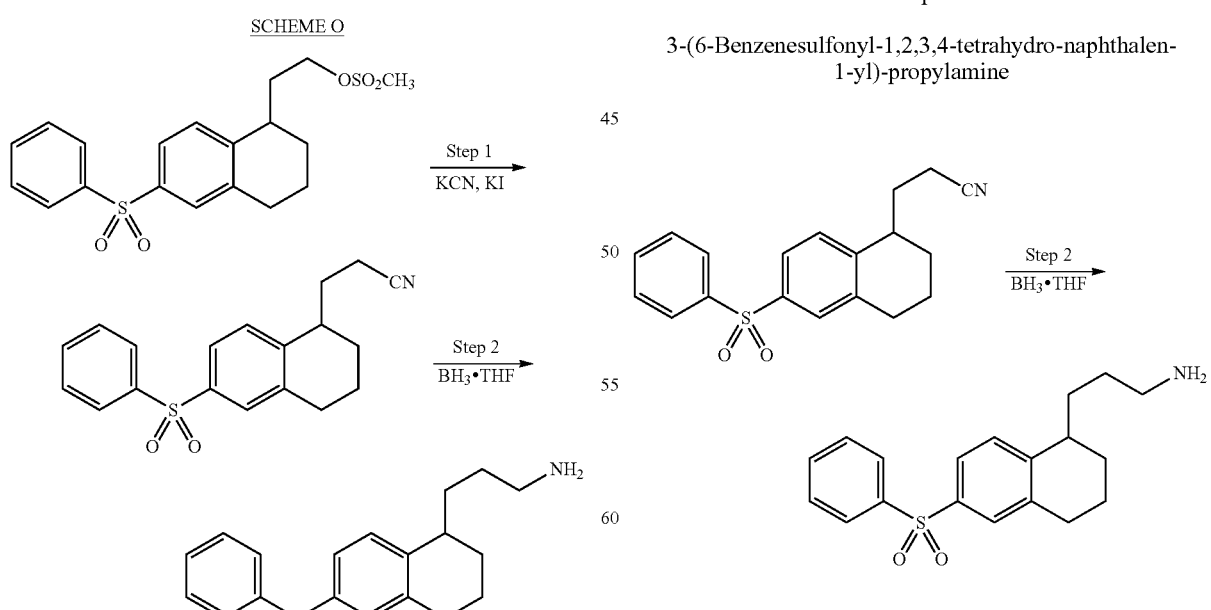

Step 1

3-(6-Benzenesulfonyl-1,2,3,4-tetrahydro-naphthalen-1-yl)-propionitrile

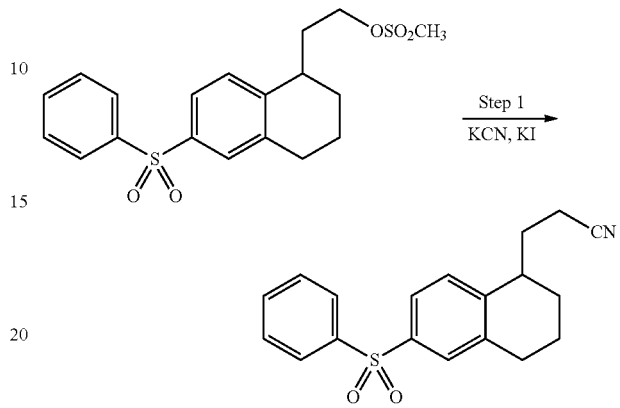

A solution of methanesulfonic acid 2-(6-benzenesulfonyl-1,2,3,4-tetrahydro-naphthalen-1-yl)-ethyl ester (1.21 g, 3.07 mmol), potassium cyanide (0.799 g, 12.27 mmol) and potassium iodide (0.25 g) in 50 mL of DMF was heated to 95° C. under argon with stirring for 24 hours. The reaction mixture was cooled and poured into 500 mL of water. The aqueous mix was extracted three times with EtOAc, and the combined organic phases were washed with water, saturated brine, and dried (MgSO$_4$). Evaporation of the solvent under reduced pressure gave an oil that was purified by elution on silica gel (hexanes:EtOAc 1:1). Removal of the solvent under reduced pressure yielded 0.950 g (2.97 mmol, 95.1% of 3-(6-benzenesulfonyl-1,2,3,4-tetrahydro-naphthalen-1-yl)-propionitrile as a white crystalline solid. MS: 326 (M+H)$^+$.

Step 2

3-(6-Benzenesulfonyl-1,2,3,4-tetrahydro-naphthalen-1-yl)-propylamine

A solution of 3-(6-benzenesulfonyl-1,2,3,4-tetrahydro-naphthalen-1-yl)-propionitrile (0.740 g, 2.27 mmol was dissolved in dry THF, and the reaction mixture was stirred under argon at room temperature. BH$_3$THF (6 mL) was added dropwise, and the reaction mixture was allowed to stir for 15 hours. The reaction mixture was quenched by careful addition of 10% aqueous HCl, followed by stirring for 10 minutes. The reaction mixture was placed under reduced pressure to remove THF. The resulting aqueous solution was diluted with 10 mL of EtOH, made basic by addition of 0.5 M NaOH solution, and warmed to 75° C. for 15 minutes. The solution was cooled and extracted three times with 150 mL of EtOAc. The combined organic layers were washed with water, saturated brine, and dried (MgSO$_4$). Evaporation of the solvent under reduced pressure gave an oil that was purified by elution on silica gel (MeOH:CHCl$_3$ 5:95). Removal of the solvent yielded 0.190 g (0.577 mmol, 25.4%) of 3-(6-benzenesulfonyl-1,2,3,4-tetrahydro-naphthalen-1-yl)-propylamine as an oil, which was recrystallized from EtOH/EtOAc as an oxalate salt (0.140 g, 0.334 mmol, 14.7% overall yield). MS: 330 (M+H)$^+$ Example 11

3-(6-Benzenesulfonyl-1,2,3,4-tetrahydro-naphthalen-1-yl)-propionamidine

The synthetic procedure described in this Example was carried out according to the process shown in Scheme P.

SCHEME P

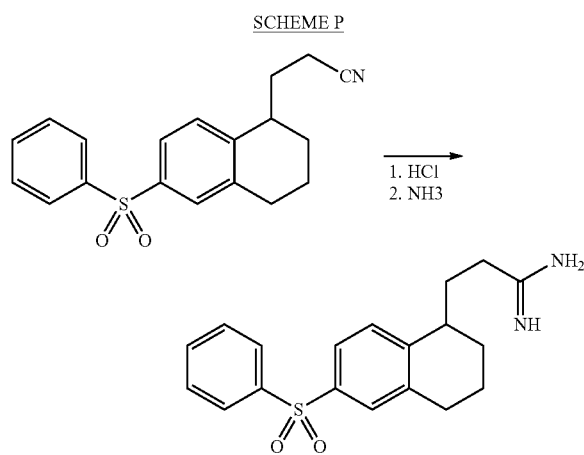

3-(6-Benzenesulfonyl-1,2,3,4-tetrahydro-naphthalen-1-yl)-propionitrile (0.45 g, 1.4 mmol) was dissolved in a mixture of 15 mL EtOH and 10 mL CHCl$_3$, and the solution was sparged with nitrogen for two minutes, and then with HCl gas for 15 minutes, after which the reaction mixture was allowed to sit under HCl gas for 48 hours. The reaction mixture was evaporated to dryness under reduced pressure, and the resulting residue was dissolved in a mixture of 15 mL EtOH and 10 mL CHCl$_3$. This solution was added dropwise to 50 mL of ice cold solution of NH$_3$ (saturated) in MeOH. The solution was filtered to remove NH$_4$Cl, concentrated under vacuum, and dissolved in a mixture of CH$_2$Cl$_2$, EtOAc and MeOH (1:1:1). NH$_4$Cl was removed from this organic solution by filtration, and the solvent was removed under reduced pressure to yield 0.32 g (0.94 mmol, 67%) of 3-(6-benzenesulfonyl-1,2,3,4-tetrahydro-naphthalen-1-yl)-propionamidine as an oil. MS: 343 (M+H)$^+$.

Example 12

1-[2-(6-Benzenesulfonyl-1,2,3,4-tetrahydro-naphthalen-1-yl)-ethyl]-1H-imidazole

The synthetic procedure described in this Example was carried out according to the process shown in Scheme P.

SCHEME Q

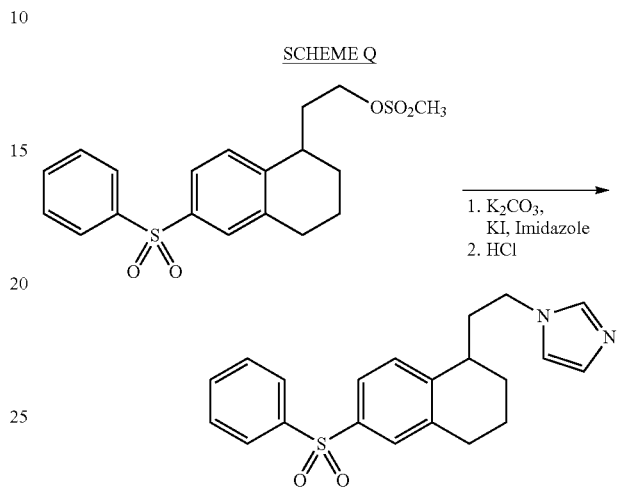

Methanesulfonic acid 2-(6-benzenesulfonyl-1,2,3,4-tetrahydro-naphthalen-1-yl)-ethyl ester (0.250 g, 0.634 mmol), imidazole (0.173 g, 2.54 mmol), potassium carbonate (0.175 g, 1.27 mmol) and potassium iodide (0.25 g) were added to 50 mL of acetonitrile, and the reaction mixture was refluxed for 16 hours under argon. The reaction mixture was cooled and poured into 300 mL of water, extracted twice with 250 mL of EtOAc, and the combined organic layers were washed with water, saturated brine, and dried (MgSO$_4$). The solvent was removed under reduced pressure to yield an oil that was purified via silica gel column, eluting with MeOH/CHCl$_3$ (5:95). Solvent was removed under reduced pressure to afford 0.180 g (0.491 mmol, 77.5% of 1-[2-(6-benzenesulfonyl-1,2,3,4-tetrahydro-naphthalen-1-yl)-ethyl]-1H-imidazole as an oil. The oil was recrystallized from EtOH/HCl to give 0.130 g of the corresponding hydrochloride salt (0.323 mol, 50.9%). MS: 367 (M+H)$^+$.

Example 13

S-(6-Benzenesulfonyl-1,2,3,4-tetrahydro-naphthalen-1-ylmethyl)-methylamine

The synthetic procedure described in this Example was carried out according to the process shown in Scheme Q.

SCHEME R

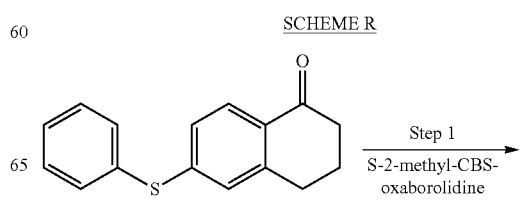

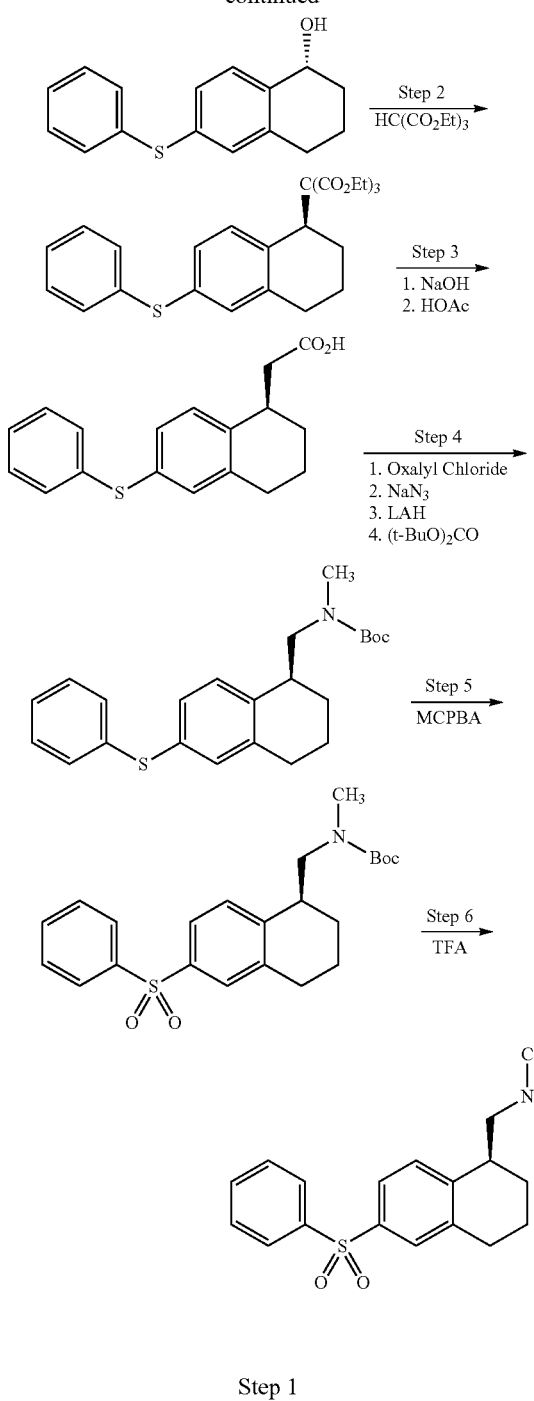

Step 1

R-6-Phenylsulfanyl-1,2,3,4-tetrahydro-naphthalen-1-ol

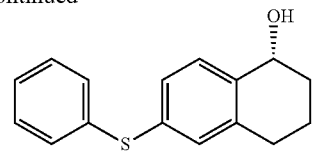

This step follows the general procedure of Salunkhe and Burkhardt, Tetrahedron Letters 38(9): 1523 (1997). A solution of 1.4 mL (1.4 mmole) 1.0M S-2-methyl-CBS-oxazaborolidine in toluene and 2.8 mL (15.8 mmole) borane-diethylaniline complex in 15 mL toluene was heated at 30° C. under a dry nitrogen atmosphere. A solution of 3.5 g (13.8 mmole) 6-phenylsulfanyl-3,4-dihydro-2H-naphthalene-1-one in 15 mL toluene was added dropwise over 2 hours. The reaction mixture was stirred at 30-32° C. for one hour. Methanol (5.0 mL) was added dropwise over 20 minutes followed by 10 mL 1.0N hydrochloric acid. The mixture was stirred for 20 minutes, then it was diluted with 50 mL ethyl ether. The organic phase was washed twice with 25 mL water, once with 20 mL saturated sodium chloride, dried (magnesium sulfate) and concentrated under reduced pressure. The residue was recrystallized from ether/hexane to give R-6-phenylsulfanyl-1,2,3,4-tetrahydro-naphthalen-1-ol, 3.49 g (98%), m.p. 74-75° C. M+H=256; [α]$_D$=−30.8° (c=1, CHCl$_3$). Chiral HPLC on a Chiracel OD (20 microns) eluting with 5% isopropyl alcohol in hexane, retention time=10.9 min, 99.9 ee.

Step 2

S-2-Ethoxycarbonyl-2-(6-phenylsulfanyl-1,2,3,4-tetrahydro-naphthalen-1-yl)-malonic acid diethyl ester

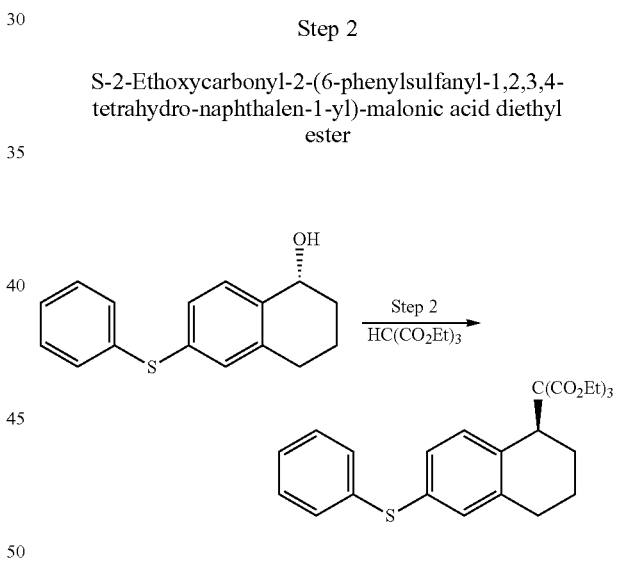

This step follows the general procedure of Hillier, et al, Organic Letters 6(4): 573 (2004). A solution of 3.3 g (12.9 mmole) R-6-phenylsulfanyl-1,2,3,4-tetrahydro-naphthalen-1-ol, 5.97 g (25.7 mmole) triethylmethane tricarboxylate and 2.3 mL (25.7 mmole) 97% trimethylphosphine in 60 mL toluene under nitrogen was cooled to −55° C. Neat diisopropylazodicarboxylate (5.06 mL, 25.7 mmole) was added dropwise over 30 minutes. The reaction mixture was stirred at −55° C. for ½ hour, then allowed to warm to 22° over 2 hours and then stirred at 22° C. for 1 hour. The solution was concentrated under reduced pressure. To the residue was added 50 mL 3N sodium hydroxide. The mixture was extracted with 200 mL diethyl ether. The organic phase was washed twice with 25 mL 3 N sodium hydroxide, once with 25 mL water, twice with 25 mL 1 N hydrochloric acid, once with 25 mL saturated sodium chloride, dried (magnesium sulfate), and concentrated under reduced pressure. The residue was triturated with 50 mL 50% ethyl ether/hexane. The precipitated diisopropylhydrazine dicarboxylic acid was removed by filtration. The filtrate was concentrated and the residue was subjected to low pressure column chromatography over silica gel 230-400 mesh eluting with 10% ethyl acetate in hexane. The product was obtained as a solid, 3.71 g (61%) which was determined by chiral HPLC (Chiralpak OJ, 10% isopropanol in hexane, retention time=10.5 minutes) to be 90 ee. An analytical sample obtained by recrystallization from ethyl ether/hexane had m.p. 85-86° C., M+H=470, [α]$_D$=+30.2° (c=1.0, CHCl$_3$), and was determined to be 98.8 ee by chiral HPLC analysis.

Step 3

R-(6-Phenylsulfanyl-1,2,3,4-tetrahydro-naphthalen-1-yl)-acetic acid

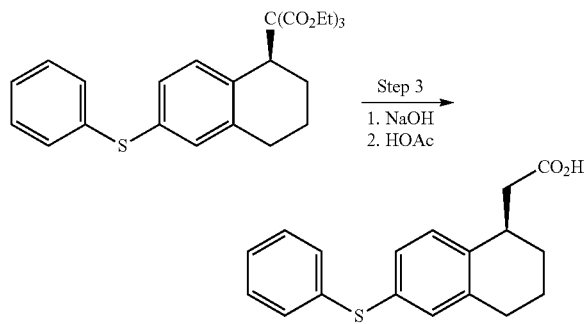

To a solution of 0.6 g (1.3 mmole) 90 ee S-2-ethoxycarbonyl-2-(6-phenylsulfanyl-1,2,3,4-tetrahydro-naphthalen-1-yl)-malonic acid diethyl ester in 10 mL methanol and 2 mL water was added 2.6 mL 3 N sodium hydroxide. The reaction mixture was heated under reflux for 18 hours. The mixture was concentrated under reduced pressure, and the residue was dissolved in 10 mL glacial acetic acid. The solution was heated under reflux for 4 hours and then it was concentrated under reduced pressure. The residue was partitioned between 20 mL 0.1 N hydrochloric acid and 30 mL ethyl acetate. The organic phase was washed with 10 mL water, 10 mL saturated sodium chloride, dried (magnesium sulfate) and concentrated under reduced pressure to yield R-(6-phenylsulfanyl-1,2,3,4-tetrahydro-naphthalen-1-yl)-acetic acid as an oil, 0.38 g (98%), M+H=299. A sample of this acid was converted to the methyl ester using trimethylsilyl diazomethane. Chiral HPLC on Chiralpak OJ, 10% isopropyl alcohol/hexane, showed 90 ee.

Step 4

S-Methyl-(6-phenylsulfanyl-1,2,3,4-tetrahydro-naphthalen-1-ylmethyl)-carbamic acid tert-butyl ester

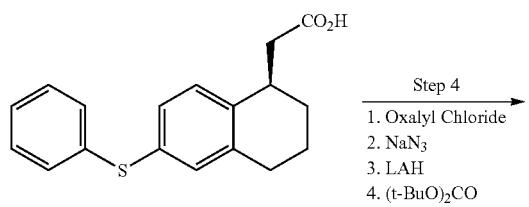

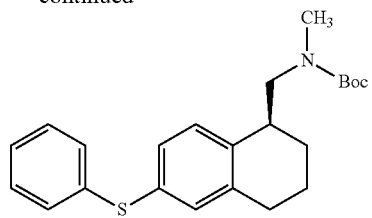

To a solution of 0.38 g (1.27 mmole) 90 ee R-(6-phenylsulfanyl-1,2,3,4-tetrahydro-naphthalen-1-yl)-acetic acid in 6 mL methylene chloride was added 2 drops DMF and 0.22 mL (2.55 mmole) oxalyl chloride. The solution was stirred at 23° C. for 30 minutes and then concentrated under reduced pressure. The residue was dissolved in 6 mL acetone and cooled to 0° C. in an ice bath. A solution of 0.206 g (3.18 mmole) sodium azide in 2 mL water was added dropwise, and the reaction mixture was stirred from 0° C. to 22° C. over 30 minutes. The mixture was diluted with 20 mL water, 25 mL saturated sodium chloride was added, and the mixture was extracted with 50 mL toluene. The organic phase was dried (magnesium sulfate) and then heated under reflux for 30 minutes. The solution was concentrated under reduced pressure and the residue was dissolved in 10 mL tetrahydrofuran. The resulting solution was added dropwise to a solution of 2.5 mL 0.2 M lithium aluminum hydride in tetrahydrofuran. The reaction mixture was stirred at 23° C. for 30 minutes, then at reflux for 20 minutes. Water was added dropwise until gas evolution ceased. The mixture was filtered and concentrated under reduced pressure, and the residue was partitioned between 20 mL 6 N hydrochloric acid and 25 mL ethyl ether. The aqueous phase was cooled in an ice bath and made strongly basic with solid sodium hydroxide pellets. The mixture was extracted with 35 mL ethyl ether, and the organic phase was dried (magnesium sulfate) and concentrated under reduced pressure. The residue was dissolved in 10 mL tetrahydrofuran and a solution of 0.12 g (0.54 mmole) di-tert-butyl dicarbonate in 2 mL tetrahydrofuran was added. The reaction mixture was stirred at 23° C. for 30 minutes and then concentrated under reduced pressure. The residue was subjected to low pressure column chromatography over silica gel 230-400 mesh eluting with 5% ethyl acetate in hexane. S-Methyl-(6-phenylsulfanyl-1,2,3,4-tetrahydro-naphthalen-1-ylmethyl)-carbamic acid tert-butyl ester was obtained as an oil, 0.13 g (27%) M+H=384.

Step 5

S-(6-Benzenesulfonyl-1,2,3,4-tetrahydro-naphthalen-1-ylmethyl)-methyl-carbamic acid tert-butyl ester

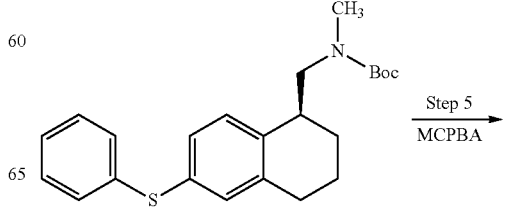

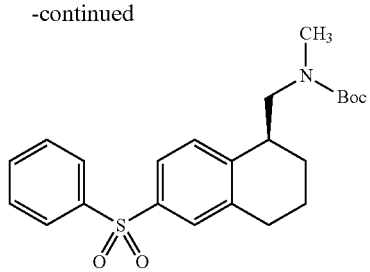

To a solution of 0.13 g (0.34 mmole) S-methyl-(6-phenylsulfanyl-1,2,3,4-tetrahydro-naphthalen-1-ylmethyl)-carbamic acid tert-butyl ester in 5 mL methylene chloride was added 0.175 g (1.02 mmole) meta-chloroperbenzoic acid. The reaction mixture was stirred at 23° C. for 30 minutes. The solution was concentrated under reduced pressure and the residue was dissolved in 25 mL ethyl ether. The solution was washed twice with 5 mL 5% sodium hydroxide and 15 mL water. The organic phase was dried (magnesium sulfate) and concentrated under reduced pressure to give S-(6-benzenesulfonyl-1,2,3,4-tetrahydro-naphthalen-1-ylmethyl)-methylcarbamic acid tert-butyl esteras a white foam, 0.1 g (71%), M+H=416. Chiral HPLC (Chiralpak AS, 25% isopropyl alcohol in hexane) retention time=16.9 minutes, 90 ee.

Step 6

S-(6-Benzenesulfonyl-1,2,3,4-tetrahydro-naphthalen-1-ylmethyl)-methylamine trifluoroacetate salt

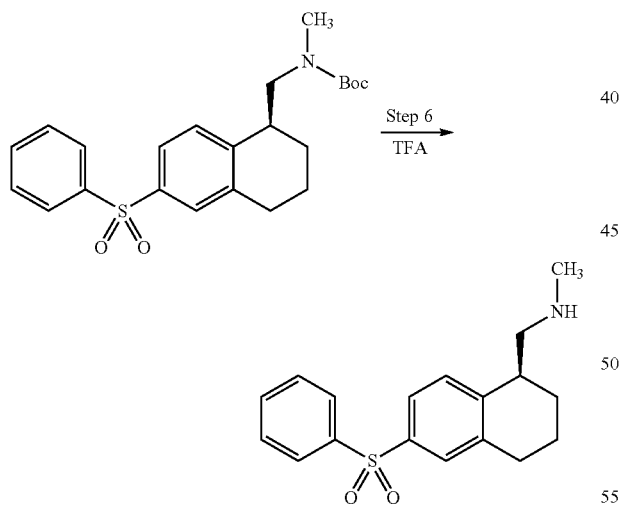

To a solution of 0.1 g (0.24 mmole) 90 ee S-(6-benzenesulfonyl-1,2,3,4-tetrahydro-naphthalen-1-ylmethyl)-methylcarbamic acid tert-butyl ester in 1.0 mL methylene chloride was added 1.0 mL trifluoroacetic acid. The mixture was stirred at 23° C. for 15 minutes. The solution was concentrated under reduced pressure and the residue was recrystallized from ethyl acetate/ethyl ether to provide S-(6-benzenesulfonyl-1,2,3,4-tetrahydro-naphthalen-1-ylmethyl)-methylamine as a trifluoroacetate salt, 0.093 g (90%), m.p. 146-147° C., M+H=316, $[\alpha]_D$=+0.4° (c=1.0, methanol).

Example 14

R-(6-Benzenesulfonyl-1,2,3,4-tetrahydro-naphthalen-1-ylmethyl)-methylamine

The synthetic procedure described in this Example was carried out according to the process shown in Scheme S.

SCHEME S

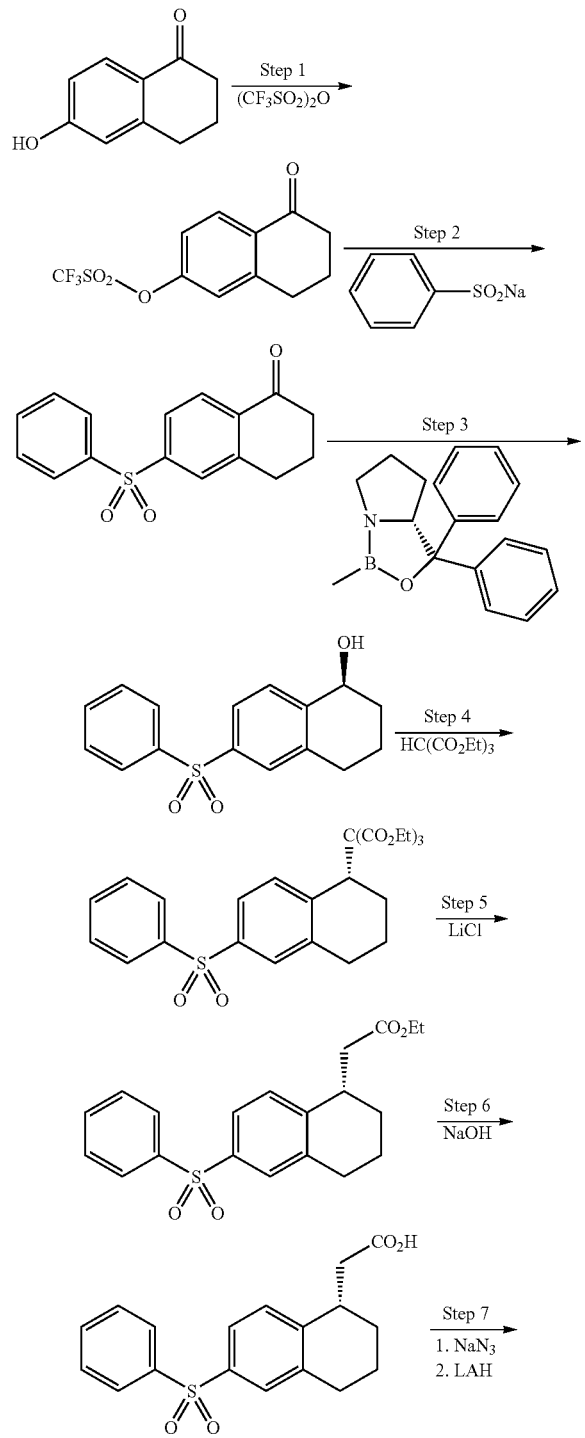

-continued

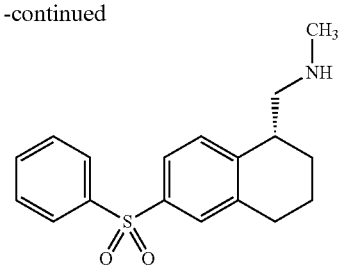

Step 1

Trifluoro-methanesulfonic acid
5-oxo-5,6,7,8-tetrahydro-naphthalen-2-yl ester

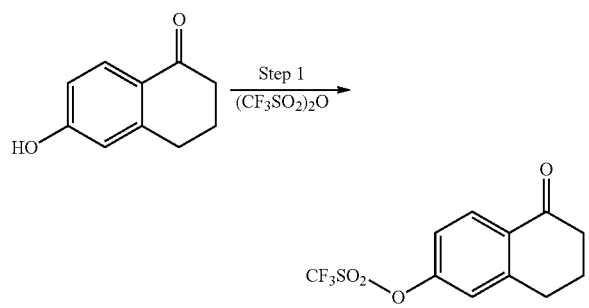

6-Hydroxytetralone (12 g, 0.072 mole) and triethylamine (10 mL, 0.072 mole) were dissolved in 200 ml methylene chloride and cooled in an ice bath. Trifluormethanesulfonic anhydride (20 g, 0.072 mole) was added dropwise, and the reaction mixture was stirred for 30 minutes. The reaction mixture was poured into 200 mL water, and the organic layer was separated and dried over magnesium sulfate. Evaporation of solvent under reduced pressure gave 15.5 g of trifluoro-methanesulfonic acid 5-oxo-5,6,7,8-tetrahydro-naphthalen-2-yl ester as an oil. MS: 295 (M+H)$^+$ Step 2

6-Benzenesulfonyl-3,4-dihydro-2H-naphthalen-1-one

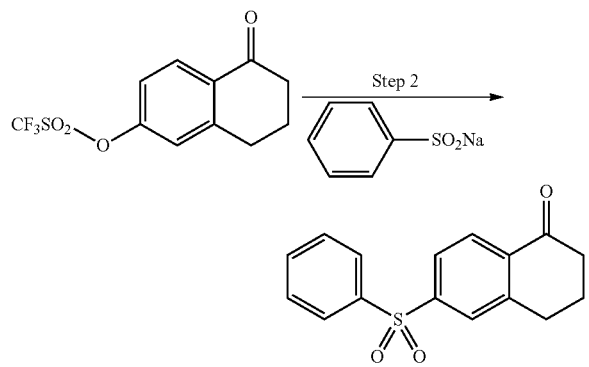

Trifluoro-methanesulfonic acid 5-oxo-5,6,7,8-tetrahydro-naphthalen-2-yl ester (13.0 g, 0.044 mole), sodium benzenesulfinate (7.25 g, 0.044 mole), 4,5-bis(diphenylphosphino, -9,9-dimethyl Xanthos (1.1 g, 0.004 mole), tris(dibenzylideneacetone) dipalladium(0) (1.0 g, 0.004 mole), cesium carbonate (5.0 g) and tetrabutylammonium fluoride (5 mL of 1M in THF) were all added to 100 mL toluene, and the reaction mixture was refluxed for four hours. The reaction mixture was cooled to room temperature and partitioned between ethyl acetate and water. The organic layer was dried over magnesium sulfate, and solvent was removed under reduced pressure. The resulting residue was purified by medium pressure chromatography eluting with methylene chloride to yield 5.5 g of 6-benzenesulfonyl-3,4-dihydro-2H-naphthalen-1-one. Mp: 121° C. MS: 287 (M+H)$^+$.

Step 3

S-6-Benzenesulfaoyl-1,2,3,4-tetrahydro-naphthalen-1-ol

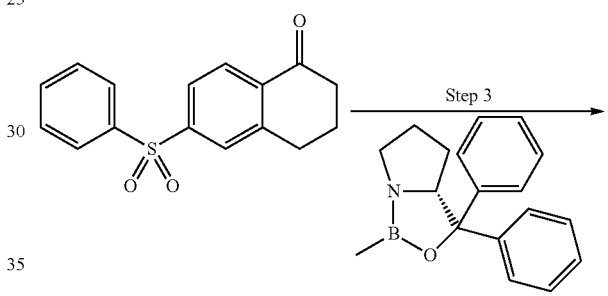

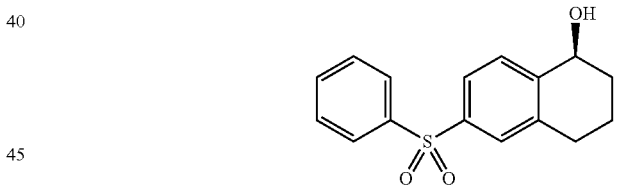

This step follows the general procedure of Salunkhe and Burkhardt, Tetrahedron Letters 38(9): 1523 (1997). A solution of R-2-methyl CBS oxaborilidine (2.2 mL, (0.002 mole, 1M in toluene) and diethylanaline-borane complex (4.6 mL, 0.026 mole) in 200 mL toluene was heated to 35° C. 6-Benzenesulfonyl-3,4-dihydro-2H-naphthalen-1-one (6.5 g, 0.022 mole) in 100 mL toluene was added dropwise over two hours. The reaction was quenched with 20 mL of 10% HCl followed by 30 mL methanol, and the reaction mixture was stirred for 30 minutes. The reaction mixture was diluted with 200 mL water, extracted with ethyl acetate, and dried over magnesium sulfate. Solvent was evaporated under reduced pressure, and the residue was recrystallized from toluene/MTBE to yield 6 g of S-6-phenylsulfanyl-1,2,3,4-tetrahydro-naphthalen-1-ol. Mp: 136° C. MS: 288 (M+H)$^+$. 99%+ee anlysis by chiral HPLC Chiralpak AD, eluting with 5% IPA in hexane, retention time=29.7 minutes.

Step 4

R-2-(6-Benzenesulfonyl-1,2,3,4-tetrahydro-naphthalen-1-yl)-2-ethoxycarbonyl-malonic acid diethyl ester

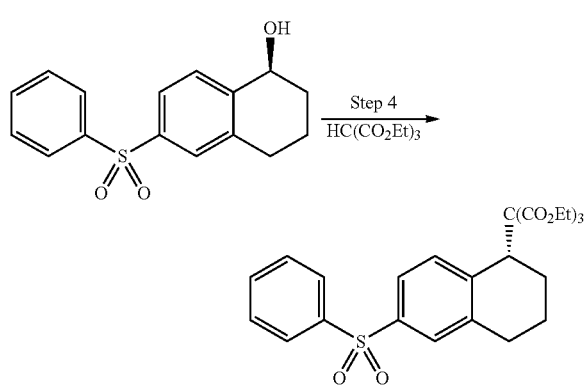

S-6-Phenylsulfanyl-1,2,3,4-tetrahydro-naphthalen-1-ol (2.0 g, 6.9 mmole), trimethylphosphine (13.9 mL, 13.9 mmol, 1M in THF), and triethylmethylenetricarboxylate (2.9 mL, 13.9 mmol) were dissolved together in 75 mL toluene, and the temperature of the reaction mixture was lowered to −50° C. A solution of di-t-butylazidodicarboxylate (3.2 g, 13.9 mmol) in 15 mL THF was added dropwise over 25 minutes, and the reaction mixture was stirred at −50° C. for an additional 30 minutes. The reaction mixture was allowed to warm to 25° C., and stirring was continued for three hours. The reaction mixture was partitioned between water and ethyl acetate, and the organic phase was dried over magnesium sulfate. Solvent was removed under reduced pressure, and the residue was purified by medium pressure chromatography, eluting with 25% ethylacetate in hexane to give 1.3 g of R-2-ethoxycarbonyl-2-(6-phenylsulfanyl-1,2,3,4-tetrahydro-naphthalen-1-yl)-malonic acid diethyl ester. MS: 504 (M+H)$^+$.

Step 5

S-(6-Benzenesulfonyl-1,2,3,4-tetrahydro-naphthalen-1-yl)-acetic acid ethyl ester

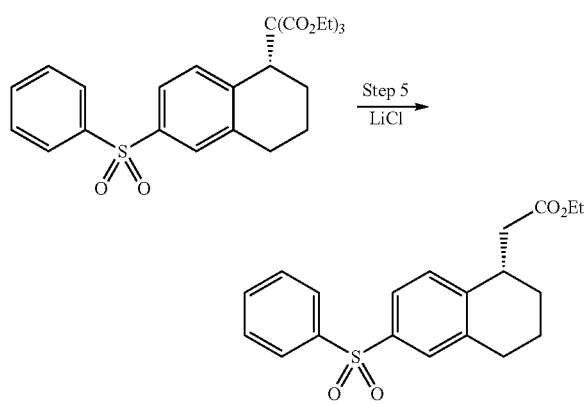

R-2-ethoxycarbonyl-2-(6-phenylsulfanyl-1,2,3,4-tetrahydro-naphthalen-1-yl)-malonic acid diethyl ester 1.3 g, 2.6 mmol), lithium chloride (0.33 g, 7.8 mmol) and 0.2 mL water were added to 20 mL of dimethyl sulfoxide. The reaction mixture was refluxed for two hours and then cooled to room temperature. The reaction mixture was diluted with 40 mL of water, and extracted with ethyl acetate. The organic layer was dried over magnesium sulfate, and solvent was removed under reduced pressure to yield 0.8 g of S-(6-benzenesulfonyl-1,2,3,4-tetrahydro-naphthalen-1-yl)-acetic acid ethyl ester as an oil. MS: 359 (M+H)$^+$. 96% ee by chiral HPLC, chiralpak AD eluting with 20% IPA in hexane, retention time 12.2 minutes.

Step 6

(6-Benzenesulfonyl-1,2,3,4-tetrahydro-naphthalen-1-yl)-acetic acid

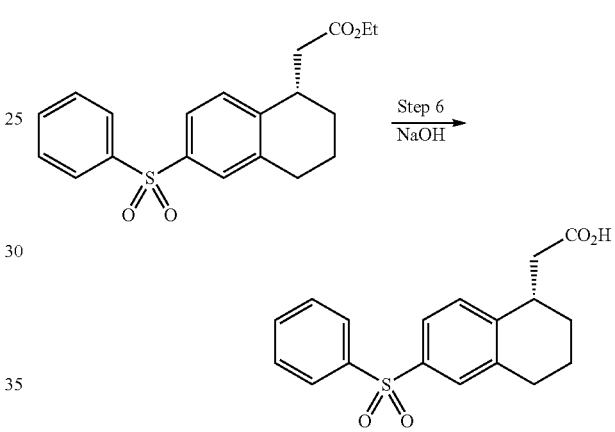

S-(6-Benzenesulfonyl-1,2,3,4-tetrahydro-naphthalen-1-yl)-acetic acid ethyl ester (0.8 g, 2.23 mmol) and 10 mL of 10% NaOH were added tp 20 mL ethanol, and the reaction mixture was refluxed for 30 minutes. The reaction mixture was diluted with 100 mL of water and acidified with 10% HCl. The aqueous mixture was extracted with ethyl acetate, and the organic layer was dried over magnesium sulfate. Solvent was removed under reduced pressure, and the residue was recrystallized from MTBE to give 0.4 g of (6-benzenesulfonyl-1,2,3,4-tetrahydro-naphthalen-1-yl)-acetic acid. MS: 331 (M+H)$^+$. Mp: 144° C.

Step 7

R-(6-Benzenesulfonyl-1,2,3,4-tetrahydro-naphthalen-1-ylmethyl)-methylamine

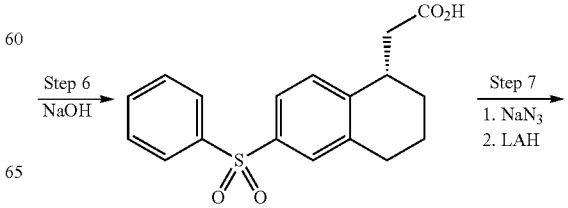

-continued

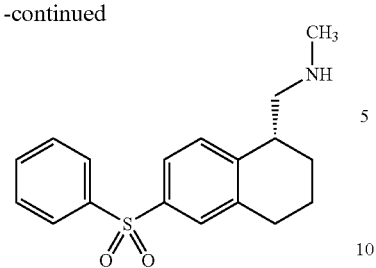

(6-Benzenesulfonyl-1,2,3,4-tetrahydro-naphthalen-1-yl)-acetic acid (0.3 g, 1.0 mmol) and triethylamine (0.15 mL, 1.1 mmol) were dissolved in 15 mL acetone, and the reaction mixture was cooled in an ice-bath. n-Butyl chloroformate (0.15 mL, 1.1 mmol) was added dropwise over five minutes to the stirring reaction mixture. After stirring an additional 220 minutes, sodium azide (0.13 g, 2.1 mmol) in 5 mL water was added dropwise. The reaction mixture was stirred another 20 minutes at ice bath temperature. The reaction was quenched by addition of 50 mL water and the resulting aqueous mixture was extracted with 70 mL toluene. The toluene solution was dried over magnesium sulfate and filtered. The toluene solution was then heated to reflux for 30 minutes, cooled to room temperature, and solvent was removed under reduced pressure. The resulting residue was dissolved in a mixture of 10 mL THF and 30 mL diethyl ether, and cooled in an ice-bath. Lithium aluminum hydride (3 mL of 1M in ether) was added dropwise, and the suspension stirred at ice bath temperature for three hours. The reaction was quenched with 3 mL 10% NaOH, and sodium sulfate drying agent was added. The organic solution was recovered by filtration and solvent was removed under reduced pressure to yield and the mixture filtered after 30 min. The organic solution is evaporated to give R-(6-benzenesulfonyl-1,2,3,4-tetrahydro-naphthalen-1-ylmethyl)-methylamine as an oil. MS: 316 (M+H)⁺.

Example 15

R-[6-(3-Methoxy-benzenesulfonyl)-1,2,3,4-tetrahydro-naphthalen-1ylmethyl]methyl-amine The synthetic procedure described in this Example was carried out according to the process shown in Scheme T.

SCHEME T

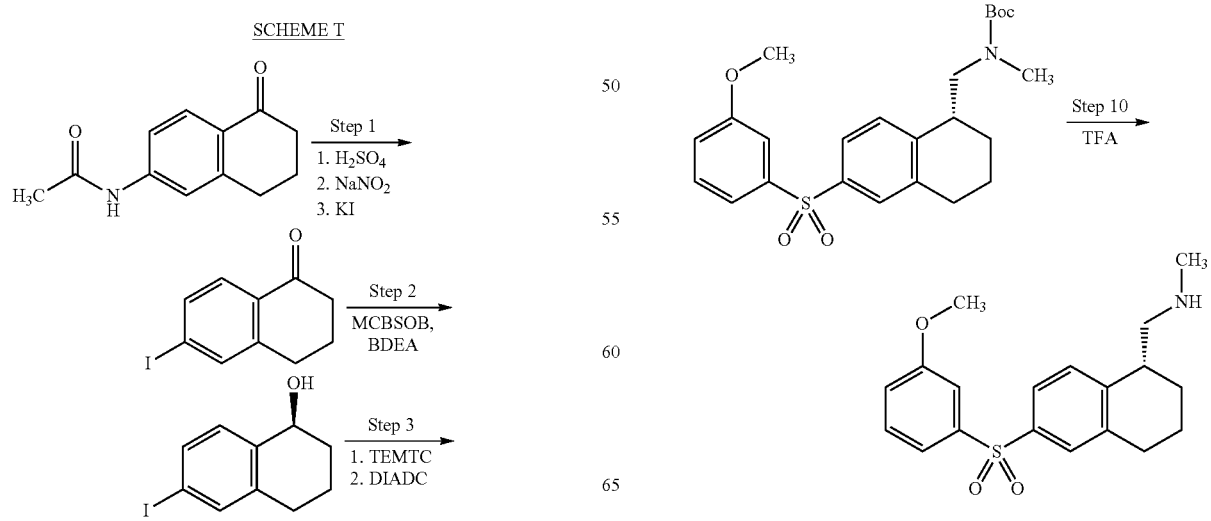

-continued

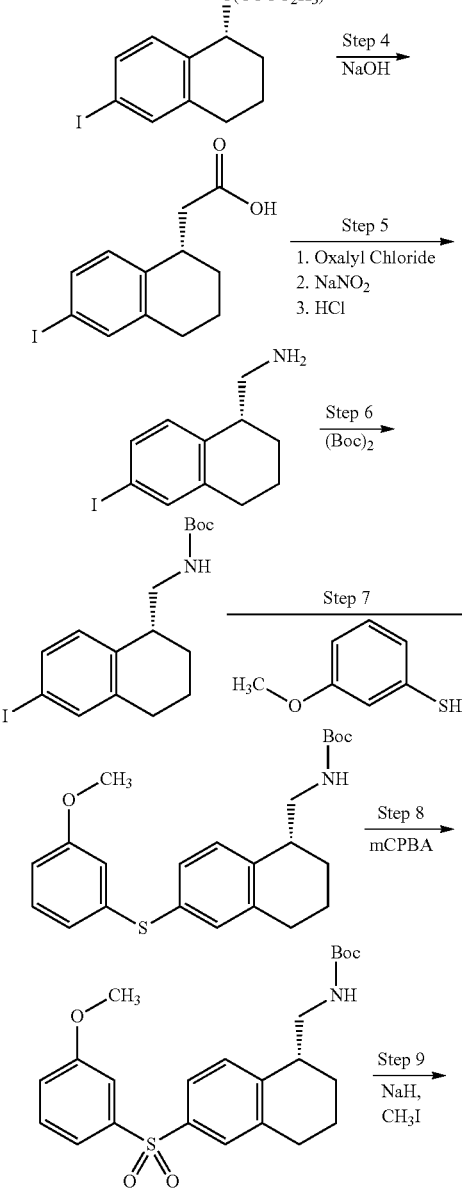

Step 1

6-Iodo-3,4-dihydro-2H-naphthalen-1-one

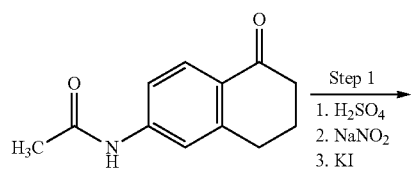

A mixture of N-(5-oxo-5,6,7,8-tetrahydronaphthalen-2-yl)-acetamide 2.5 grams (12.3 mmole) in 20 mL 20% sulfuric acid was heated at 90° for 45 minutes. The solution was allowed to cool to room temperature whereupon 6-amino-3,4-dihydro-2H-naphthalen-1-one sulfate (not shown) precipitated as a solid mass. To this solid was added 20 mL water and 20 mL glacial acetic acid. The resulting solution was stirred in an ice bath and a solution of 1.72 grams (25 mmoles) sodium nitrite in 15 mL water was added dropwise over 0.5 hour. The reaction mixture was slowly poured into a well stirred solution of 8 grams (48 mmoles) potassium iodide in 80 mL water. The mixture was extracted with 200 mL ethyl ether, and the organic phase was washed with water, then saturated sodium hydrogen sulfite, then with saturated sodium chloride. The organic phase was dried (magnesium sulfate) and concentrated under reduced pressure. The residue was subjected to low pressure column chromatography over silica gel 230-400 mesh eluting with 5% ethyl acetate in hexane. 6-Iodo-3,4-dihydro-2H-naphthalen-1-one was obtained as a white solid, 3.12 grams (94%), m.p. 77-78°.

Step 2

S-6-Iodo-1,2,3,4-tetrahydro-naphthalen-1-ol

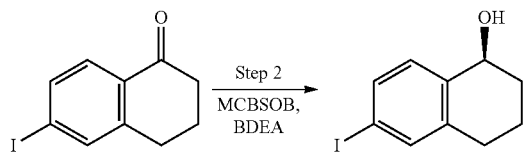 [SMILES: O=C1CCCc2cc(I)ccc21 ; O[C@H]1CCCc2cc(I)ccc21]

A solution of R-2-methyl-CBS-oxazaborolidine (MCBSOB, 3.7 mL (3.7 mmoles) 1.0 M in toluene) and borane-diethylaniline complex (BDEA, 7.5 mL, 42 mmoles) in 40 mL toluene was heated to 30°. A solution of 6-iodo-3,4-dihydro-2H-naphthalen-1-one (10 grams, 36.8 mmoles) in 40 mL toluene was added dropwise over 2.5 hours. The reaction mixture was stirred for an additional 0.5 hour at 30°. To the solution (at room temperature) was added 20 mL methanol. After 0.25 hour, 50 mL 1N hydrochloric acid was added slowly. The mixture was stirred for 20 minutes then it was extracted with 200 mL ethyl ether. The organic phase was washed with 1N hydrochloric acid, water, and saturated sodium chloride. The organic phase was dried (magnesium sulfate) and concentrated under reduced pressure. To the oily residue was added 100 mL hot hexane. When crystallization was complete, the white solid was collection and dried to give S-6-iodo-1,2,3,4-tetrahydro-naphthalen-1-ol, 9.62 grams (95%). m.p. 102-103°, M$^+$=274, $[\alpha]_D$=+12.2° (c=1, chloroform).

Step 3

R-2-Ethoxycarbonyl-2-(6-iodo-1,2,3,4-tetrahydro-naphthalen-1-yl)-malonic acid diethyl ester

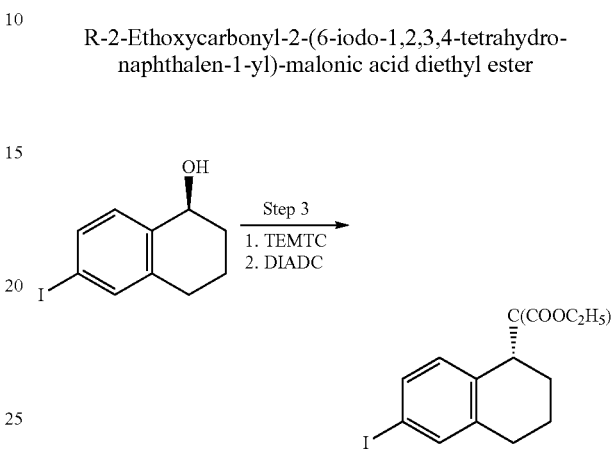

To a solution of S-6-iodo-1,2,3,4-tetrahydro-naphthalen-1-ol (9.5 grams, 34.7 mmoles) and triethylmethane tricarboxylate (TEMTC, 16 grams, 69.3 mmoles) in 150 mL toluene was added 70 mL 1.0M trimethylphosphine in toluene. The solution was stirred and cooled to −50° under nitrogen. Neat diisopropylazodicarboxylate (DIADC, 14 mL, 69.3 mmoles) was added dropwise over 0.5 hour. The solution was concentrated under reduced pressure. To the residue was added 100 mL water and 100 mL 3N sodium hydroxide. The mixture was extracted with diethyl ether, and the organic phase was washed with 3N sodium hydroxide, water, 1N hydrochloric acid, water again, then saturated sodium chloride. After drying (magnesium sulfate), the solution was concentrated under reduced pressure. To the residue was added 25 mL diethyl ether. After 10 minutes the crystalline deposit of diisopropyl-1,2-hydrazinedicarboxylate was removed by filtration. The filtrate was concentrated under reduced pressure and the residue was subjected to low pressure column chromatography over 230-400 mesh silica gel eluting with 7% ethyl acetate in hexane. R-2-Ethoxycarbonyl-2-(6-iodo-1,2,3,4-tetrahydro-naphthalen-1-yl)-malonic acid diethyl ester was obtained as a white crystalline solid (from hexane), 14.84 grams (88%), m.p. 86-87°, $[\alpha]_D$=−20.3°(c=1, chloroform), M$^+$=488.

Step 4

S-6-Iodo-1,2,3,4-tetrahydro-naphthalen-1-yl acetic acid

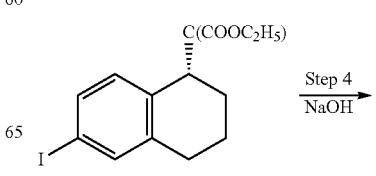

-continued

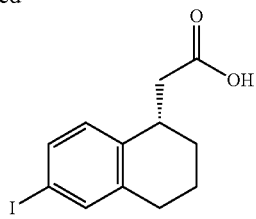

To a solution of R-2-ethoxycarbonyl-2-(6-iodo-1,2,3,4-tetrahydro-naphthalen-1-yl)-malonic acid diethyl ester (14 grams, 28.7 mmoles) in 25 mL methanol was added 60 mL water and 60 mL 3N sodium hydroxide. The reaction mixture was heated under reflux for 20 hours, then concentrated under reduced pressure. To the residue was added 200 mL glacial acetic acid. The solution was heated under reflux for 3 hours, and then it was concentrated under reduced pressure. The residue was partitioned between 60 mL water and 300 mL ethyl ether. The organic phase was dried (magnesium sulfate) and concentrated under reduced pressure. The residue was recrystallized from ethyl ether/hexane to give S-6-iodo-1,2,3,4-tetrahydro-naphthalen-1-yl acetic acid, 7.6 grams (84%), m.p. 90-91°, M$^+$=316, $[\alpha]_D$=+20 (c=1, chloroform).

Step 5

R—C-(6-Iodo-1,2,3,4-tetrahydro-naphthlen-1-yl)-methylamine hydrochloride

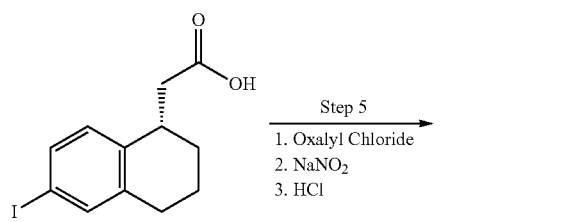

To a solution of S-6-iodo-1,2,3,4-tetrahydro-naphthalen-1-yl acetic acid (28.4 grams, 90 mmoles) in 350 mL dichloromethane was added 5 drops DMF and 12 mL (0.135 mole) oxalyl chloride. The reaction mixture was stirred at 23° for 1 hour and then it was concentrated under reduced pressure. The residue was dissolved in 250 mL acetone and the solution was cooled to 0°. A solution of sodium nitrite (12 grams, 0.18 mole) in 80 mL water was added dropwise over 0.5 hour. The reaction mixture was diluted with 400 mL water and 200 mL saturated sodium chloride. The mixture was extracted with 500 mL toluene, and the organic phase was dried (magnesium sulfate), then heated under reflux for 0.5 hour. The solution was concentrated under reduced pressure. The residue was dissolved in 150 mL dioxane and the solution was added dropwise to a boiling solution of 250 mL concentrated hydrochloric acid over 40 minutes. The solution was decanted from a small amount of tar and the warm decantate was concentrated under reduced pressure. The residue was recrystallized from ethanol/ethyl ether to provide R—C-(6-iodo-1,2,3,4-tetrahydro-naphthlen-1-yl)-methylamine hydrochloride as the hydrochloride salt, 23.3 grams (80%), m.p. 276-277°, M$^+$=287, $[\alpha]_D$=−2.8° (c=1, methanol).

Step 6

R-(6-Iodo-1,2,3,4-tetrahydro-naphthlen-1-ylmethyl)-carbamic acid tert-butyl ester

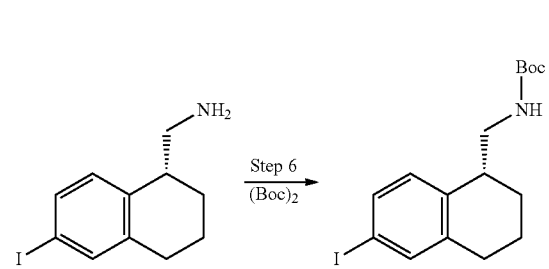

To a stirred mixture of R—C-(6-iodo-1,2,3,4-tetrahydro-naphthlen-1-yl)-methylamine hydrochloride (15 grams, 46.4 mmoles) and 8 mL triethylamine in 250 mL THF was added dropwise a solution of di-tert-butyl dicarbonate (10.9 grams, 49.9 mmoles) in 50 mL THF. The reaction mixture was stirred at 23° for 2 hours, then was concentrated under reduced pressure. The residue was partitioned between 300 mL ethyl ether and 150 mL water. The organic phase was dried (magnesium sulfate) and concentrated under reduced pressure. The residue was recrystallized from diethyl ether/hexane to provide R-(6-iodo-1,2,3,4-tetrahydro-naphthlen-1-ylmethyl)-carbamic acid tert-butyl ester, 12.91 grams (72%), m.p. 121-122°, M$^+$=387, $[\alpha]_D$=+24° (c=1, chloroform).

Step 7

R-[6-(3-Methoxy-phensulfanyl)-1,2,3,4-tetrahydro-naphthalen-1-ylmethyl]-carbamic acid tert-butyl ester

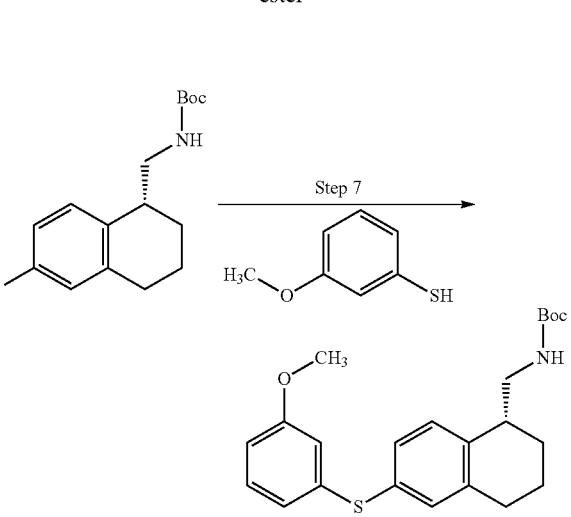

This step follows the general procedure of Itoh and Mase, Organic Letters 6(24): 4587 (2004). In 15 mL dioxane was mixed R-(6-iodo-1,2,3,4-tetrahydro-naphthlen-1-ylmethyl)-carbamic acid tert-butyl ester (0.5 gram, 1.29 mmoles), tris(dibenzylideneacetone)dipalladium(0) (0.059 gram, 0.064 mmoles), 4,5-bis(diphenylphosphino)-9,9-dimethylxanthene (0.074 gram, 0.128 mmoles), diisopropylethyl amine (0.333 gram, 2.58 mmoles) and 3-methoxy-thiophenol (0.2 gram, 1.42 mmoles). The reaction mixture was stirred at 50° for 1 hour, then was diluted with 50 mL diethyl ether and filtered. The filtrate was washed with 10 mL water, dried (magnesium sulfate) and concentrated under reduced pressure. The residue was subjected to low pressure column chromatography over silica gel 230-400 mesh eluting with 10% ethyl acetate in hexane. The eluted product was recrystallized from hexane to provide R-[6-(3-Methoxy-phensulfanyl)-1,2,3,4-tetrahydro-naphthalen-1-ylmethyl]-carbamic acid tert-butyl ester, 0.46 gram (89%), m.p. 73-74° C., M$^+$=399, $[\alpha]_D$=+26.6° (c=1, chloroform).

Step 8

R-[6-(3-Methoxy-benzenesulfonyl)-1,2,3,4-tetrahydro-naphthalen-1-ylmethyl]-carbamic acid tert-butyl ester

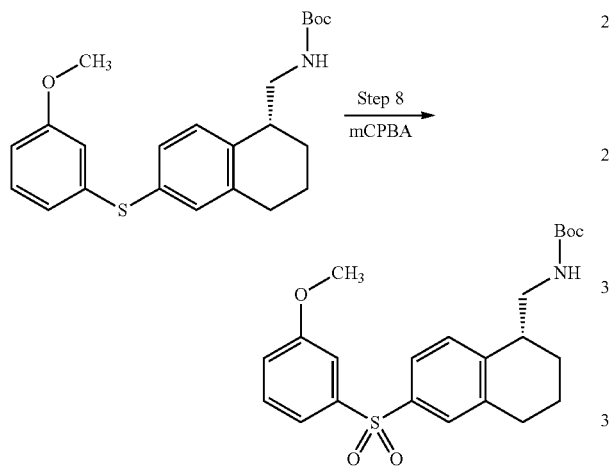

To a solution of R-[6-(3-methoxy-phensulfanyl)-1,2,3,4-tetrahydro-naphthalen-1-ylmethyl]-carbamic acid tert-butyl ester (0.2 gram, 0.5 mmole) in 10 mL dichloromethane was added m-chloroperbenzoic acid (0.3 gram, 1.34 mmole of 77% solids). The reaction mixture was stirred at 23° for 0.5 hour. The solution was concentrated under reduced pressure and the residue was partitioned between 50 mL ethyl acetate and 30 mL 5% sodium hydroxide. The organic phase was washed with saturated sodium chloride, dried (magnesium sulfate) and concentrated under reduced pressure to give R-[6-(3-methoxy-benzenesulfonyl)-1,2,3,4-tetrahydro-naphthalen-1-ylmethyl]-carbamic acid tert-butyl ester, 0.21 gram (97%), M$^+$Na=454.

Step 9

R-[6-(3-Methoxy-benzenesulfonyl)-1,2,3,4-tetrahydro-naphthalen-1-ylmethyl]-methyl-carbamic acid tert-butyl ester

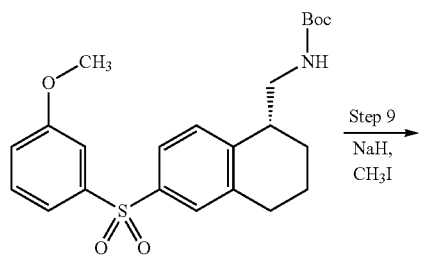

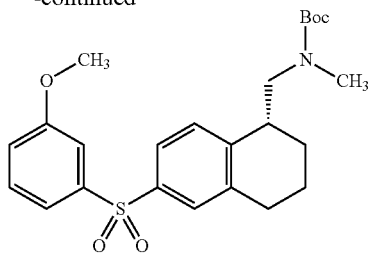

To a solution of R-[6-(3-methoxy-benzenesulfonyl)-1,2,3,4-tetrahydro-naphthalen-1-ylmethyl]-carbamic acid tert-butyl ester (0.2 gram, 0.46 mmole) in 3 mL DMF was added 0.025 gram (1 mmole) of 100% sodium hydride. To this mixture was added iodomethane (0.1 mL, 1.6 mmole). The reaction mixture was stirred at 23° for 2 hours, then was diluted with 25 mL water and extracted with 40 mL ethyl acetate. The organic phase was washed with water and saturated sodium chloride, dried (magnesium sulfate) and concentrated under reduced pressure. The residue was subjected to low pressure column chromatography over silica gel 230-400 mesh eluting with 20% ethyl acetate in hexane. R-[6-(3-Methoxy-benzenesulfonyl)-1,2,3,4-tetrahydro-naphthalen-1-ylmethyl]-methyl-carbamic acid tert-butyl ester was obtained as a foam, 0.15 gram (73%), M$^+$=445, $[\alpha]_D$=+16.4° (c=1, methanol).

Step 10

R-[6-(3-Methoxy-benzenesulfonyl)-1,2,3,4-tetrahydro-naphthalen-1ylmethyl]-methyl-amine

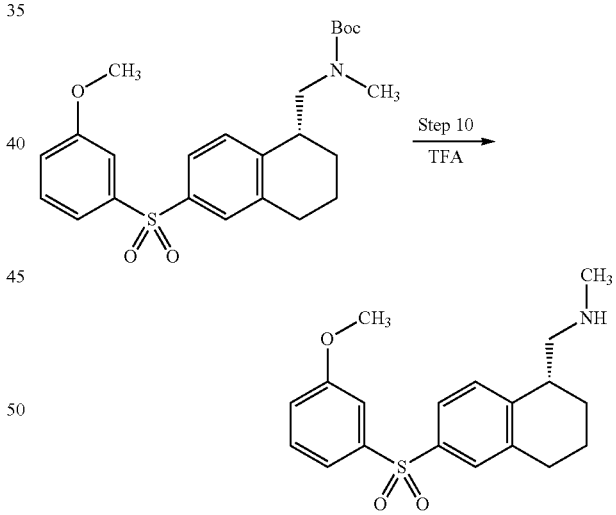

A warm solution of R-[6-(3-methoxy-benzenesulfonyl)-1,2,3,4-tetrahydro-naphthalen-1-ylmethyl]-methyl-carbamic acid tert-butyl ester (0.12 gram, 0.27 mmole) in 2 mL TFA was concentrated under reduced pressure. To the residue was added 0.5 mL methanol and 1.0 mL 1N hydrochloric acid in ethyl ether. The mixture was heated to boiling for 30 seconds and then it was concentrated under reduced pressure. R-[6-(3-Methoxy-benzenesulfonyl)-1,2,3,4-tetrahydro-naphthalen-1ylmethyl]-methyl-amine hydrochloride was obtained by recrystallization from methanol/ethyl acetate/ethyl ether, 0.08 gram (78%), m.p. 194-195°, M$^+$H=346, $[\alpha]_D$=−3.4° (c=1, methanol).

Similarly prepared using the procedure of Example 15 were:

R—C-[6-(-3-Methoxy-benzenesulfonyl)-1,2,3,4-tetrahydro-naphthalen-1-yl]-methylamine hydrochloride: m.p. 188-189° C., M⁺H=332, [α]$_D$=−6.0° (c=1, methanol);

R—C-[6-(3-Methanesulfonyl-benzenesulfonyl)-1,2,3,4-tetrahydro-naphthalen-1-yl]-methylamine hydrochloride; m.p. 265-266° C., M⁺H=380;

R—C-[6-(1H-Pyrazole-4-sulfonyl)-1,2,3,4-tetrahydro-naphthalen-1-yl]-methylamine; m.p. 181-182° C., M⁺H=292;

R—C-[6-(1-Methyl-1H-imidazole-2-sulfonyl)-1,2,3,4-tetrahydro-naphthalen-1-yl]-methylamine oxalate: m.p. 196-197° C., M⁺H=306;

R—C-[6-(3H-Indole-3-sulfonyl)-1,2,3,4-tetrahydro-naphthalen-1-yl]-methylamine, M⁺H=341;

R—C-[6-(5-Fluoro-3H-indole-3-sulfonyl)-1,2,3,4-tetrahydro-naphthalen-1-yl]-methylamine, M⁺H=359;

R—C-[6-(1H-Pyrrole-3-sulfonyl)-1,2,3,4-tetrahydro-naphthalen-1-yl]-methylamine, M⁺H=291.

R-Methyl-[6-(1H-pyrrole-3-sulfonyl)-1,2,3,4-tetrahydro-naphthalen-1-ylmethyl]-amine hydrochloride, M⁺H=305;

R—C-[6-(6-Fluoro-3H-benzimidazole-4-sulfonyl)-1,2,3,4-tetrahydro-naphthalen-1-yl]-methylamine oxalate, M⁺H=360;

R—C-(6-Benzenesulfonyl-8-fluoro-1,2,3,4-tetrahydro-naphthalen-1-yl)-methylamine hydrochloride, m.p. 248-249° C., M⁺H=320, [α]$_D$=+25.2° (c=1, methanol);

R-(6-Benzenesulfonyl-8-fluoro-1,2,3,4-tetrahydro-naphthalen-1-ylmethyl)-methyl-amine hydrochloride, M⁺H=334, [α]$_D$=+18.5° (c=1, methanol);

R—C-(6-Benzenesulfonyl-5-fluoro-1,2,3,4-tetrahydro-naphthalen-1-yl)-methylamine hydrochloride, M⁺H=320, [α]$_D$=+11.2° (c=0.5, methanol);

[6-(3-Fluoro-benzenesulfonyl)-1,2,3,4-tetrahydro-naphthalen-1-ylmethyl]-methyl-amine oxalate, M⁺H=334; and Ethyl-[6-(3-fluoro-benzenesulfonyl)-1,2,3,4-tetrahydro-naphthalen-1-ylmethyl]-amine oxalate, M⁺H=348.

Example 16

R-3-(5-Aminomethyl-5,6,7,8-tetrahydro-naphthalene-2-sulfonyl)-benzonitrile

The synthetic procedure described in this Example was carried out according to the process shown in Scheme U.

SCHEME U

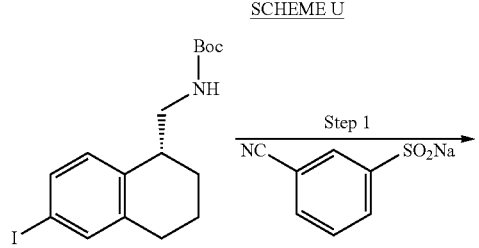

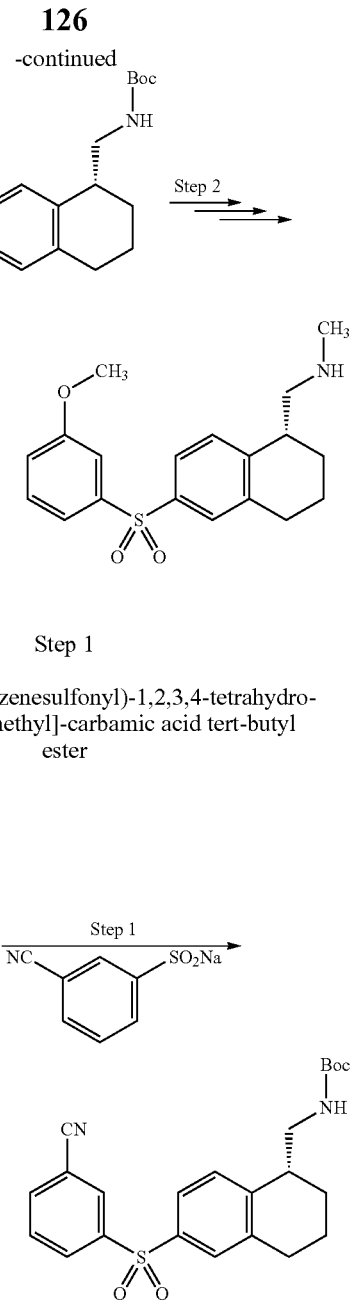

Step 1

R-[6-(3-Cyano-benzenesulfonyl)-1,2,3,4-tetrahydro-naphthalen-1-ylmethyl]-carbamic acid tert-butyl ester The sodium 3-cyanobenzenesulfinate used in this step was prepared by heating a solution of sodium sulfite (3.2 grams, 25.2 mmoles) in 10 mL water to 80°, and adding dropwise thereto a solution of 3-cyanobenzenesulfonyl chloride (2.55 grams, 12.6 mmoles) in 7 mL THF and a solution of sodium bicarbonate (2.1 grams, 25.2 mmoles). The mixture was extracted with diethyl ether and the aqueous phase was concentrated under reduced pressure, heated, and filtered through Whatman GF/B glass fiber filter. The filtrate was concentrated under reduced pressure to give 1.92 grams (81%), of sodium 3-cyanobenzenesulfinate m.p. 216-218° C.

Following the general procedure of Cacchi et al., J. Organic Chemistry: 69(17): 5608-5614 (2004), a mixture of R-(6-iodo-1,2,3,4-tetrahydro-naphthlen-1-ylmethyl)-carbamic acid tert-butyl ester (0.4 gram, 1.0 mmole) sodium 3-cyanobenzenesulfinic acid (0.246 gram, 1.3 mmole), tris(dibenzylideneacetone)dipalladium(0) (0.05 gram, 0.054 mmole), 4,5-bis(diphenylphosphino)-9,9-dimethylxanthene (0.062 gram, 0.108 mmole), cesium carbonate (0.53 gram, 1.5 mmole), and tetra-n-butyl ammonium chloride (0.362 gram, 1.3 mmole) in 10 mL toluene was heated at 95° for 4 hours. The reaction mixture was diluted with 80 mL ethyl acetate and washed with saturated sodium chloride. The organic phase was dried (magnesium sulfate) and concentrated under reduced pressure. The residue was subjected to low pressure column chromatography over silica gel 230-400 mesh eluting with 25% ethyl acetate in hexane. R-[6-(3-Cyano-benzene-sulfonyl)-1,2,3,4-tetrahydro-naphthalen-1-ylmethyl]-carbamic acid tert-butyl ester was obtained as a foam, 0.2 gram (47%), M+=426, [α]$_D$=+5° (c=1, methanol).

Step 2

R-3-(5-Aminomethyl-5,6,7,8-tetrahydro-naphthalene-2-sulfonyl)-benzonitrile

Following the procedure of steps 9 and 10 of Example 15, R-3-(5-Aminomethyl-5,6,7,8-tetrahydro-naphthalene-2-sulfonyl)-benzonitrile was prepared as an oxalate salt: m.p. 212-213° C., M+H=327, [α]$_D$=+5.8° (c=1, DMSO);

Example 17

R—N-(6-Benzenesulfonyl-8-fluoro-1,2,3,4-tetrahydro-naphthalen-1-ylmethyl)-acetamide The synthetic procedure described in this Example was carried out according to the process shown in Scheme V.

SCHEME V

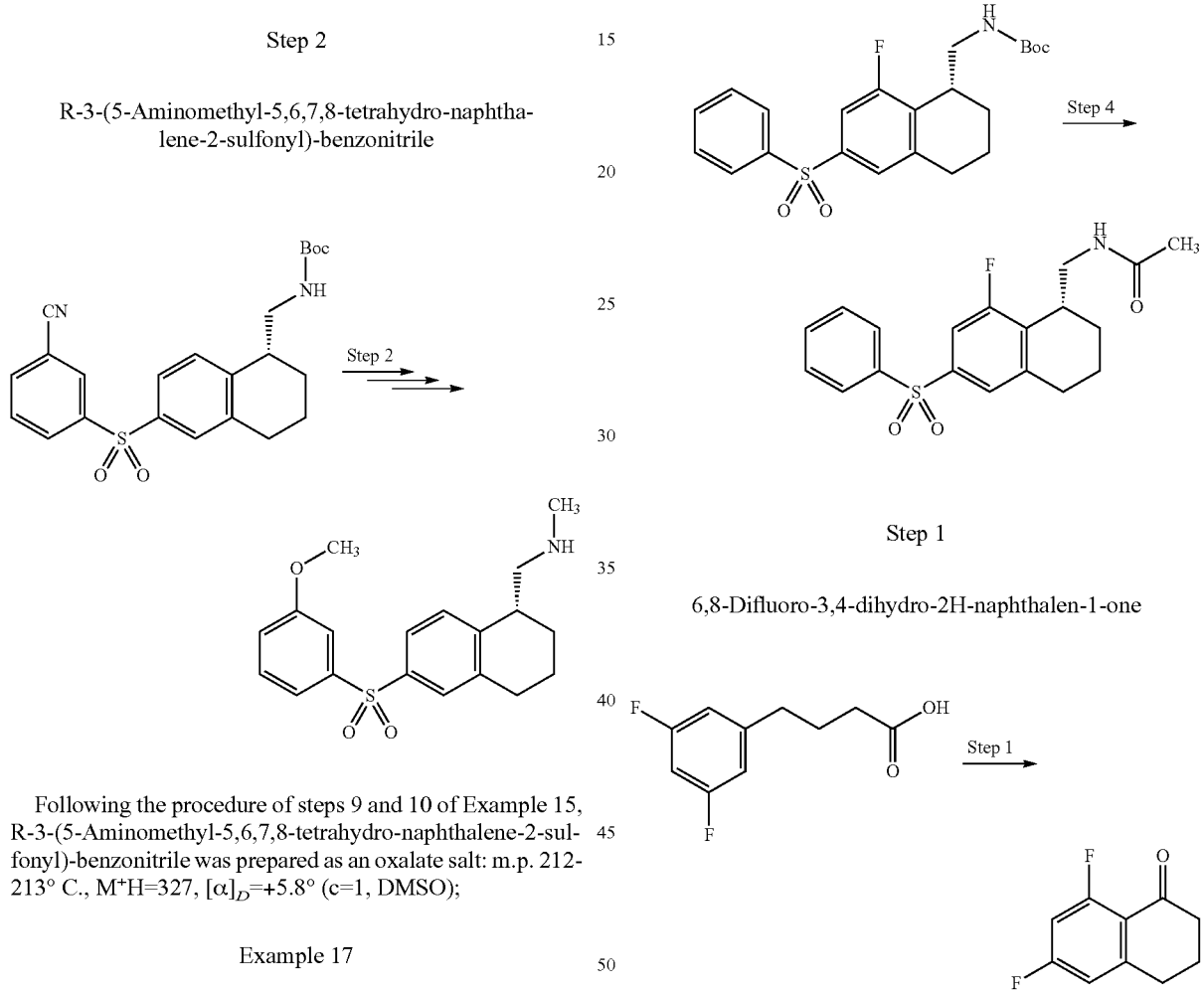

Step 1

6,8-Difluoro-3,4-dihydro-2H-naphthalen-1-one

This step follows the general procedure reported by Eaton et al., Organic Chemistry 38(23): 4071-4073 (1973). Eaton's reagent, prepared from 32 g phosphorus pentoxide and 192 mL methanesulfonic acid, was heated at 65° C. A solution of 4-(3,5-difluoro-phenyl)-butyric acid (12.85 grams, 64.19 mmoles, prepared as described by Repke et al., U.S. Pat. No. 5,538,988) in 30 mL methanesulfonic acid was added and the reaction mixture was heated at 65° C. for 35 minutes. The mixture was poured onto 1 L cracked ice and the product was extracted twice with 500 mL of a mixture of 2 parts diethyl ether to 1 part ethyl acetate. The organic phase was washed with saturated sodium bicarbonate, water, saturated sodium chloride and then it was dried (magnesium sulfate). The solution was concentrated under reduced pressure. 6,8-Difluoro- 3,4-dihydro-2H-naphthalen-1-one was isolated by recrystallization from hexane, 9.55 grams (82%), m.p. 57-58° C.

Step 2

8-Fluoro-6-phenylsulfanyl-3,4-dihydro-2H-naphthalen-1-one

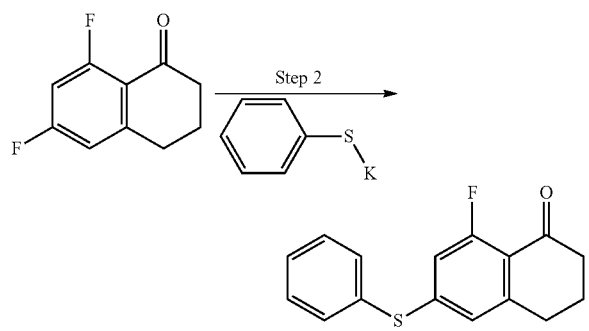

A mixture of 6,8-difluoro-3,4-dihydro-2H-naphthalen-1-one (1.0 gram, 5.5 moles) and potassium thiophenolate (0.81 gram, 5.5 mmole) in 4 mL DMSO was heated at 50° C. for 0.5 hour. The mixture was diluted with 30 mL 0.1N hydrochloric acid and then it was extracted with 50 mL diethyl ether. The organic phase was washed with water, dried (magnesium sulfate) and concentrated under reduced pressure. 8-Fluoro-6-phenylsulfanyl-3,4-dihydro-2H-naphthalen-1-one was obtained by recrystallization of the residue from ethyl acetate/hexane, 0.871 gram (58%), m.p. 112-113° C., M$^+$H=273.

Step 3

R-(6-benzenesulfonyl-8-fluoro-1,2,3,4-tetrahydro-naphthalen-1-ylmethyl)-carbamic acid tert-butyl ester

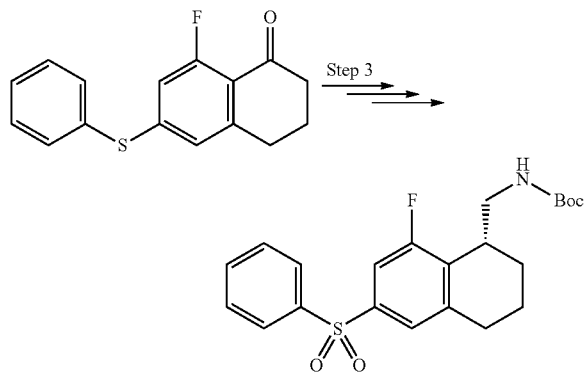

R-(6-benzenesulfonyl-8-fluoro-1,2,3,4-tetrahydro-naphthalen-1-ylmethyl)-carbamic acid tert-butyl ester was obtained by preparing (8-fluoro-6-phenylsulfanyl-1,2,3,4-tetrahydro-naphthalen-1-ylmethyl)-carbamic acid tert-butyl ester (not shown) by the procedure of steps 2 through 6 of Example 15 above, then oxidizing the sulfanyl compound to the sulfonyl product using the procedure of step 8 of Example 15. M$^+$H=420.

Step 4

R—N-(6-Benzenesulfonyl-8-fluoro-1,2,3,4-tetrahydro-naphthalen-1-ylmethyl)-acetamide

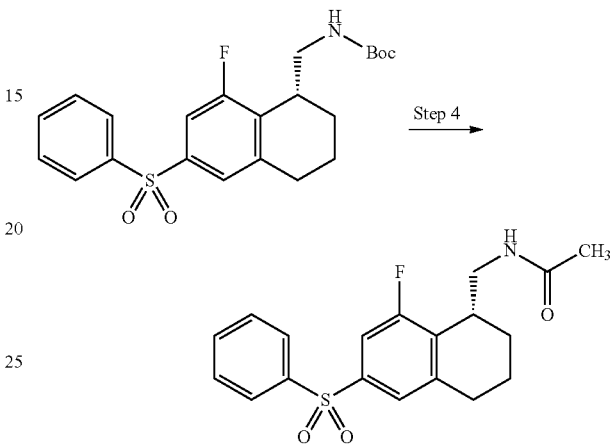

A warm solution of R-(6-benzenesulfonyl-8-fluoro-1,2,3,4-tetrahydro-naphthalen-1-ylmethyl)-carbamic acid tert-butyl ester (0.1 gram, 0.24 mmole) in 2 mL TFA was concentrated under reduced pressure. The residue was dissolved in 5 mL pyridine, and 0.5 mL acetic anhydride was added. The reaction mixture was stirred at 23° for 2 hours. The solution was concentrated under reduced pressure and the residue was partitioned between 25 mL chloroform and 5 mL water. The organic phase was dried (magnesium sulfate) and concentrated under reduced pressure to leave R—N-(6-benzenesulfonyl-8-fluoro-1,2,3,4-tetrahydro-naphthalen-1-ylmethyl)-acetamideas a homogenous foam, 0.06 gram (69%), M$^+$H=362.

Similarly prepared was R—N-[6-(1H-Indole-3-sulfonyl)-1,2,3,4-tetrahydro-naphthalen-1-ylmethyl]-acetamide, M$^+$+H=383.

Example 18

R-2-{[6-(3-Fluoro-benzenesulfonyl)-1,2,3,4-tetrahydro-naphthalen-1-ylmethyl]-amino}-3,5-dihydro-imidazol-4-one The synthetic procedure described in this Example was carried out according to the process shown in Scheme W.

SCHEME W

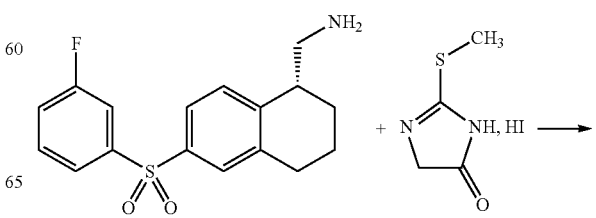

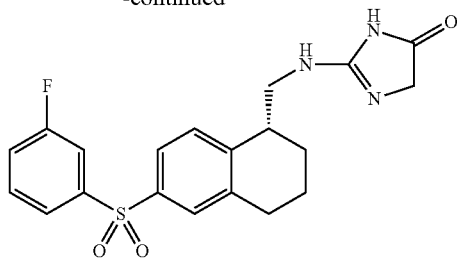

A mixture of R—C-[6-Fluoro-benzenesulfonyl]-1,2,3,4-tetrahydro-naphthalen-1-yl]-methylamine (0.28 grams, 0.877 mmole), 2-methylsulfanyl-3,5-dihydro-imidazol-4-one (0.25 grams, 0.96 mmole, prepared by the method reported by Chen et al., WO9736859) and sodium hydroxide (0.038 grams, 0.96 mmole) in 6 mL ethanol was heated under reflux for 22 hours. The solution was concentrated under reduced pressure to 1/3 volume, diluted with 25 mL ethyl acetate, and washed with 10 mL 5% sodium carbonate. The organic phase was dried (magnesium sulfate) and concentrated under reduced pressure. The residue was subjected to column chromatography over silica gel 230-400 mesh eluting with a gradient of 2-15% methanol in chloroform containing 0.25% ammonium hydroxide. R-2-{[6-(3-Fluoro-benzenesulfonyl)-1,2,3,4-tetrahydro-naphthalen-1-ylmethyl]-amino}-3,5-dihydro-imidazol-4-one was obtained as a white solid, 0.205 grams (58%), M$^+$H=402.

Example 19

C-[6-(6-Fluoro-1H-benzoimizol-4-ylsulfanyl)-1,2,3,4-tetrahydro-naphthalen-1-yl]-methylamine The synthetic procedure described in this Example was carried out according to the process shown in Scheme X.

SCHEME X

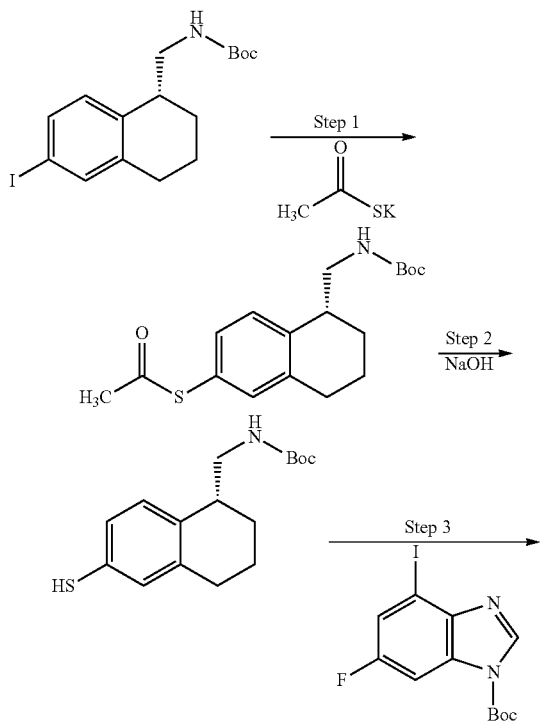

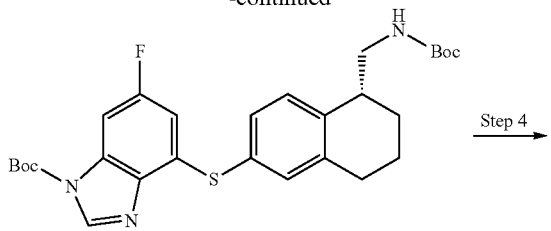

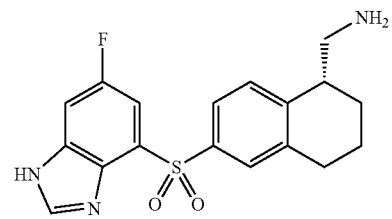

Step 1

R-Thioacetic acid S-[5-(tert-butoxycarbonylamino-methyl)-5,6,7,8-tetrahydro-naphthalen-2-yl]ester

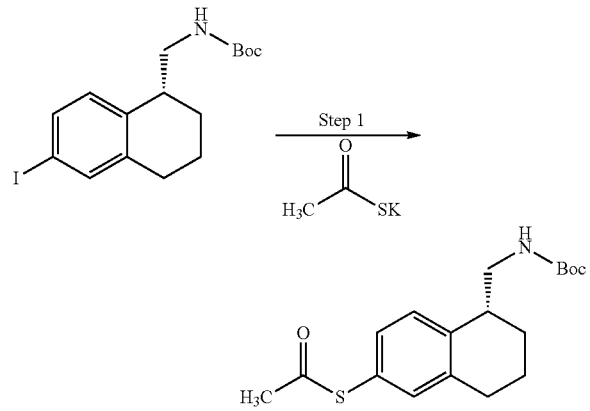

A mixture of R-(6-iodo-1,2,3,4-tetrahydro-naphthlen-1-ylmethyl)-carbamic acid tert-butyl ester (2.0 grams, 5.2 mmoles) potassium thioacetate (0.713 grams, 6.24 mmoles), 4,5-bis(diphenylphosphino)-9,9-dimethylxanthene (0.301 grams, 0.52 mmole), tris(dibenzylideneacetone)dipalladium (0) (0.275 grams, 0.3 mmoles), and diisopropylethyl amine (1.34 grams, 10.4 mmoles) in 50 mL dioxane was stirred at 23° for 18 hours. The mixture was diluted with 100 mL ethyl ether and filtered. The filtrate was washed with 0.1N hydrochloric acid, water, and saturated sodium chloride. The organic phase was dried (magnesium sulfate) and concentrated under reduced pressure. The residue was subjected to low pressure column chromatography over silica gel 230-400 mesh eluting with a gradient of 10-15% ethyl acetate in hexane. R-Thioacetic acid S-[5-(tert-butoxycarbonylamino-methyl)-5,6,7,8-tetrahydro-naphthalen-2-yl]ester was obtained as a white solid, 0.9 grams (52%), m.p. 68-69°, M$^+$H=336, $[\alpha]_D$=+32.5° (c=1, chloroform).

Step 2

R-(6-Mercapto-1,2,3,4-tetrahydro-naphthalen-1-ylmethyl)-carbamic acid tert-butyl ester

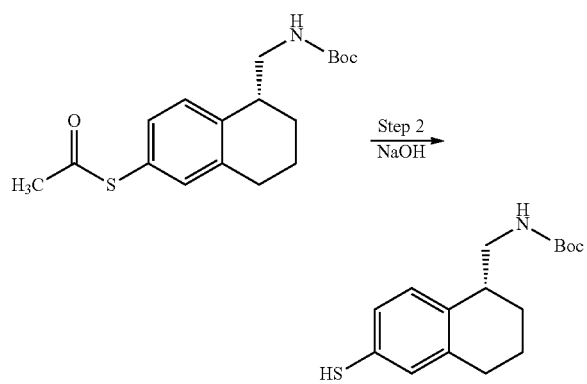

To a solution of R-thioacetic acid S-[5-(tert-butoxycarbonylamino-methyl)-5,6,7,8-tetrahydro-naphthalen-2-yl]ester (0.84 grams, 2.5 mmoles) in 10 mL methanol was added 1.0 mL (4 mmole) 4 M sodium hydroxide. The solution was immediately concentrated under reduced pressure and the residue was partitioned between 10 mL 1.0 M hydrochloric acid and 50 mL ethyl ether. The organic phase was washed with water, dried (magnesium sulfate) and concentrated under reduced pressure to provide R-(6-mercapto-1,2,3,4-tetrahydro-naphthalen-1-ylmethyl)-carbamic acid tert-butyl ester as a crystalline solid, 0.7 gram (95%), m.p. 98-99°, $M^+=293$, $[\alpha]_D=+27.6°$ (c=1, chloroform).

Step 3

(R) 4-[5-(tert-Butoxycarbonylamino-methyl)-5,6,7,8-tetrahydro-naphthalen-2-ylsulfanyl]-6-fluoro-benzoimidazole-1-carboxylic acid tert-butyl ester

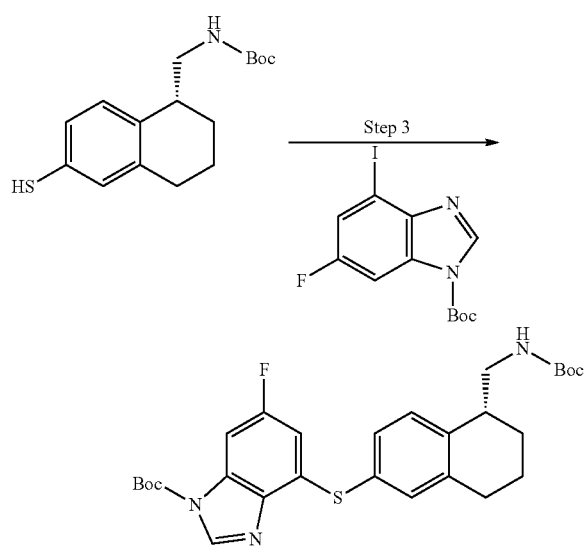

The 6-fluoro-4-iodo-benzoimidazole-1-carboxylic acid tert-butyl ester used in this step was prepared from 5-fluoro-3-iodo-benzene-1,2-diamine according to the procedure of Weber et al., WO 9400124. Briefly, a mixture of 5-fluoro-3-iodo-benzene-1,2-diamine (1.3 grams, 5.16 mmoles) and 1.5 mL of 96% formic acid was stirred at 100° for 3 hours, then cooled, and 35 mL 5% sodium hydroxide was added. The mixture was cooled in an ice bath and the resulting solid was collected, washed with water and dried in vacuo to provide 1.16 grams (86%) 6-fluoro-4-iodo-1H-benzoimidazole, m.p. 210-211° C. A mixture of 1.0 gram (3.8 mmoles) of this benzimidazole, di-tert-butyl dicarbonate (0.92 grams, 4.2 mmole), and 5 mg dimethylaminopyridine in 15 mL dioxane was stirred at 80° C. for 20 hours, then concentrated under reduced pressure. Purification of the residue by column chromatography over silica gel 230-400 mesh eluting with 30% ethyl acetate in hexane gave 6-fluoro-4-iodo-benzoimidazole-1-carboxylic acid tert-butyl ester as a crystalline solid, 1.38 grams (100%), m.p. 73-74° C.

A mixture of 6-fluoro-4-iodo-benzoimidazole-1-carboxylic acid tert-butyl ester (0.33 gram, 0.92 mmole), tris(dibenzylideneacetone)dipalladium(0) (0.047 gram, 0.05 mmole), 4,5-bis(diphenylphosphino)-9,9-dimethylxanthene (0.058 gram, 0.1 mmole), diisopropylethyl amine (0.32 mL (1.84 mmole), and R-(6-mercapto-1,2,3,4-tetrahydro-naphthalen-1-ylmethyl)-carbamic acid tert-butyl ester (0.3 gram, 1.02 mmole) in 6 mL dioxane was stirred at 50° C. for 1.5 hours. The mixture was diluted with 30 mL ethyl ether and washed with 2.5% hydrochloric acid, water, and 0.75M sodium carbonate. The organic phase was dried (magnesium sulfate) and concentrated under reduced pressure. The residue was subjected to column chromatography, first over silica gel 230-400 mesh eluting with a gradient of 5-40% ethyl acetate in hexane, and then over Activity I, neutral alumina eluting with 50% ethyl acetate in hexane. (R)-4-[5-(tert-Butoxycarbonylamino-methyl)-5,6,7,8-tetrahydro-naphthalen-2-ylsulfanyl]-6-fluoro-benzoimidazole-1-carboxylic acid tert-butyl ester was obtained as an oil, 0.32 gram (66%). NMR (CDCl$_3$) ppm δ: 8.39 (s, 1H), 7.46 (dd, 1H, J=6.3 Hz, J=8.7 Hz), 7.29 (m, 3H), 6.61 (dd, 1H, J=2.4 Hz, J=10 Hz), 4.67 (m, 1H), 3.44 (m, 1H), 3.32 (m, 1H), 3.0 (m, 1H), 2.76 (m, 2H), 1.81 (m, 4H), 1.70 (s, 9H), 1.60 (s, 9H).

Step 4

(R)—C-[6-(6-Fluoro-1H-benzoimidazol-4-ylsulfanyl)-1,2,3,4-tetrahydro-naphthalen-1-yl]-methylamine

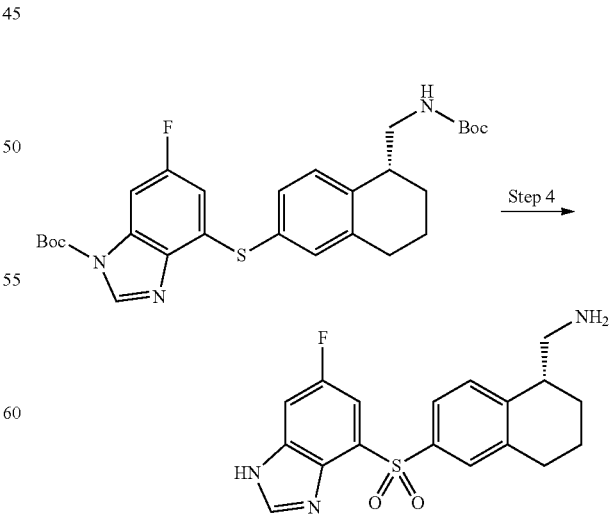

(R)-4-[5-(tert-Butoxycarbonylamino-methyl)-5,6,7,8-tetrahydro-naphthalen-2-ylsulfanyl]-6-fluoro-benzoimidazole- 1-carboxylic acid tert-butyl ester was treated with metachloroperbenzoic acid using the procedure of step 8 of Example 15. The resulting 4-[5-(tert-Butoxycarbonylamino-methyl)-5,6,7,8-tetrahydro-naphthalene-2-sulfonyl]-6-fluoro-benzoimidazole-1-carboxylic acid tert-butyl ester was deprotected following the procedure of step 10 of Example 15 to give C-[6-(6-Fluoro-1H-benzoimidazol-4-ylsulfanyl)-1,2,3,4-tetrahydro-naphthalen-1-yl]-methylamine, M+H=360.

Example 20

(R)—N-[6-(2-Fluoro-benzenesulfonyl)-1,2,3,4-tetrahydro-naphthalen-1-ylmethyl]-N'-cyano-guanidine (R)—N-[6-(2-Fluoro-benzenesulfonyl)-1,2,3,4-tetrahydro-naphthalen-1-ylmethyl]-N'-cyano-guanidine was prepared by treating C-[6-(2-Fluoro-benzenesulfonyl)-1,2,3,4-tetrahydro-naphthalen-1-yl]-methylamine with diphenylcyanoimidate according to the procedure reported in J. Med. Chem. 47, 12, 3201 (2004).

Example 21

(R)-1-[6-(3-Fluoro-benzenesulfonyl)-1,2,3,4-tetrahydro-naphthalen-1-ylmethyl]-3-methyl-urea (R)-1-[6-(3-Fluoro-benzenesulfonyl)-1,2,3,4-tetrahydro-naphthalen-1-ylmethyl]-3-methyl-urea was prepared by treatment of C-[6-(3-Fluoro-benzenesulfonyl)-1,2,3,4-tetrahydro-naphthalen-1-yl]methylamine with methyl isocyanate according to the procedure of Najer et al.; Bull. Soc. Chim. Fr.; 1069-1071 (1957).

Example 22

N-[2-(6-Benzenesulfonyl-1,2,3,4-tetrahydro-naphthalen-1-yl)-acetyl]-guanidine

The synthetic procedure described in this Example was carried out according to the process shown in Scheme Y.

SCHEME Y

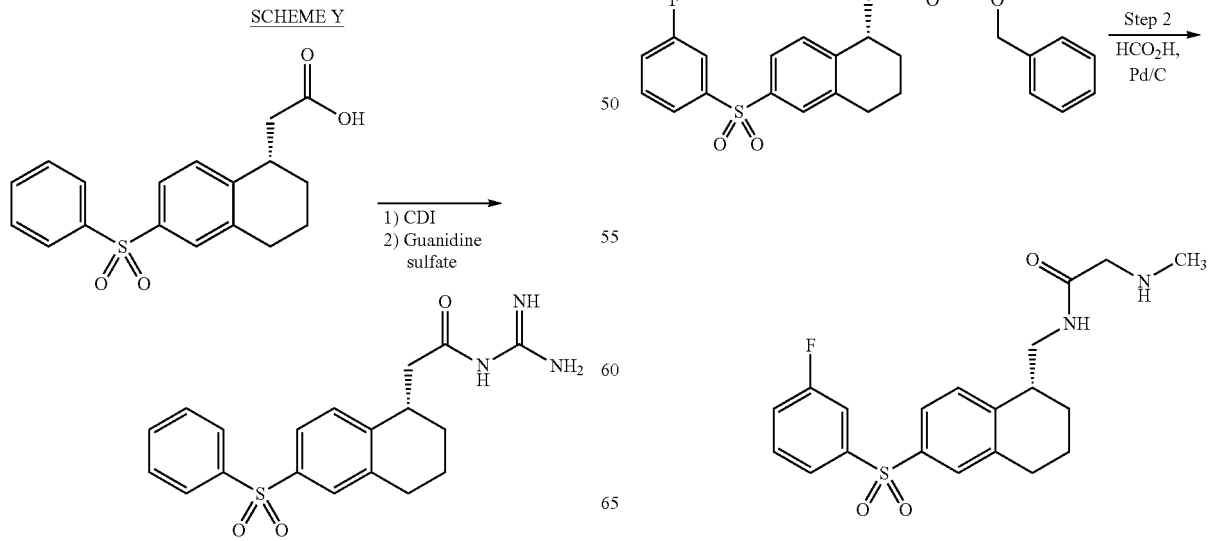

(6-Benzenesulfonyl-1,2,3,4-tetrahydro-naphthalen-1-yl)-acetic acid (0.30 grams, 0.80 mmole) and carbonyl diimidazole (0.13 gms, 0.90 mmole) in 30 mL DMF was stirred for three hours at room temperature. Guanidine sulfate (90 mg) was added, followed by 0.1 ml diisopropylethylamine, and the reaction mixture was stirred overnight. The reaction mixture was diluted with water, and the resulting white crystals were collected by filtration, washed with water, and dried under vacuum to afford 190 mg of N-[2-(6-Benzenesulfonyl-1,2,3,4-tetrahydro-naphthalen-1-yl)-acetyl]-guanidine, M+H=372.

Similarly prepared from [6-(3-Fluoro-benzenesulfonyl)-1,2,3,4-tetrahydro-naphthalen-1-yl]-acetic acid was (R)—N-{2-[6-(3-Fluoro-benzenesulfonyl)-1,2,3,4-tetrahydro-naphthalen-1-yl]-acetyl}-guanidine, M+H=390.

Example 23

N-[6-(3-Fluoro-benzenesulfonyl)-1,2,3,4-tetrahydro-naphthalen-1-ylmethyl]-2-methylamino-acetamide The synthetic procedure described in this Example was carried out according to the process shown in Scheme Z.

SCHEME Z

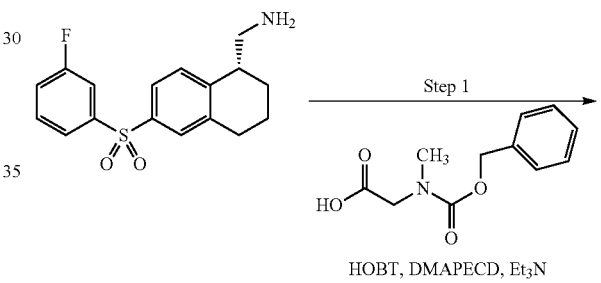

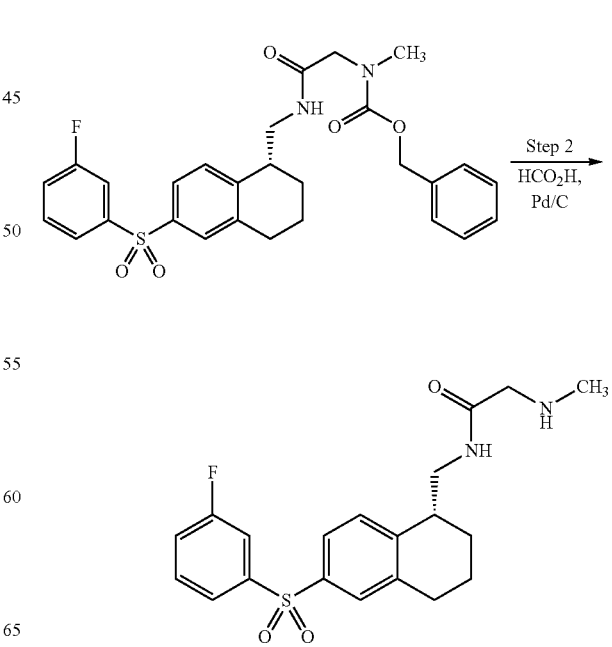

Step 1

({[6-(3-Fluoro-benzenesulfonyl)-1,2,3,4-tetrahydro-naphthalen-1-ylmethyl]-carbamoyl}-methyl)-methyl-carbamic acid benzyl ester

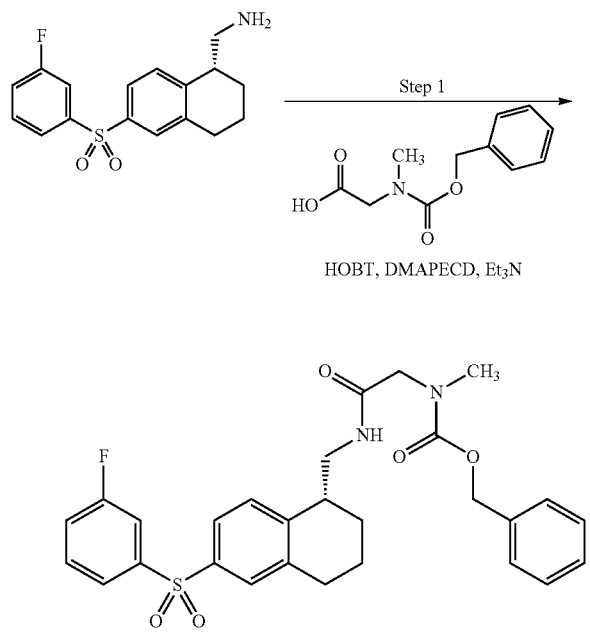 [SMILES: NC[C@@H]1CCCc2cc(S(=O)(=O)c3cccc(F)c3)ccc21 ; CN(CC(=O)O)C(=O)OCc1ccccc1 ; CN(CC(=O)NC[C@@H]1CCCc2cc(S(=O)(=O)c3cccc(F)c3)ccc21)C(=O)OCc1ccccc1]

C-[6-(3-Fluoro-benzenesulfonyl)-1,2,3,4-tetrahydro-naphthalen-1-yl]-methylamine hydrochloride (0.2 gms, 0.56 mmole), (Benzyloxycarbonyl-methyl-amino)-acetic acid (0.15 gms, 0.67 mmole), 1-hydroxybenzotriazole (0.11 gms, 0.84 mmole), 0.16 gms N-(3-dimethylaminopropyl)-N-ethylcarbodiimide (0.16 gms, 0.84 mmole) and triethylamine (0.50 ml, 3.36 mmole) in 30 mL methylene chloride was stirred at room temperature for 24 hours. The reaction was quenched with 0.2 ml water, and the entire mixture was absorbed on to silica gel and medium pressure chromatography, eluting with ethyl acetate, gave 0.15 gms of ({[6-(3-Fluoro-benzenesulfonyl)-1,2,3,4-tetrahydro-naphthalen-1-ylmethyl]-carbamoyl}-methyl)-methyl-carbamic acid benzyl ester as an oil.

Step 2

N-[6-(3-Fluoro-benzenesulfonyl)-1,2,3,4-tetrahydro-naphthalen-1-ylmethyl]-2-methylamino-acetamide

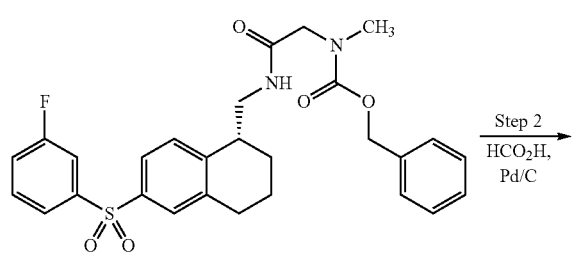

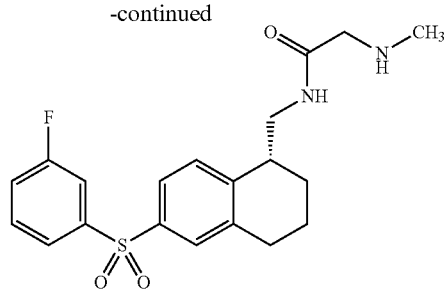

To a stirring solution of ({[6-(3-Fluoro-benzenesulfonyl)-1,2,3,4-tetrahydro-naphthalen-1-ylmethyl]-carbamoyl}-methyl)-methyl-carbamic acid benzyl ester (0.15 g) in 20 ml methanol and 2 ml formic acid at room temperature was added 0.1 gms of 10% palladium on carbon. After stirring for three hours the mixture was filtered thru Celite and the clear filtrate was concentrated to dryness. The residue was recrystallized from ethyl acetate and diethyl ether to give 0.090 gms of N-[6-(3-Fluoro-benzenesulfonyl)-1,2,3,4-tetrahydro-naphthalen-1-ylmethyl]-2-methylamino-acetamide formate salt: M+H=391.

Example 24

2-{[6-(3-Fluoro-benzenesulfonyl)-1,2,3,4-tetrahydro-naphthalen-1-ylmethyl]amino}-N-methyl-acetamide The synthetic procedure described in this Example was carried out according to the process shown in Scheme AA.

SCHEME AA

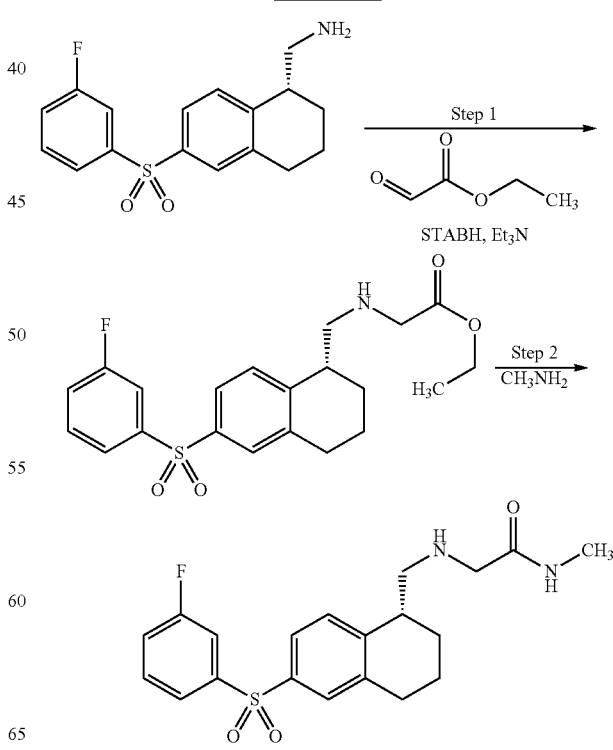

Step 1

{[6-(3-Fluoro-benzenesulfonyl)-1,2,3,4-tetrahydro-naphthalen-1-ylmethyl]-amino}-acetic acid ethyl ester

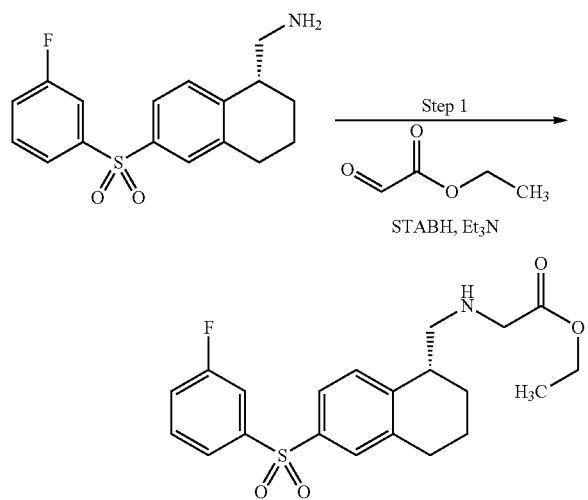

C-[6-(3-Fluoro-benzenesulfonyl)-1,2,3,4-tetrahydro-naphthalen-1-yl]-methylamine hydrochloride (0.5 gms, 1.41 mmole) and triethyl amine (0.2 ml, 1.55 mmole) in 25 ml dichloroethane were stirred together for three minutes, and then the solution cooled in an ice-bath. A 50% solution of ethylgloxylate (0.32 ml, 1.55 mmole) in toluene was added, and then followed by sodiumtriacetoxyborohydride (0.7 gms, 3.08 mmle). The reaction was stirred for four hours and then was quenched by addition of 2% sodium carbonate solution. The mixture was extracted twice with ethyl acetate, and the combine organic extracts were washed with saturated NaCl solution, dried over magnesium sulfate, filtered, and stripped to an oil under reduced pressure to give {[6-(3-Fluoro-benzenesulfonyl)-1,2,3,4-tetrahydro-naphthalen-1-ylmethyl]-amino}-acetic acid ethyl ester. The HCl salt was crystallized from diethyl ether-methanol. Yield: 0.42 gms, M+H=406.

Step 2

2-{[6-(3-Fluoro-benzenesulfonyl)-1,2,3,4-tetrahydro-naphthalen-1-ylmethyl]-amino}-N-methyl-acetamide

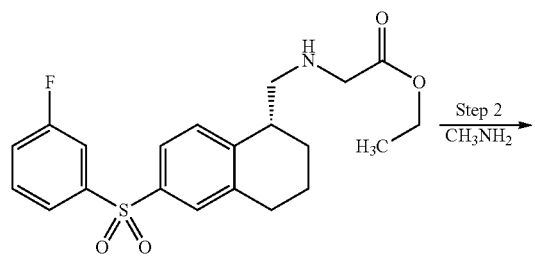

-continued

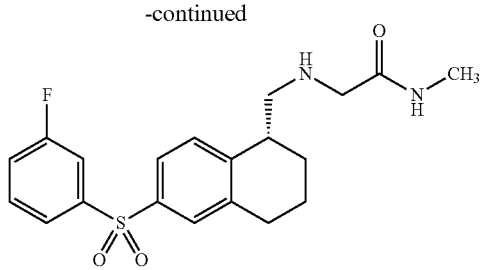

{[6-(3-Fluoro-benzenesulfonyl)-1,2,3,4-tetrahydro-naphthalen-1-ylmethyl]-amino}-acetic acid ethyl ester (0.42 g) was dissolved in 20 m of 1.1 molar methylamin in methanol. The solution was stirred at room temperature for 24 hours and then concentrated to an oil under reduced pressure. The oil was dissolved in ethanol and 1N HCl in diethyl ether was added to precipitate 2-{[6-(3-Fluoro-benzenesulfonyl)-1,2,3,4-tetrahydro-naphthalen-1-ylmethyl]-amino}-N-methyl-acetamide as a hydrochloride salt. Yield 0.045 gms, M+H=391.

Example 25

(R)-[6-(3-Fluoro-benzenesulfonyl)-1,2,3,4-tetrahydro-naphthalen-1-ylmethyl]-urea The synthetic procedure described in this Example was carried out according to the process shown in Scheme BB.

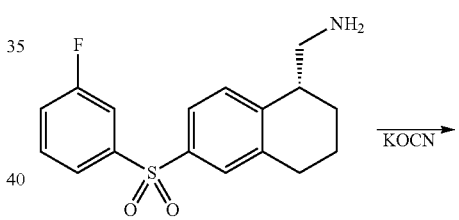

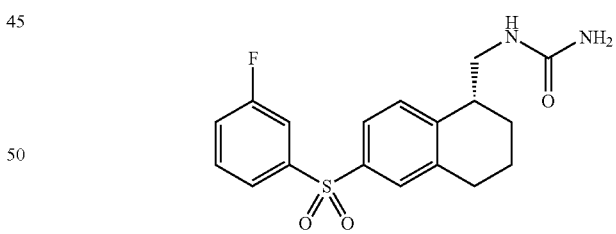

C-[6-(3-Fluoro-benzenesulfonyl)-1,2,3,4-tetrahydro-naphthalen-1-yl]-methylamine hydrochloride (0.5 gms, 1.41 mmole) and potassium cyanate (0.137 g, 1.69 mmol) added to to 30 mL stirring water, and the mixture was heated to 60° C. for five minutes. The reaction mixture was then cooled to room temperature, and the resulting white precipitate was collected by filtration, washed with cold water, and dried under vacuum to give 0.408 g of (R)-[6-(3-Fluoro-benzenesulfonyl)-1,2,3,4-tetrahydro-naphthalen-1-ylmethyl]-urea, M+H=363.

Example 26

(R)—N-[6-(3-Fluoro-benzenesulfonyl)-1,2,3,4-tetrahydro-naphthalen-1-ylmethyl]-methanesulfonamide The synthetic procedure described in this Example was carried out according to the process shown in Scheme CC.

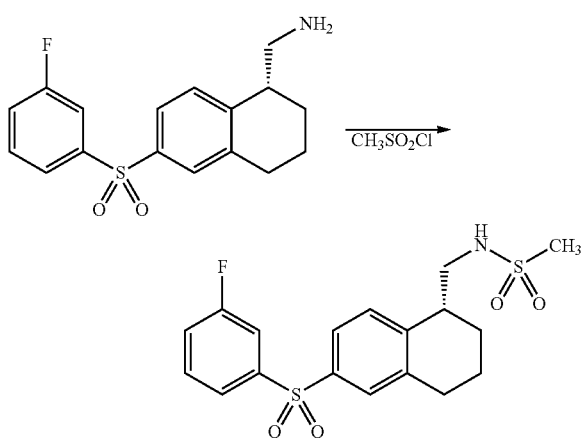

C-[6-(3-Fluoro-benzenesulfonyl)-1,2,3,4-tetrahydro-naphthalen-1-yl]-methylamine hydrochloride (0.5 gms, 1.41 mmole) was dissolved in 20 mL methylene chloride and 0.5 mL pyridine, and the mixture was cooled in an ice bath. Methanesulfonyl chloride (0.16 g, 1.41 mmol) was added dropwise, and the reaction mixture was stirred for five minutes at ice bath temperature, then allowed to warm to room temperature. The reaction mixture was quenched by addition of water, and was extracted with methylene chloride. The organic layer was washed with water, dried (MgSO$_4$), filtered and concentrated under reduced pressure. The residue was recrystallized from diethyl ether to give 0.39 g of (R)—N-[6-(3-Fluoro-benzenesulfonyl)-1,2,3,4-tetrahydro-naphthalen-1-ylmethyl]-methanesulfonamide, M+H=398.

Example 27

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |

| Topical Formulation | |
|---|---|
| Ingredients | grams |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 28

Radioligand Binding Studies

This example illustrates in vitro radioligand binding studies of compound of formula I.

The binding activity of compounds of this invention in vitro was determined as follows. Duplicate determinations of 5-HT$_6$ ligand affinity were made by competing for binding of [$^3$H]LSD in cell membranes derived from HEK293 cells stably expressing recombinant human 5-HT$_6$ receptor. Duplicate determinations of 5-HT$_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably expressing recombinant human 5-HT$_{2A}$ receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J Pharmacol. June; 115(4): 622-8 (1995).

For estimation of affinity at the 5-HT$_6$ receptor, all determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. For estimation of affinity at the 5-HT$_{2A}$ receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-HT$_6$) or 60 min. at 32° C. (for 5-HT$_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H] Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{B\text{max} - \text{basal}}{1 + 10^{-Hill(\log[ligand] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, compounds of Formula I were tested and found to be selective 5-HT$_6$ antagonists, selective 5-HT$_{2A}$ antagonists, or both. For example, the compound 3-(6-Benzenesulfonyl-1,2,3,4-tetrahydro-naphthalen-1-yl)-propionamidine exhibited a pKi of approximately 9.85 for 5-HT$_6$, and N-(6-Benzenesulfonyl-1,2,3,4-tetrahydro-naphthalen-1-ylmethyl)-acetamidine showed a pKi of approximately 9.55 for 5-HT$_{2A}$.

Example 29

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. Behav. Brain Res. 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. The compound (R)-[6-(3-fluoro-benzenesulfonyl)-1,2,3,4-tetrahydro-naphthalen-1-ylmethyl]-urea, or a pharmaceutically acceptable salt thereof.

2. The compound (R)—N-(6-benzenesulfonyl-8-fluoro-1,2,3,4-tetrahydro-naphthalen-1-ylmethyl)-acetamide, or a pharmaceutically acceptable salt thereof.

3. A method of enhancing cognitive memory, the method comprising administering an effective amount of the compound of claim 2 to a subject in need thereof.

4. A method of enhancing cognitive memory, the method comprising administering an effective amount of the compound of claim 1 to a subject in need thereof.

5. A method of treating Alzheimer's disease, the method comprising administering an effective amount of the compound of claim 2 to a subject in need thereof, wherein the treating consists of relieving the disease state.

6. A method of treating Alzheimer's disease, the method comprising administering an effective amount of the compound of claim 1 to a subject in need thereof, wherein the treating consists of relieving the disease state.

* * * * *